United States Patent
Deng et al.

(10) Patent No.: US 12,240,812 B2
(45) Date of Patent: Mar. 4, 2025

(54) COMPOUND FOR INHIBITING PGE2/EP4 SIGNALING TRANSDUCTION INHIBITING, PREPARATION METHOD THEREFOR, AND MEDICAL USES THEREOF

(71) Applicant: Keythera (Suzhou) Pharmaceuticals Co. Ltd., Jiangsu (CN)

(72) Inventors: Yongqi Deng, Hong Kong (CN); Jian Sun, Hong Kong (CN)

(73) Assignee: Keythera (Suzhou) Pharmaceuticals Co. Ltd., Jiangsu (CN)

(*) Notice: Subject to any disclaimer, the term of this patent is extended or adjusted under 35 U.S.C. 154(b) by 677 days.

(21) Appl. No.: 17/423,248

(22) PCT Filed: Jan. 16, 2020

(86) PCT No.: PCT/CN2020/072487
§ 371 (c)(1),
(2) Date: Jul. 15, 2021

(87) PCT Pub. No.: WO2020/151566
PCT Pub. Date: Jul. 30, 2020

(65) Prior Publication Data
US 2022/0064113 A1 Mar. 3, 2022

(30) Foreign Application Priority Data
Jan. 22, 2019 (CN) .......................... 201910057555.2

(51) Int. Cl.
| | | |
|---|---|---|
| *C07D 209/10* | (2006.01) | |
| *A61K 45/06* | (2006.01) | |
| *A61P 35/00* | (2006.01) | |
| *C07D 401/06* | (2006.01) | |
| *C07D 401/14* | (2006.01) | |
| *C07D 405/06* | (2006.01) | |
| *C07D 413/06* | (2006.01) | |
| *C07D 417/06* | (2006.01) | |
| *C07D 471/04* | (2006.01) | |

(52) U.S. Cl.
CPC .......... *C07D 209/10* (2013.01); *A61K 45/06* (2013.01); *A61P 35/00* (2018.01); *C07D 401/06* (2013.01); *C07D 401/14* (2013.01); *C07D 405/06* (2013.01); *C07D 413/06* (2013.01); *C07D 417/06* (2013.01); *C07D 471/04* (2013.01)

(58) Field of Classification Search
CPC .. C07D 209/10; C07D 401/06; C07D 405/06; C07D 413/06; C07D 417/06; C07D 471/04; C07D 401/14; C07D 471/06; A61P 35/00; A61K 45/06
USPC ..................................................... 514/235.2
See application file for complete search history.

(56) References Cited

U.S. PATENT DOCUMENTS

| | | | |
|---|---|---|---|
| 8,158,671 | B2 | 4/2012 | Boyd et al. |
| 8,962,659 | B2 | 2/2015 | Schiffler et al. |
| 10,005,721 | B2 | 6/2018 | Blanco-Pillado et al. |
| 10,416,492 | B2 | 9/2019 | Cheng et al. |
| 2018/0157113 | A1 | 6/2018 | Cheng et al. |

FOREIGN PATENT DOCUMENTS

| | | | |
|---|---|---|---|
| CN | 101622230 A | 1/2010 | |
| CN | 104411684 A | 3/2015 | |
| CN | 105793236 A | 7/2016 | |
| EP | 2172447 A1 | 4/2010 | |
| WO | WO-2008104055 A1 * | 9/2008 | ........... C07D 209/08 |
| WO | 2009048558 A1 | 4/2009 | |
| WO | 2013096496 A2 | 6/2013 | |
| WO | 2015179615 A1 | 11/2015 | |
| WO | 2017041323 A1 | 3/2017 | |
| WO | 2017066633 A1 | 4/2017 | |
| WO | 2018084230 A1 | 5/2018 | |
| WO | 2018195123 A1 | 10/2018 | |

OTHER PUBLICATIONS

Written Opinion of the International Searching Authority: China National Intellectual Property Administration; International Application No. PCT/CN2020/072487; Apr. 15, 2020; 9 pages.
International Preliminary Report on Patentability; The International Bureau of WIPO; International Application No. PCT/CN2020/072487; Jul. 27, 2021; 10 pages.
International Search Report; China National Intellectual Property Administration; International Application No. PCT/CN2020/072487; Apr. 15, 2020; 10 pages.
Albu, Diana I. et al.; EP4 Antagonism by E7046 diminishes Myeloid immunosuppression and synergizes with Tregreducing IL-2-Diphtheria toxin fusion protein in restoring anti-tumor immunity; OncoImmunology; 2017; 15 pages; vol. 6, No. 8; Taylor & Francis Group.
Extended European Search Report; European Patent Office; European Application No. 20744659.2; Jan. 14, 2022; 6 pages.

(Continued)

*Primary Examiner* — Yevgeny Valenrod
(74) *Attorney, Agent, or Firm* — Taft Stettinius & Hollister LLP

(57) ABSTRACT

A compound of formula (I), a preparation method therefor, a pharmaceutical composition containing a derivative thereof, and the therapeutic uses thereof, especially inhibiting PGE2/EP4 signalling transduction and the uses thereof for treating cancer, acute or chronic pain, migraine, osteoarthritis, rheumatoid arthritis, gout, bursitis, ankylosing spondylitis, primary dysmenorrhea, tumour or arteriosclerosis.

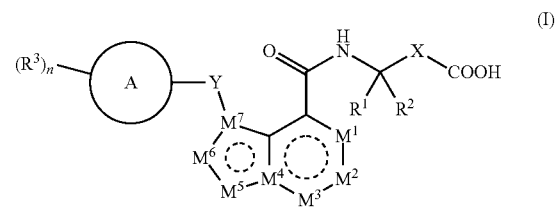

12 Claims, 3 Drawing Sheets

(56) References Cited

OTHER PUBLICATIONS

Response to Extended European Search Report; European Patent Office; European Application No. 20744659.2; dated Jun. 13, 2022, 6 pages.
European Office Action; European Patent Office; European Application No. 20744659.2; Dec. 13, 2023; 4 pages.
Response to European Office Action; European Patent Office; European Application No. 20744659.2; dated Jan. 18, 2024, 3 pages.

* cited by examiner

COMPOUND FOR INHIBITING PGE2/EP4 SIGNALING TRANSDUCTION INHIBITING, PREPARATION METHOD THEREFOR, AND MEDICAL USES THEREOF

CROSS-REFERENCE TO RELATED APPLICATIONS

This application is a U.S. National Phase of International PCT Application No. PCT/CN2020/072487, which was filed on Jan. 16, 2020, and which claims priority to Chinese Patent Application Serial No. 201910057555.2, which was filed on Jan. 22, 2019. The contents of each application are incorporated herein by reference in their entireties.

FIELD OF THE INVENTION

The present invention belongs to the field of medicine, and relates to a compound of formula (I), a method for preparing the same, a pharmaceutical composition comprising the same, and a use thereof as a therapeutic agent, especially a PGE2/EP4 signaling transduction inhibitor in treating cancer and chronic inflammatory disease.

BACKGROUND OF THE INVENTION

Prostaglandin E2 (PGE2) is one of the main products produced by the action of cyclooxygenase (COX) on arachidonic acid. It is well known to be involved in many physiological and pathophysiological reactions. PGE2-mediated intracellular signaling transduction depends on its binding to one or more specific prostaglandin E receptors (EP1-4) in the target cell, wherein these receptors are coupled to different G proteins. EP4 is expressed in a variety of tissues and cells, including immune, bone and joint, cardiovascular, gastrointestinal and respiratory systems as well as cancer cells. The coupling of EP4 with Ga can activate adenylate cyclase (AC) and catalyze the formation of the second messenger cAMP. The main role of cAMP is to bind and activate protein kinase A (PKA), which in turn phosphorylates target proteins in the cell. In addition, EP4 also stimulates the non-classical pathway of phosphatidylinositol 3 kinase (PI3K)/protein kinase B (PKB, also known as Akt) to promote cell survival, and activates extracellular regulatory kinase (ERK) to promote migration and proliferation.

More and more preclinical data support the potential therapeutic value of prostaglandin E receptor 4 (EP4) antagonist in several indications. Most scientific data indicate that selective EP4 antagonists may be an effective inflammatory pain relief drug, and its intestinal tolerance is superior to NSAIDs and COX-2 inhibitors, which are the standard drugs at present. Importantly, EP4 antagonists can achieve a higher cardiovascular safety, since they do not directly interfere with the biosynthesis of prostaglandin E (PGE2) and other prostaglandins (such as prostacyclin and thromboxane). EP4 receptor antagonists may also have a therapeutic application in treating migraine, since EP4 receptor is involved in the PGE2-mediated cerebral vasodilation, which is an important factor in migraine.

Overexpression of COX2 in various tumor types leads to an increased level of PGE2, indicating that blocking PGE2 signaling transduction with selective EP4 antagonists during cancer treatment may be beneficial to cancer patients. It is reported that EP4 receptor plays an important role in many neurodegenerative diseases, such as multiple sclerosis and Alzheimer's disease, in which PGE2 is involved.

Studies have shown that the PGE2/EP4 signaling pathway is related to the occurrence of colorectal cancer, breast cancer, lung cancer, prostate cancer, ovarian cancer, bladder cancer, liver cancer and the like. The activation of this cascade signal, elevated PGE2 level in tumor or EP4 overexpression can inactivate the anti-tumor immune cells of the host, enhance cancer cell proliferation, migration and metastasis, and promote tumor-related angiogenesis, thereby promoting tumor progression. On the other hand, EP4-knockout mice show delayed tumorigenesis in the context of APCmin mutation compared with wild-type mice, indicating its tumor-promoting activity.

Selective EP4 receptor antagonists can inhibit PGE2-induced cancer cell proliferation in vitro, and can slow down tumor progression and metastasis in various preclinical tumor models. Selective EP4 receptor antagonists also block the induction of myeloid derived suppressor cells, restore the activity of natural killer cells, and enhance the production of pro-inflammatory cytokine (TNF-α) and IL-12 by myeloid cells and Th1 cells. These data indicate that inhibiting PGE2/EP4 signaling transduction may have therapeutic value in cancer and other chronic inflammatory disease. Therefore, it is very important to invent new compounds that can block the PGE2/EP4 signaling transduction pathway to fill the unmet medical needs.

E7046 (i.e. (S)-4-(1-(3-(difluoromethyl)-1-methyl-5-(3-(trifluoromethyl)phenoxy)-1H-pyrazole-4-carboxamido)ethyl)benzoic acid) is an EP4 receptor antagonist developed by Eisai. It changes the tumor microenvironment by acting on the EP4 receptor to promote the immune function of the body. E7046 has been demonstrated to have a strong anti-cancer activity and immune benefit in preclinical in vitro and in vivo tests, and the combination therapies (for example with radiotherapy, immune checkpoint inhibitors) can significantly inhibit the growth of a variety of tumors. A phase Ib clinical trial of E7046 in combination with radiotherapy and chemotherapy is underway (WO2015179615A1 and Diana I. Albu et al., Oncoimmunology, 2017, 6(8): e1338239).

E7046

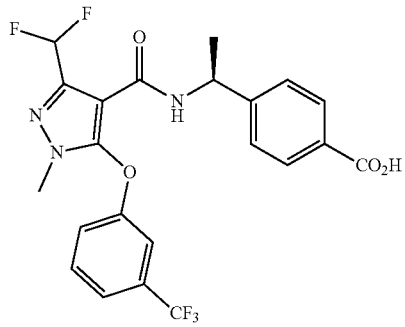

(i.e. 4-(1-(1-(4-(trifluoromethyl)benzyl)-1H-indole-7-carboxamido)cyclopropyl)benzoic acid) is an EP4 receptor antagonist developed by Merck for treating acute and chronic pain, osteoarthritis, rheumatoid arthritis and cancer (WO2008104055A1).

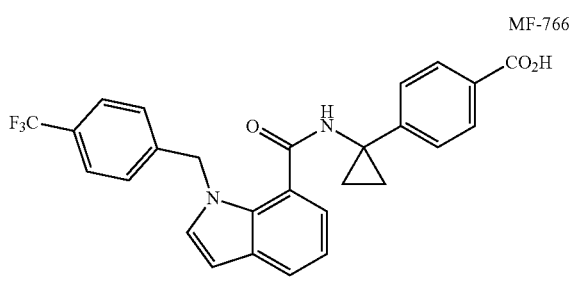 [SMILES: O=C(O)c1ccc(C2(NC(=O)c3cccc4ccn(Cc5ccc(C(F)(F)F)cc5)c34)CC2)cc1]

MF-766

The existing patent applications related to EP4 receptor antagonists also include, for example, WO2017066633A1, WO2017041323A1, WO2018084230A1 and the like. It is still necessary to continue to develop EP4 receptor antagonists with a high potency and selectivity due to the huge market demand.

SUMMARY OF THE INVENTION

The object of the present invention is to provide a compound that inhibits the PGE2/EP4 signaling transduction with a high activity and selectivity. In order to achieve this object, the inventor has repeatedly conducted serious studies, and surprisingly found a compound of formula (I) that contains

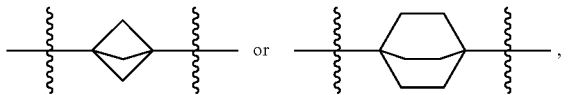 [SMILES: *C12CC(*)(C1)C2 ; *C12CCC(*)(CC1)CC2]

thereby completing the present invention.

The present invention relates to a following compound of formula (I):

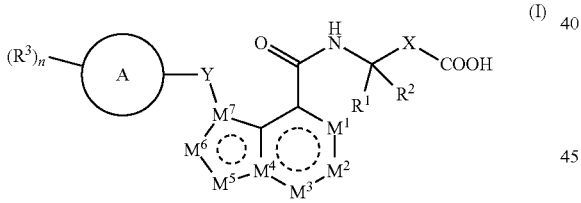

or a tautomer, mesomer, racemate, enantiomer, diastereomer thereof, or mixture thereof, or a pharmaceutically acceptable salt thereof,
wherein:
$M^1$, $M^2$, $M^3$, $M^5$, $M^6$ and $M^7$ are each independently an N atom or C—$R^4$;
$M^4$ is selected from the group consisting of N atom and C atom;
ring A is selected from the group consisting of $C_{6-10}$ aryl, $C_{3-6}$ cycloalkyl, 5 to 10 membered heteroaryl and 3 to 6 membered heterocyclyl;
X is

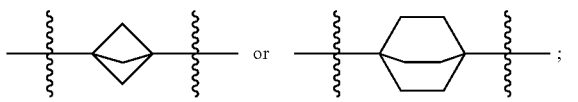

Y is selected from the group consisting of a bond, $C_{1-4}$ alkylene, —$CR^5R^6$—, —O—, —O$C_{1-4}$ alkylene-, —$NR^9C_{1-4}$ alkylene- and —$NR^9$—, wherein the $C_{1-4}$ alkylene is optionally substituted by one or more substituents selected from the group consisting of H atom, D atom, halogen, hydroxy, cyano, amino, nitro, $C_{1-4}$ alkyl, $C_{1-4}$ alkoxy, halo$C_{1-4}$ alkyl, halo$C_{1-4}$ alkoxy, hydroxy$C_{1-4}$ alkyl, $C_{3-6}$ cycloalkyl, 3 to 6 membered heterocyclyl, $C_{6-10}$ aryl and 5 to 10 membered heteroaryl;

$R^1$ and $R^2$ are identical or different and are each independently selected from the group consisting of H atom, D atom, cyano, $C_{1-4}$ alkyl, $C_{1-4}$ alkoxy, $C_{3-6}$ cycloalkyl, 3 to 6 membered heterocyclyl, —C(O)O$R^4$, C(O)N$R^7R^8$, —COR$^4$, —S(O)$_m$R$^4$, —NR$^7$R$^8$, $C_{6-10}$ aryl and 5 to 10 membered heteroaryl, wherein the $C_{1-4}$ alkyl and $C_{1-4}$ alkoxy are each independently optionally substituted by one or more substituents selected from the group consisting of H atom, D atom, halogen, hydroxy, cyano, amino, nitro, $C_{1-4}$ alkyl, $C_{1-4}$ alkoxy, halo$C_{1-4}$ alkyl, halo$C_{1-4}$ alkoxy, hydroxy$C_{1-4}$ alkyl, $C_{3-6}$ cycloalkyl, 3 to 6 membered heterocyclyl, —C(O)O$R^4$, C(O)N$R^7R^8$, —COR$^4$, —NR$^4$C(O)N$R^7R^8$, —OC(O)N$R^7R^8$, —NR$^7$C(O)O$R^4$, —S(O)$_m$R$^4$, —NR$^7R^8$, $C_{6-10}$ aryl and 5 to 10 membered heteroaryl; or, $R^1$ and $R^2$ together with the atom to which they are attached form a $C_{3-6}$ cycloalkyl or 3 to 6 membered heterocyclyl, wherein the $C_{3-6}$ cycloalkyl and 3 to 6 membered heterocyclyl are each independently optionally substituted by one or more substituents selected from the group consisting of D atom, halogen, hydroxy, cyano, amino, nitro, —C(O)O$R^4$, C(O)N$R^7R^8$, —COR$^4$, —NR$^4$C(O)N$R^7R^8$, —OC(O)N$R^7R^8$, —NR$^7$C(O)O$R^4$, —S(O)$_m$R$^4$, —NR$^7R^8$, $C_{1-4}$ alkyl, $C_{1-4}$ alkoxy, halo$C_{1-4}$ alkyl, halo$C_{1-4}$ alkoxy, hydroxy$C_{1-4}$ alkyl, $C_{3-6}$ cycloalkyl, 3 to 6 membered heterocyclyl, $C_{6-10}$ aryl and 5 to 10 membered heteroaryl;

each $R^3$ is identical or different and each is independently selected from the group consisting of H atom, D atom, halogen, hydroxy, cyano, amino, nitro, $C_{1-4}$ alkyl, $C_{1-4}$ alkoxy, $C_{3-6}$ cycloalkyl, 3 to 6 membered heterocyclyl, $C_{6-10}$ aryl, 5 to 10 membered heteroaryl, —C(O)R$^4$, —C(O)O$R^4$, —OC(O)N$R^7R^8$, —NR$^7$C(O)O$R^4$, —S(O)$_m$R$^4$, —NR$^7R^8$ and —C(O)N$R^7R^8$, wherein the $C_{1-4}$ alkyl, $C_{1-4}$ alkoxy, $C_{3-6}$ cycloalkyl, 3 to 6 membered heterocyclyl, $C_{6-10}$ aryl and 5 to 10 membered heteroaryl are each independently optionally substituted by one or more substituents selected from the group consisting of $C_{1-4}$ alkyl, hydroxy$C_{1-4}$ alkyl, $C_{1-4}$ alkoxy, halo$C_{1-4}$ alkyl, halo$C_{1-4}$ alkoxy, halogen, hydroxy, cyano, amino and nitro;

$R^4$ is selected from the group consisting of H atom, D atom, halogen, hydroxy, amino, $C_{1-4}$ alkyl, $C_{1-4}$ alkoxy, $C_{3-6}$ cycloalkyl, 3 to 6 membered heterocyclyl, $C_{6-10}$ aryl and 5 to 10 membered heteroaryl, wherein the $C_{1-4}$ alkyl, $C_{1-4}$ alkoxy, $C_{3-6}$ cycloalkyl, 3 to 6 membered heterocyclyl, $C_{6-10}$ aryl and 5 to 10 membered heteroaryl are each independently optionally substituted by one or more substituents selected from the group consisting of $C_{1-4}$ alkyl, hydroxy$C_{1-4}$ alkyl, $C_{1-4}$ alkoxy, halo$C_{1-4}$ alkyl, halo$C_{1-4}$ alkoxy, halogen, hydroxy, cyano, amino and nitro;

$R^5$ and $R^6$ are each independently selected from the group consisting of H atom, D atom, $C_{1-4}$ alkyl, $C_{3-6}$ cycloalkyl, 3 to 6 membered heterocyclyl, $C_{6-10}$ aryl and 5 to 10 membered heteroaryl, wherein the $C_{1-4}$ alkyl, $C_{3-6}$ cycloalkyl, 3 to 6 membered heterocyclyl, $C_{6-10}$ aryl and 5 to 10 membered heteroaryl are each independently optionally substituted by one or more substituents selected from the group consisting of $C_{1-4}$ alkyl, hydroxy$C_{1-4}$ alkyl, $C_{1-4}$ alkoxy, halo$C_{1-4}$ alkyl, halo$C_{1-4}$ alkoxy, halogen, hydroxy, cyano, amino and nitro; or, $R^5$ and $R^6$ together with the atom to which they are attached form a $C_{3-6}$ cycloalkyl or 3 to 6 membered heterocyclyl, wherein the $C_{3-6}$ cycloalkyl and 3 to 6 membered heterocyclyl are each independently optionally substituted by one or more substituents selected from the group consisting of halogen, hydroxy, cyano, amino, nitro, $C_{1-4}$ alkyl, $C_{1-4}$ alkoxy, halo$C_{1-4}$ alkyl, halo$C_{1-4}$ alkoxy, hydroxy$C_{1-4}$ alkyl, $C_{3-6}$ cycloalkyl, 3 to 6 membered heterocyclyl, $C_{6-10}$ aryl and 5 to 10 membered heteroaryl;

$R^7$ and $R^8$ are each independently selected from the group consisting of H atom, D atom, $C_{1-4}$ alkyl, halo$C_{1-4}$ alkyl, $C_{3-6}$ cycloalkyl, 3 to 6 membered heterocyclyl, $C_{6-10}$ aryl and 5 to 10 membered heteroaryl, wherein the $C_{1-4}$ alkyl, halo$C_{1-4}$ alkyl, $C_{3-6}$ cycloalkyl, 3 to 6 membered heterocyclyl, $C_{6-10}$ aryl and 5 to 10 membered heteroaryl are each independently optionally substituted by one or more substituents selected from the group consisting of $C_{1-4}$ alkyl, hydroxy$C_{1-4}$ alkyl, $C_{1-4}$ alkoxy, halo$C_{1-4}$ alkyl, halo$C_{1-4}$ alkoxy, halogen, hydroxy, cyano, amino and nitro;

$R^9$ is selected from the group consisting of H atom, D atom and $C_{1-4}$ alkyl, wherein the $C_{1-4}$ alkyl is optionally substituted by one or more substituents selected from the group consisting of hydroxy$C_{1-4}$ alkyl, $C_{1-4}$ alkoxy, halo$C_{1-4}$ alkyl, halo$C_{1-4}$ alkoxy, halogen, hydroxy, cyano, amino and nitro;

m is 0, 1 or 2; and n is 0, 1, 2, 3 or 4.

In a preferred embodiment, the compound of formula (I) is a compound of formula (II):

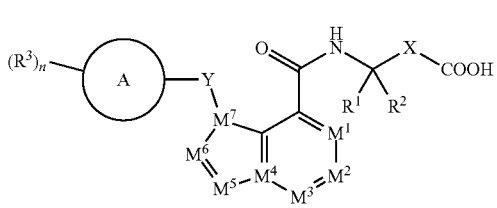

(II)

wherein $M^1$, $M^3$, $M^5$ and $M^6$ are each independently a CH or C-halogen, $M^2$ is a C—$R^4$ or N atom, $M^7$ is an N atom, $M^4$ is a C atom, and ring A, $R^1$, $R^2$, $R^3$, $R^4$, X, Y and n are as defined in formula (I).

In another preferred embodiment, in the compound of formula (I), Y is a $C_{1-4}$ alkylene, and preferably methylene.

In another preferred embodiment, in the compound of formula (I), $R^1$ and $R^2$ are identical or different and are each independently selected from the group consisting of H atom, D atom and $C_{1-4}$ alkyl; or, $R^1$ and $R^2$ together with the atom to which they are attached form a $C_{3-6}$ cycloalkyl, and preferably cyclopropyl.

In another preferred embodiment, the compound of formula (I) is a compound of formula (III):

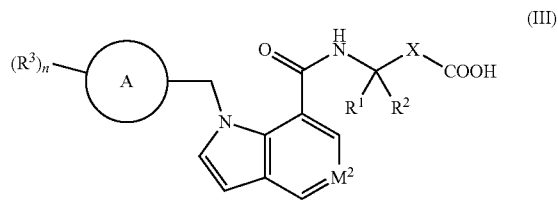

(III)

or a tautomer, mesomer, racemate, enantiomer, diastereomer thereof, or mixture thereof, or a pharmaceutically acceptable salt thereof, wherein:

$R^1$ and $R^2$ are identical or different and are each independently selected from the group consisting of H atom, D atom and $C_{1-4}$ alkyl; or, $R^1$ and $R^2$ together with the atom to which they are attached form a $C_{3-6}$ cycloalkyl, and preferably cyclopropyl;

$M^2$ is an N atom or C—$R^4$;

$R^4$ is selected from the group consisting of H atom, D atom and halogen; and

X, ring A, $R^3$ and n are as defined in formula (I).

In another preferred embodiment, in the compound of formula (I), ring A is selected from the group consisting of phenyl, pyridyl, quinolinyl, benzofuranyl, morpholinyl, pyrazole, cyclopropyl, isoxazole, benzoxazole and benzothiazole.

In another preferred embodiment, in the compound of formula (I), each $R^3$ is identical or different and each is independently selected from the group consisting of H atom, D atom, halogen, $C_{1-4}$ alkyl, fluoro$C_{1-4}$ alkyl, phenyl, hydroxy$C_{1-4}$ alkyl-substituted phenyl, morpholinyl, pyridyl, pyrazolyl, $C_{1-4}$ alkyl-substituted pyrazolyl, hydroxy$C_{1-4}$ alkyl-substituted pyrazolyl, cyclopropyl, isoxazolyl and piperidinyl.

Typical compounds of the present invention include, but are not limited to:

| Compound No. | Structure | Chemical name |
|---|---|---|
| 1 | 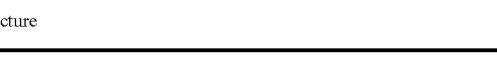 | 3-(1-(1-(4-(Trifluoromethyl)benzyl)-1H-indole-7-carboxamido)cyclopropyl)bicyclo[1.1.1]pentane-1-carboxylic acid |

-continued

| Compound No. | Structure | Chemical name |
|---|---|---|
| 2 | 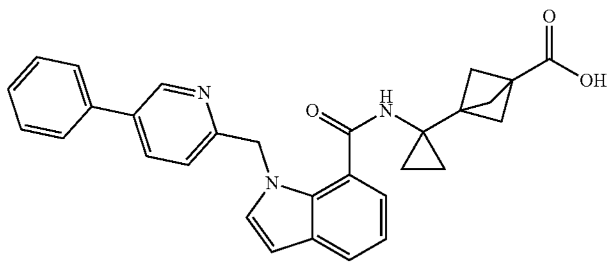 [SMILES: O=C(NC1(C23CC(C(=O)O)(C2)C3)CC1)c1cccc2ccn(Cc3ccc(-c4ccccc4)cn3)c12] | 3-(1-(1-((5-Phenylpyridin-2-yl)methyl)-1H-indole-7-carboxamido)cyclopropyl)bicyclo[1.1.1]pentane-1-carboxylic acid |
| 3 | 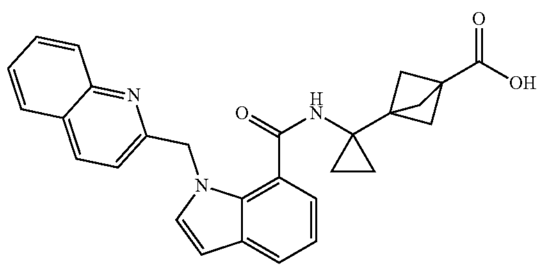 [SMILES: O=C(NC1(C23CC(C(=O)O)(C2)C3)CC1)c1cccc2ccn(Cc3ccc4ccccc4n3)c12] | 3-(1-(1-(Quinolin-2-ylmethyl)-1H-indole-7-carboxamido)cyclopropyl)bicyclo[1.1.1]pentane-1-carboxylic acid |
| 4 | 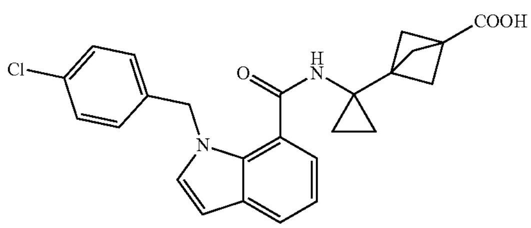 [SMILES: O=C(NC1(C23CC(C(=O)O)(C2)C3)CC1)c1cccc2ccn(Cc3ccc(Cl)cc3)c12] | 3-(1-(1-(4-Chlorobenzyl)-1H-indole-7-carboxamido)cyclopropyl)bicyclo[1.1.1]pentane-1-carboxylic acid |
| 5 | 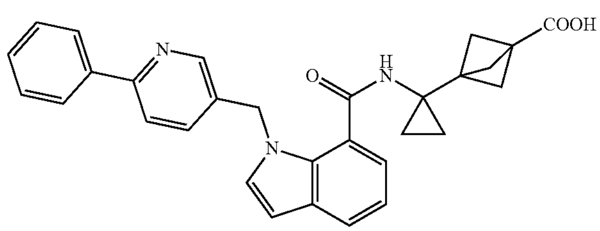 [SMILES: O=C(NC1(C23CC(C(=O)O)(C2)C3)CC1)c1cccc2ccn(Cc3ccc(-c4ccccc4)nc3)c12] | 3-(1-(1-((6-Phenylpyridin-3-yl)methyl)-1H-indole-7-carboxamido)cyclopropyl)bicyclo[1.1.1]pentane-1-carboxylic acid |
| 6 | 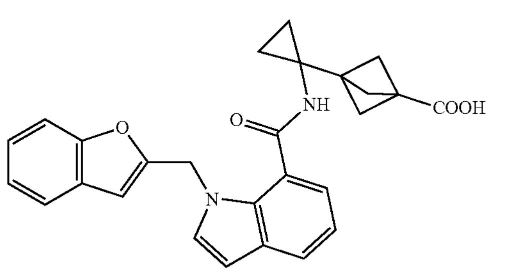 [SMILES: O=C(NC1(C23CC(C(=O)O)(C2)C3)CC1)c1cccc2ccn(Cc3cc4ccccc4o3)c12] | 3-(1-(1-(Benzofuran-2-ylmethyl)-1H-indole-7-carboxamido)cyclopropyl)bicyclo[1.1.1]pentane-1-carboxylic acid |
| 7 | 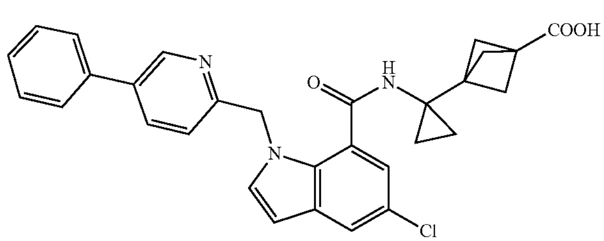 [SMILES: O=C(NC1(C23CC(C(=O)O)(C2)C3)CC1)c1cc(Cl)cc2ccn(Cc3ccc(-c4ccccc4)cn3)c12] | 3-(1-(5-Chloro-1-((5-phenylpyridin-2-yl)methyl)-1H-indole-7-carboxamido)cyclopropyl)bicyclo[1.1.1]pentane-1-carboxylic acid |

-continued

| Compound No. | Structure | Chemical name |
|---|---|---|
| 8 | 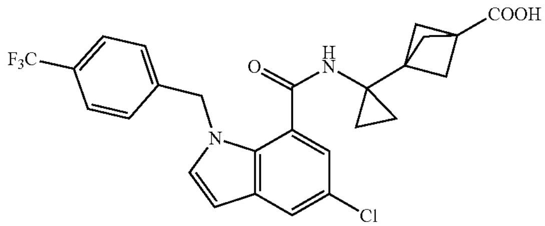 [SMILES: O=C(NC1(C23CC(C(=O)O)(C2)C3)CC1)c1cc(Cl)cc2ccn(Cc3ccc(C(F)(F)F)cc3)c12] | 3-(1-(5-Chloro-1-((5-(trifluoromethyl)pyridin-2-yl)methyl)-1H-indole-7-carboxamido)cyclopropyl)bicyclo[1.1.1]pentane-1-carboxylic acid |
| 9 | 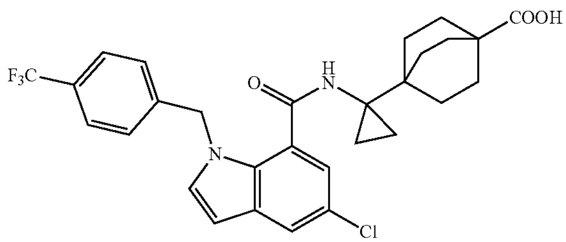 [SMILES: O=C(NC1(C23CCC(C(=O)O)(CC2)CC3)CC1)c1cc(Cl)cc2ccn(Cc3ccc(C(F)(F)F)cc3)c12] | 4-(1-(1-(4-(Trifluoromethyl)benzyl)-1H-indole-7-carboxamido)cyclopropyl)bicyclo[2.2.2]octane-1-carboxylic acid |
| 10 | 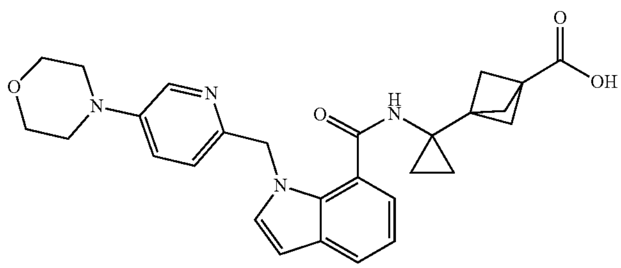 [SMILES: O=C(NC1(C23CC(C(=O)O)(C2)C3)CC1)c1cccc2ccn(Cc3ccc(N4CCOCC4)cn3)c12] | 3-(1-(1-((5-Morpholinopyridin-2-yl)methyl)-1H-indole-7-carboxamido)cyclopropyl)bicyclo[1.1.1]pentane-1-carboxylic acid |
| 11 | 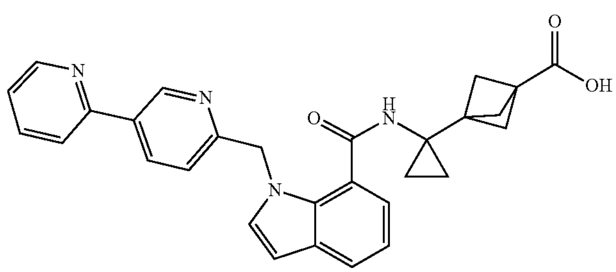 [SMILES: O=C(NC1(C23CC(C(=O)O)(C2)C3)CC1)c1cccc2ccn(Cc3ccc(-c4ccccn4)cn3)c12] | 3-(1-(1-([2,3'-Bipyridin]-6'-ylmethyl)-1H-indole-7-carboxamido)cyclopropyl)bicyclo[1.1.1]pentane-1-carboxylic acid |
| 12 | 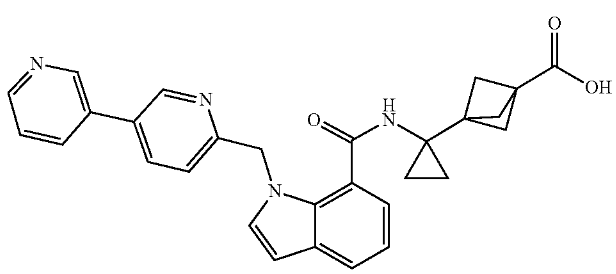 [SMILES: O=C(NC1(C23CC(C(=O)O)(C2)C3)CC1)c1cccc2ccn(Cc3ccc(-c4cccnc4)cn3)c12] | 3-(1-(1-([3,3'-Bipyridin]-6-ylmethyl)-1H-indole-7-carboxamido)cyclopropyl)bicyclo[1.1.1]pentane-1-carboxylic acid |
| 13 | 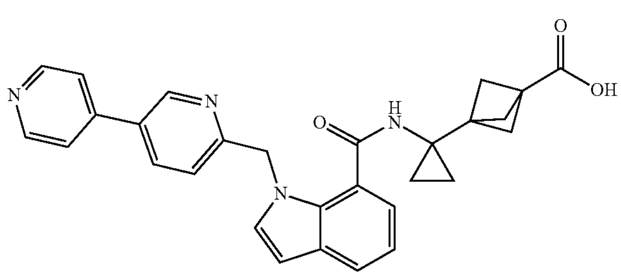 [SMILES: O=C(NC1(C23CC(C(=O)O)(C2)C3)CC1)c1cccc2ccn(Cc3ccc(-c4ccncc4)cn3)c12] | 3-(1-(1-([3,4'-Bipyridin]-6-ylmethyl)-1H-indole-7-carboxamido)cyclopropyl)bicyclo[1.1.1]pentane-1-carboxylic acid |

-continued

| Compound No. | Structure | Chemical name |
|---|---|---|
| 14 | 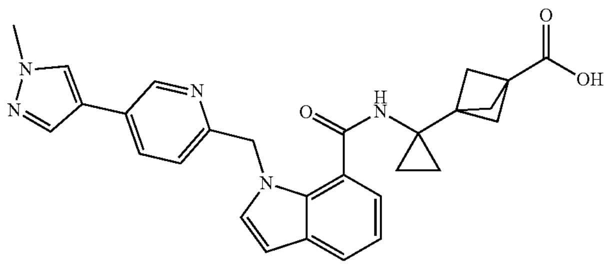 [SMILES: Cn1cc(-c2ccc(Cn3ccc4cccc(C(=O)NC5(C67CC(C(=O)O)(C6)C7)CC5)c43)nc2)cn1] | 3-(1-(1-((5-(1-Methyl-1H-pyrazol-4-yl)pyridin-2-yl)methyl)-1H-indole-7-carboxamido)cyclopropyl)bicyclo[1.1.1]pentane-1-carboxylic acid |
| 15 | 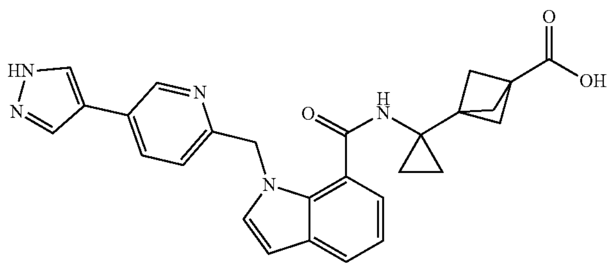 [SMILES: O=C(NC1(C23CC(C(=O)O)(C2)C3)CC1)c1cccc2ccn(Cc3ccc(-c4cn[nH]c4)cn3)c12] | 3-(1-(1-((5-(1H-Pyrazol-4-yl)pyridin-2-yl)methyl)-1H-indole-7-carboxamido)cyclopropyl)bicyclo[1.1.1]pentane-1-carboxylic acid |
| 16 | 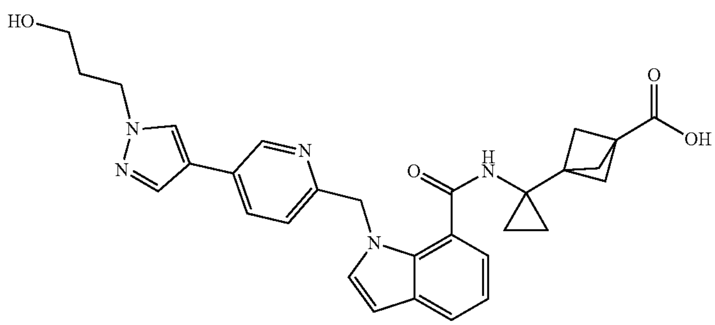 [SMILES: O=C(NC1(C23CC(C(=O)O)(C2)C3)CC1)c1cccc2ccn(Cc3ccc(-c4cnn(CCCO)c4)cn3)c12] | 3-(1-(1-((5-(1-(3-Hydroxypropyl)-1H-pyrazol-4-yl)pyridin-2-yl)methyl)-1H-indole-7-carboxamido)cyclopropyl)bicyclo[1.1.1]pentane-1-carboxylic acid |
| 17 | 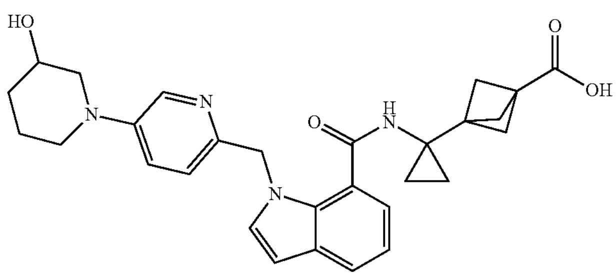 [SMILES: O=C(NC1(C23CC(C(=O)O)(C2)C3)CC1)c1cccc2ccn(Cc3ccc(N4CCCC(O)C4)cn3)c12] | 3-(1-(1-((5-(3-Hydroxypiperidin-1-yl)pyridin-2-yl)methyl)-1H-indole-7-carboxamido)cyclopropyl)bicyclo[1.1.1]pentane-1-carboxylic acid |
| 18 | 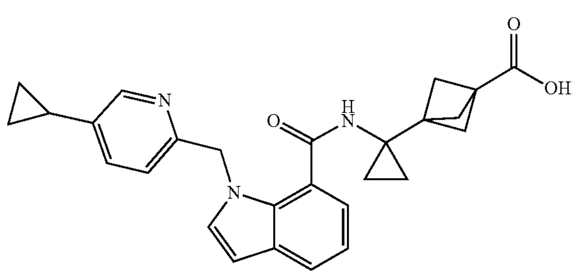 [SMILES: O=C(NC1(C23CC(C(=O)O)(C2)C3)CC1)c1cccc2ccn(Cc3ccc(C4CC4)cn3)c12] | 3-(1-(1-((5-Cyclopropylpyridin-2-yl)methyl)-1H-indole-7-carboxamido)cyclopropyl)bicyclo[1.1.1]pentane-1-carboxylic acid |

-continued

| Compound No. | Structure | Chemical name |
|---|---|---|
| 19 | 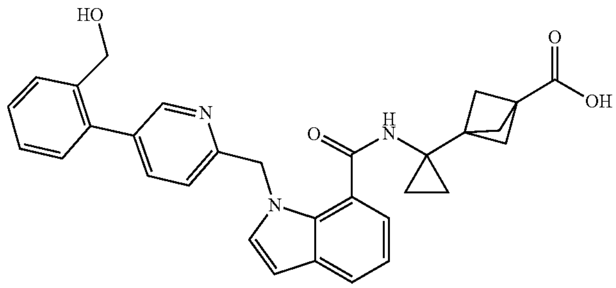 [SMILES: O=C(NC1(C23CC(C(=O)O)(C2)C3)CC1)c1cccc2ccn(Cc3ccc(-c4ccccc4CO)cn3)c12] | 3-(1-(1-((5-(2-(Hydroxymethyl)phenyl)pyridin-2-yl)methyl)-1H-indole-7-carboxamido)cyclopropyl)bicyclo[1.1.1]pentane-1-carboxylic acid |
| 20 | 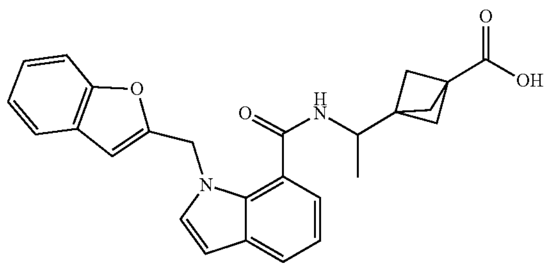 [SMILES: CC(NC(=O)c1cccc2ccn(Cc3cc4ccccc4o3)c12)C12CC(C(=O)O)(C1)C2] | 3-(1-(1-(Benzofuran-2-ylmethyl)-1H-indole-7-carboxamido)ethyl)bicyclo[1.1.1]pentane-1-carboxylic acid |
| 20-5 | 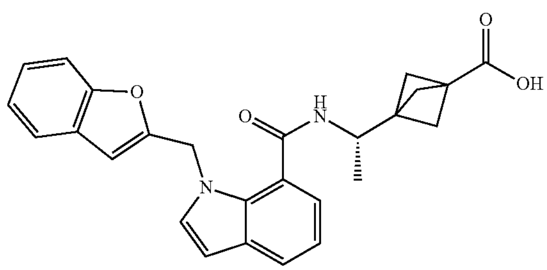 [SMILES: C[C@H](NC(=O)c1cccc2ccn(Cc3cc4ccccc4o3)c12)C12CC(C(=O)O)(C1)C2] | (S)-3-(1-(1-(Benzofuran-2-ylmethyl)-1H-indole-7-carboxamido)ethyl)bicyclo[1.1.1]pentane-1-carboxylic acid (the former component eluted in the chiral separation) |
| 20-6 | 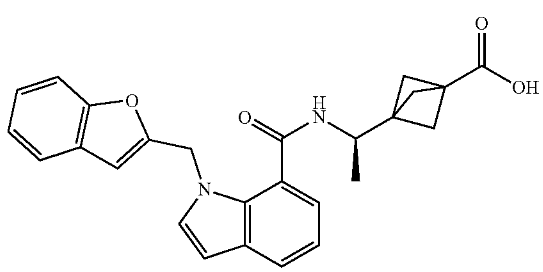 [SMILES: C[C@@H](NC(=O)c1cccc2ccn(Cc3cc4ccccc4o3)c12)C12CC(C(=O)O)(C1)C2] | (R)-3-(1-(1-(Benzofuran-2-ylmethyl)-1H-indole-7-carboxamido)ethyl)bicyclo[1.1.1]pentane-1-carboxylic acid (the latter component eluted in the chiral separation) |
| 21 | 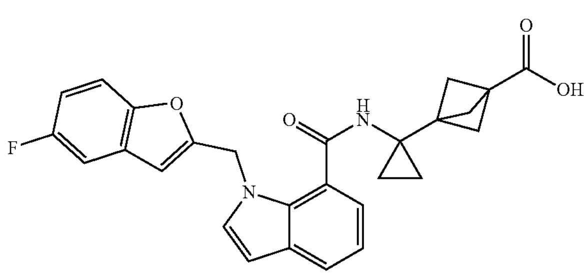 [SMILES: O=C(NC1(C23CC(C(=O)O)(C2)C3)CC1)c1cccc2ccn(Cc3cc4cc(F)ccc4o3)c12] | 3-(1-(1-((5-Fluorobenzofuran-2-yl)methyl)-1H-indole-7-carboxamido)cyclopropyl)bicyclo[1.1.1]pentane-1-carboxylic acid |

-continued

| Compound No. | Structure | Chemical name |
|---|---|---|
| 22 | 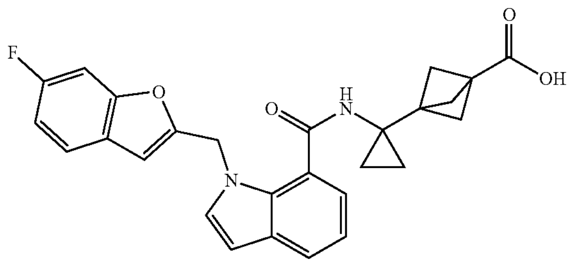 [SMILES: O=C(NC1(C23CC(C(=O)O)(C2)C3)CC1)c1cccc2ccn(Cc3cc4ccc(F)cc4o3)c12] | 3-(1-(1-((6-Fluorobenzofuran-2-yl)methyl)-1H-indole-7-carboxamido)cyclopropyl)bicyclo[1.1.1]pentane-1-carboxylic acid |
| 23 | 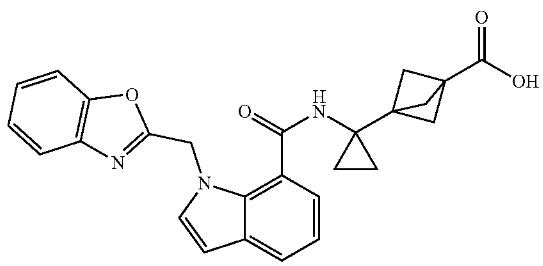 [SMILES: O=C(NC1(C23CC(C(=O)O)(C2)C3)CC1)c1cccc2ccn(Cc3nc4ccccc4o3)c12] | 3-(1-(1-(Benzo[d]oxazol-2-ylmethyl)-1H-indole-7-carboxamido)cyclopropyl)bicyclo[1.1.1]pentane-1-carboxylic acid |
| 24 | 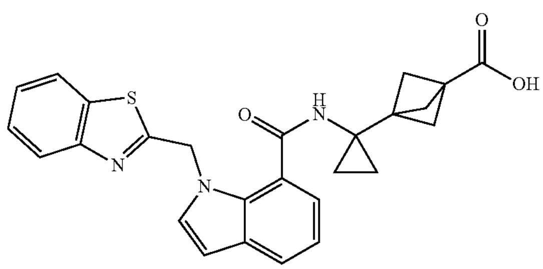 [SMILES: O=C(NC1(C23CC(C(=O)O)(C2)C3)CC1)c1cccc2ccn(Cc3nc4ccccc4s3)c12] | 3-(1-(1-(Benzo[d]thiazol-2-ylmethyl)-1H-indole-7-carboxamido)cyclopropyl)bicyclo[1.1.1]pentane-1-carboxylic acid |
| 25 | 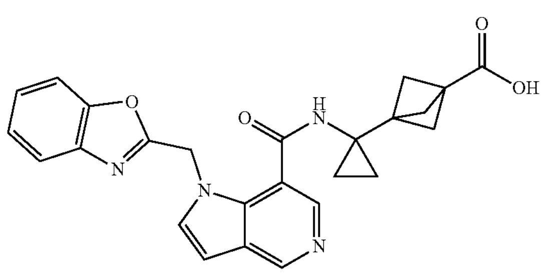 [SMILES: O=C(NC1(C23CC(C(=O)O)(C2)C3)CC1)c1cncc2ccn(Cc3nc4ccccc4o3)c12] | 3-(1-(1-(Benzofuran-2-ylmethyl)-1H-pyrrolo[3,2-c]pyridine-7-carboxamido)cyclopropyl)bicyclo[1.1.1]pentane-1-carboxylic acid |
| 26 | 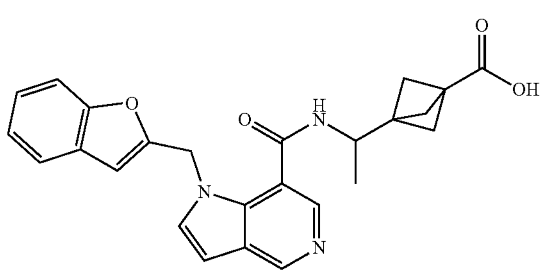 [SMILES: CC(NC(=O)c1cncc2ccn(Cc3cc4ccccc4o3)c12)C12CC(C(=O)O)(C1)C2] | 3-(1-(1-(Benzofuran-2-ylmethyl)-1H-pyrrolo[3,2-c]pyridine-7-carboxamido)ethyl)bicyclo[1.1.1]pentane-1-carboxylic acid |

-continued

| Compound No. | Structure | Chemical name |
|---|---|---|
| 26-1 | 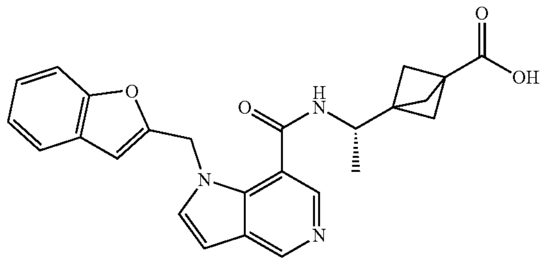 [SMILES: C[C@H](NC(=O)c1cncc2ccn(Cc3cc4ccccc4o3)c12)C12CC(C(=O)O)(C1)C2] | (S)-3-(1-(1-(Benzofuran-2-ylmethyl)-1H-pyrrolo[3,2-c]pyridine-7-carboxamido)ethyl)bicyclo[1.1.1]pentane-1-carboxylic acid (the former component eluted in the chiral separation) |
| 26-2 | 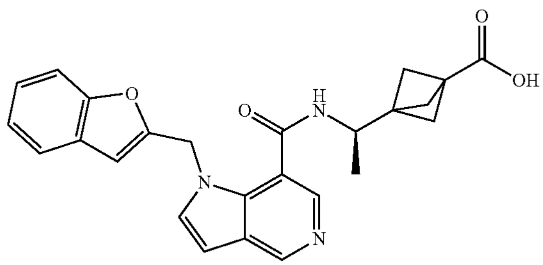 [SMILES: C[C@@H](NC(=O)c1cncc2ccn(Cc3cc4ccccc4o3)c12)C12CC(C(=O)O)(C1)C2] | (R)-3-(1-(1-(Benzofuran-2-ylmethyl)-1H-pyrrolo[3,2-c]pyridine-7-carboxamido)ethyl)bicyclo[1.1.1]pentane-1-carboxylic acid (the latter component eluted in the chiral separation) |
| 27 | 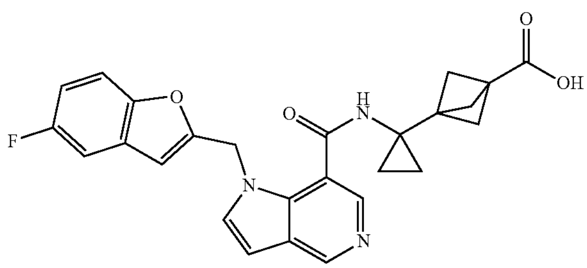 [SMILES: O=C(NC1(C23CC(C(=O)O)(C2)C3)CC1)c1cncc2ccn(Cc3cc4cc(F)ccc4o3)c12] | 3-(1-(1-((5-Fluorobenzofuran-2-yl)methyl)-1H-pyrrolo[3,2-c]pyridine-7-carboxamido)cyclopropyl)bicyclo[1.1.1]pentane-1-carboxylic acid |
| 28 | 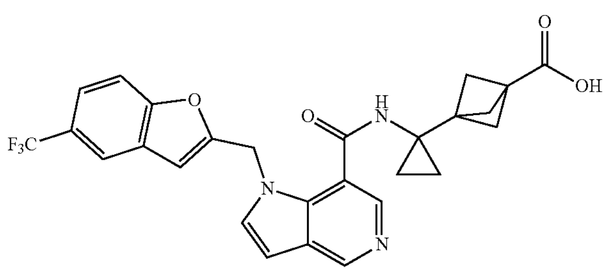 [SMILES: O=C(NC1(C23CC(C(=O)O)(C2)C3)CC1)c1cncc2ccn(Cc3cc4cc(C(F)(F)F)ccc4o3)c12] | 3-(1-(1-((5-(Trifluoromethyl)benzofuran-2-yl)methyl)-1H-pyrrolo[3,2-c]pyridine-7-carboxamido)cyclopropyl)bicyclo[1.1.1]pentane-1-carboxylic acid |
| 29 | 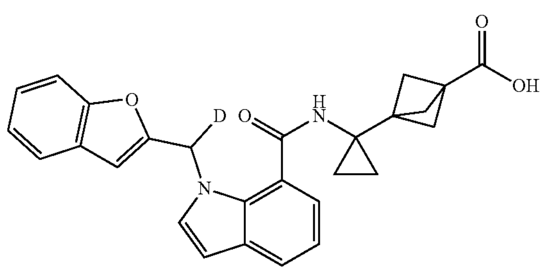 [SMILES: [2H]C(c1cc2ccccc2o1)n1ccc2cccc(C(=O)NC3(C45CC(C(=O)O)(C4)C5)CC3)c21] | 3-(1-(1-(Benzofuran-2-ylmethyl-d)-1H-indole-7-carboxamido)cyclopropyl)bicyclo[1.1.1]pentane-1-carboxylic acid |

| Compound No. | Structure | Chemical name |
|---|---|---|
| 30 | 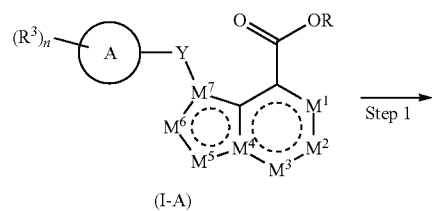 | 3-(1-(1-(1-Benzofuran-2-ylmethyl-d2)-1H-indole-7-carboxamido)cyclopropyl)bicyclo[1.1.1]pentane-1-carboxylic acid |
| 31 | 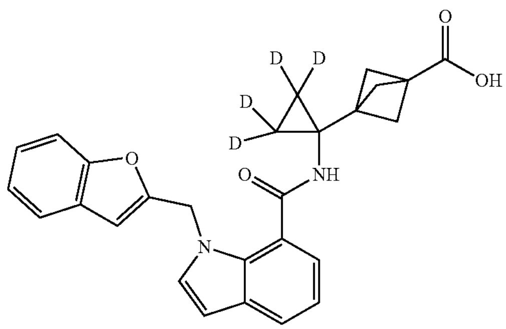 [SMILES: [2H]C1([2H])C([2H])([2H])C1(NC(=O)c1cccc2ccn(Cc3cc4ccccc4o3)c12)C12CC(C(=O)O)(C1)C2] | 3-(1-(1-(1-(Benzofuran-2-ylmethyl)-1H-indole-7-carboxamido)cyclopropyl-2,2,3,3-d4)bicyclo[1.1.1]pentane-1-carboxylic acid |
| 32 | | 3-(1-(1-(1-(Benzofuran-2-ylmethyl)-5-fluoro-1H-indole-7-carboxamido)cyclopropyl)bicyclo[1.1.1]pentane-1-carboxylic acid | or a tautomer, mesomer, racemate, enantiomer, diastereomer thereof, or mixture thereof, or a pharmaceutically acceptable salt thereof.

The compound of the present invention can be prepared by various methods known for preparing such a compound, for example, those as shown in the following reaction schemes. Unless otherwise stated in the reaction schemes and subsequent discussions, $M^t$ to $M^7$, ring A, X, Y, $R^1$, $R^2$, $R^3$ and n are as defined in formula (I).

The following reaction schemes illustrate the method for preparing the compound of formula (I).

Reaction scheme 1: A method for preparing the compound of formula (I)

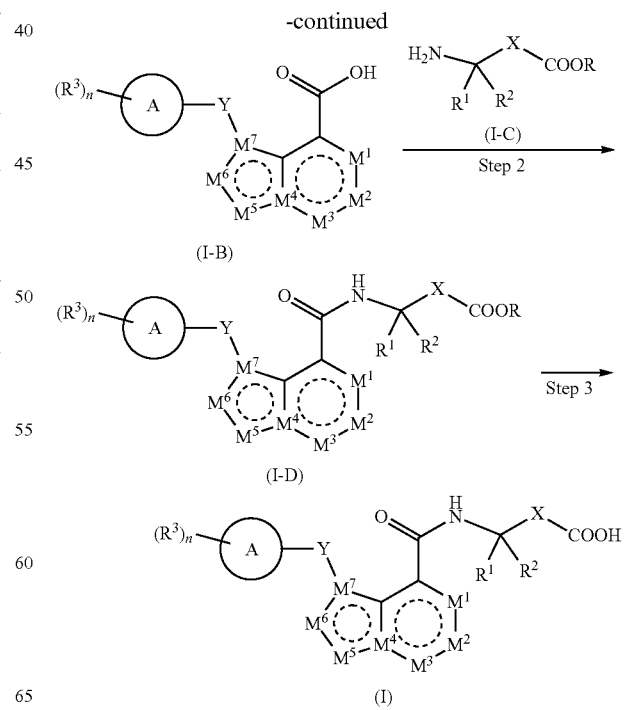

wherein:

Z=Cl, Br or I;

R is a $C_{1-4}$ alkyl, and preferably methyl.

Step 1

In this reaction step, a compound of formula (I-B) can be obtained by hydrolyzing a compound of formula (I-A) in a solvent under an alkaline condition. The hydrolysis reaction can be carried out under a conventional condition: in a typical situation, the reaction is carried out under an alkaline condition, for example in the presence of sodium hydroxide, potassium hydroxide or lithium hydroxide. The selected solvent includes methanol, ethanol, propanol, butanol, 2-methoxyethane, 1,4-dioxane, ethylene glycol, tetrahydrofuran and 1,2-dimethoxyethane. The reaction temperature can be 0 to 100° C., usually 20° C. to 60° C., and the reaction duration is 60 minutes to 10 hours.

Step 2

The compound of formula (I-B) and a compound of formula (I-C) is subjected to a condensation reaction in an inert solvent in the presence of a condensing agent to obtain a compound of formula (I-D). Preferably, the condensing agent is selected from the group consisting of 2-(7-azabenzotriazol-1-yl)-N,N,N',N'-tetramethyluronium hexafluorophosphate (HATU), 1-ethyl-3-(3-dimethylaminopropyl)carbodiimide (EDCI), 1-(3-dimethylaminopropyl)-3-ethylcarbodiimide hydrochloride, N,N'-dicyclohexylcarbodiimide, N,N'-diisopropylcarbodiimide, O-(benzotriazol-1-yl)-N,N,N',N'-tetramethyluronium tetrafluoroborate, 1-hydroxybenzotriazole, 1-hydroxy-7-azobenzotriazole, O-(benzotriazol-1-yl)-N,N,N',N'-tetramethyluronium hexafluorophosphate, 2-(7-azobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinophosphonium hexafluorophosphate, and most preferably 2-(7-azabenzotriazol-1-yl)-N,N,N',N'-tetramethyluronium hexafluorophosphate (HATU) and 1-ethyl-3-(3-dimethylaminopropyl)carbodiimide (EDCI). The inert solvent is selected from the group consisting of dimethylformamide, dimethylacetamide, N-methylpyrrolidone, dimethyl sulfoxide, tetrahydrofuran, dimethoxyethane or a mixture thereof. The reaction temperature can be 0 to 50° C., and the reaction duration is 10 hours to 24 hours.

Step 3

In this reaction step, the compound of formula (I) can be obtained by hydrolyzing the compound of formula (I-D) in a solvent under an alkaline condition. The reaction condition is the same as in step 2.

Reaction scheme 2: Method I for preparing the intermediate compound of formula (I-A)

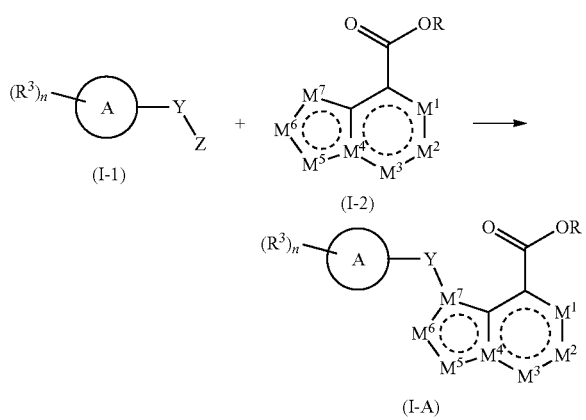

wherein:

Z=Cl, Br or I;

R is a $C_{1-4}$ alkyl, and preferably methyl.

In this reaction step, a compound of formula (I-1) and a compound of formula (I-2) are reacted in an inert solvent in the presence of an alkali to obtain the compound of formula (I-A). Preferably, the alkali is selected from the group consisting of potassium tert-butoxide, sodium tert-butoxide, lithium tert-butoxide, sodium hydride, potassium hydride, sodium ethoxide and potassium ethoxide; and the inert solvent is selected from the group consisting of dimethylformamide, dimethylacetamide, N-methylpyrrolidone, dimethyl sulfoxide, tetrahydrofuran, dimethoxyethane or a mixture thereof. The reaction temperature can be 0 to 100° C., usually 20° C. to 60° C., and the reaction duration is 60 minutes to 10 hours.

Reaction scheme 3: Method II for preparing the intermediate compound of formula (I-A)

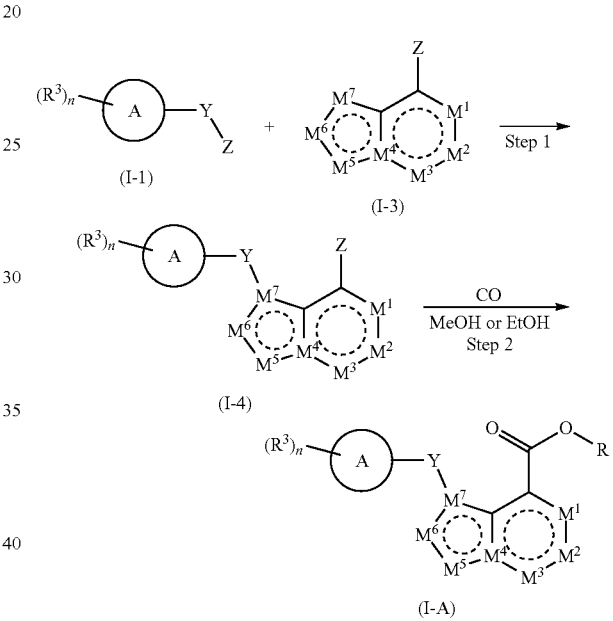

wherein:

Z=Cl, Br or I;

R is a $C_{1-4}$ alkyl, and preferably methyl.

Step 1

In this reaction step, a compound of formula (I-1) is reacted with a compound of formula (I-3) in an inert solvent in the presence of an alkali to obtain a compound of formula (I-4). The reaction condition is the same as in step 1A.

Step 2

In this reaction step, the compound of formula (I-4) is reacted with carbon oxide in methanol or ethanol in the presence of a palladium catalyst, ligand and organic alkali to obtain the compound of formula (I-A). Preferably, the palladium catalyst is selected from the group consisting of palladium acetate, palladium (II) acetylacetonate, palladium (II) propionate, tetrakis(triphenylphosphine)palladium, [1,2-bis(dicyclohexylphosphino)ethane]palladium (II) chloride and bis(dicyclohexylphosphino)palladium (0), and the ligand is selected from the group consisting of triphenylphosphine, 1,2-bis(diphenylphosphino)ethane, di-tert-butylneopentylphosphine, bis(2-diphenylphosphinoethyl)phenylphosphine, 1,2-bis(dicyclohexylphosphino)ethane, tBuBrettPhos and ((2,4,6-triisopropyl)phenyl)dicyclohexylphosphine. The reaction temperature can be 60 to 120° C., and the reaction duration is 24 hours to 48 hours.

The present invention also relates to a pharmaceutical composition comprising a therapeutically effective amount of the compound of formula (I), or the tautomer, mesomer, racemate, enantiomer, diastereomer thereof, or mixture thereof, or the pharmaceutically acceptable salt thereof, and pharmaceutically acceptable carrier(s), diluent(s) or excipient(s).

The present invention also relates to a use of the compound of formula (I) or the pharmaceutical composition comprising the same in the preparation of a medicament for inhibiting PGE2/EP4 signaling transduction.

The present invention also relates to a use of the compound of formula (I) or the pharmaceutical composition comprising the same in the preparation of a medicament for treating cancer, wherein the cancer is preferably selected from the group consisting of breast cancer, cervical cancer, colorectal cancer, endometrial cancer, glioblastoma, head and neck cancer, kidney cancer, liver cancer, lung cancer, medulloblastoma, ovarian cancer, pancreatic cancer, prostate cancer, skin cancer and urethral cancer.

The present invention also relates to a use of the compound of formula (I) or the pharmaceutical composition comprising the same in the preparation of a medicament for treating acute or chronic pain, migraine, osteoarthritis, rheumatoid arthritis, gout, bursitis, ankylosing spondylitis, primary dysmenorrhea, cancer or arteriosclerosis.

The present invention also relates to the compound of formula (I), or the tautomer, mesomer, racemate, enantiomer, diastereomer thereof, or mixture thereof, or the pharmaceutically acceptable salt thereof, or the pharmaceutical composition comprising the same, for use as a medicament.

The present invention also relates to the compound of formula (I), or the tautomer, mesomer, racemate, enantiomer, diastereomer thereof, or mixture thereof, or the pharmaceutically acceptable salt thereof, or the pharmaceutical composition comprising the same, for use in inhibiting PGE2/EP4 signaling transduction.

The present invention also relates to the compound of formula (I), or the tautomer, mesomer, racemate, enantiomer, diastereomer thereof, or mixture thereof, or the pharmaceutically acceptable salt thereof, or the pharmaceutical composition comprising the same, for use in treating cancer, wherein the cancer is preferably selected from the group consisting of breast cancer, cervical cancer, colorectal cancer, endometrial cancer, glioblastoma, head and neck cancer, kidney cancer, liver cancer, lung cancer, medulloblastoma, ovarian cancer, pancreatic cancer, prostate cancer, skin cancer and urethral cancer.

The present invention also relates to the compound of formula (I), or the tautomer, mesomer, racemate, enantiomer, diastereomer thereof, or mixture thereof, or the pharmaceutically acceptable salt thereof, or the pharmaceutical composition comprising the same, for use in treating acute or chronic pain, migraine, osteoarthritis, rheumatoid arthritis, gout, bursitis, ankylosing spondylitis, primary dysmenorrhea, cancer or arteriosclerosis.

A method for inhibiting PGE2/EP4 signaling transduction, comprising a step of administrating to a patient in need thereof a therapeutically effective dose of the compound of formula (I), or the tautomer, mesomer, racemate, enantiomer, diastereomer thereof, or mixture thereof, or the pharmaceutically acceptable salt thereof, or the pharmaceutical composition comprising the same.

A method for treating cancer, comprising a step of administrating to a patient in need thereof a therapeutically effective dose of the compound of formula (I), or the tautomer, mesomer, racemate, enantiomer, diastereomer thereof, or mixture thereof, or the pharmaceutically acceptable salt thereof, or the pharmaceutical composition comprising the same, wherein the cancer is preferably selected from the group consisting of breast cancer, cervical cancer, colorectal cancer, endometrial cancer, glioblastoma, head and neck cancer, kidney cancer, liver cancer, lung cancer, medulloblastoma, ovarian cancer, pancreatic cancer, prostate cancer, skin cancer and urethral cancer.

A method for treating acute or chronic pain, migraine, osteoarthritis, rheumatoid arthritis, gout, bursitis, ankylosing spondylitis, primary dysmenorrhea, cancer or arteriosclerosis, comprising a step of administrating to a patient in need thereof a therapeutically effective dose of the compound of formula (I), or the tautomer, mesomer, racemate, enantiomer, diastereomer thereof, or mixture thereof, or the pharmaceutically acceptable salt thereof, or the pharmaceutical composition comprising the same.

The compound and antibody according to the present invention can be administered orally, sublingually, intraperitoneally, parenterally, subcutaneously, intramuscularly, intravenously, transdermally, locally or rectally.

In the pharmaceutical compound of the present invention, for oral, sublingual, parenteral, subcutaneous, intramuscular, intravenous, transdermal, local or rectal administration, the active ingredient can be mixed with a conventional pharmaceutical carrier, and administered to animal or human in unit forms of administration. Suitable unit forms of administration include oral forms such as tablets, gel capsules, powders, granules and oral solutions or suspensions, sublingual or buccal forms for administration, parenteral, subcutaneous, intramuscular, intravenous, intranasal or intraocular forms of administration and rectal forms of administration.

When a solid composition is prepared into the form of tablets, the principal active ingredient is mixed with a pharmaceutical carrier such as gelatin, starch, lactose, magnesium stearate, talc, gum arabic and the like. The tablets can be coated with sucrose or other suitable materials, or else treated in such a way that they have an extended or delayed activity and continuously releases a predetermined amount of active ingredient.

A gel capsule preparation can be obtained by mixing the active ingredient with a diluent followed by pouring the resulting mixture into soft or hard capsules.

A preparation in the form of a syrup or elixir can comprise the active ingredient in combination with a sweetening agent, preservative, as well as a flavour-producing agent and appropriate colorant.

Powders or granules dispersible in water can comprise the active ingredient mixed together with dispersing agents, wetting agents, or suspending agents, as well as taste correctors or sweetening agents.

Suppository is used for rectal administration, which is prepared with binding agents melting at rectal temperature such as cocoa butter or polyethylene glycols.

Aqueous suspension, isotonic saline solution or sterile injectable solution (comprising pharmacologically compatible dispersing agents and/or wetting agents) is used for parenteral, intranasal or intraocular administration.

The active ingredient can also be formulated as microcapsules, possibly with one or more additive carriers.

The compound of the present invention can be administered at a dose between 0.01 mg and 1000 mg per day, and adminstered in a single dose per day or in several doses throughout the day, for example, twice a day in equal doses. The daily dose administered is advantageously between 0.1 mg and 1000 mg, and even more advantageously between 2.5 mg and 200 mg. It may be necessary to administer doses exceeding these ranges, of which those skilled in the art will themselves be aware.

In a particular embodiment of the present invention, the pharmaceutical composition can also be formulated for topical administration. It can be introduced in forms commonly known for this type of administration (i.e., especially lotion, foam, gel, dispersion, spray), and such forms comprise excipients that particularly enable penetration of the skin so as to improve the properties and accessibility of the active ingredient. Besides the composition according to the present invention, these compositions typically further comprise a physiologically acceptable medium, which generally contains water or a solvent such as an alcohol, ether or ethylene glycol. The composition can also comprise surfactants, preservatives, stabilizers, emulsifiers, thickeners, other active ingredients producing a complementary effect or a possibly synergistic effect, trace elements, essential oils, perfumes, colorants, collagen, chemical or mineral filters.

Definitions

Unless otherwise stated, the terms used in the specification and claims have the meanings described below.

Within the meaning of the present invention, the term "stereoisomer" refers to a geometric isomer (or configuration isomer) or optical isomer.

"Geometric isomer" results from different position of the substituents on a double bond which can then have a Z or E configuration, also called cis or trans configuration.

"Optical isomer" results in particular from the different spatial position of the substituents on a carbon atom comprising four different substituents. This carbon atom then constitutes a chiral center or asymmetric center. Optical isomers include diastereomers and enantiomers. Optical isomers that are non-superimposable mirror images of each other are called "enantiomers". Optical isomers that are not superimposable mirror images of each other are called "diastereomers".

A mixture containing equal amounts of two individual enantiomeric forms of opposite chirality is called a "racemic mixture".

Within the meaning of the present invention, the term "tautomer" refers to a constitutional isomer of the compound obtained by prototropie (i.e. by migration of a hydrogen atom and change of location of a double bond). The different tautomers of a compound are generally interconvertible and present in equilibrium in solution, in proportions that can vary depending on the solvent used, the temperature or the pH.

In the present invention, "pharmaceutically acceptable" is understood to mean that which is useful in the preparation of a pharmaceutical composition which is generally safe, non-toxic, and neither biologically nor otherwise undesirable and which is acceptable for veterinary and human pharmaceutical use.

In the present invention, the "pharmaceutically acceptable salt" of a compound is understood to refer to salts, which are pharmaceutically acceptable, as defined herein, and which possess the desired pharmacological activity of the parent compound. Such salts include:

(1) acid addition salts formed with inorganic acids such as hydrochloric acid, hydrobromic acid, sulfuric acid, nitric acid, phosphoric acid and the like; or acid addition salts formed with organic acids such as acetic acid, benzenesulfonic acid, benzoic acid, camphorsulfonic acid, citric acid, ethylsulfonic acid, fumaric acid, glucoheptonic acid, gluconic acid, glutamic acid, glycolic acid, hydroxynaphtoic acid, 2-hydroxylethylsulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like; and (2) salts formed when an acidic proton present in parent compound is either replaced by a metal ion such as an alkali metal ion (e.g., $Na^+$, $K^+$ or $Li^+$), an alkaline earth metal ion (e.g. $Ca^{2+}$ or $Mg^{2+}$), or an aluminum ion; or coordinates with an organic base or inorganic base. Acceptable organic bases include diethanolamine, ethanolamine, N-methylglucamine, triethanolamine, tromethamine and the like. Acceptable inorganic bases include aluminum hydroxide, calcium hydroxide, potassium hydroxide, sodium carbonate and sodium hydroxide.

In the present invention, the term "halogen" refers to fluorine, bromine, chlorine or iodine atom.

The term "$C_{1-4}$ alkyl" refers to a saturated, linear or branched hydrocarbon chain comprising 1 to 4 carbon atoms. Representative examples include, but are not limited to methyl, ethyl, n-propyl, isopropyl, n-butyl, iso-butyl, sec-butyl, tert-butyl groups.

The term "$C_{1-4}$ alkylene" refers to a divalent hydrocarbon chain comprising 1 to 4 carbon atoms. Representative examples include, but are not limited to —$CH_2$—, —$CH_2$—$CH_2$—, —$CH_2$—$CH_2$—$CH_2$—, —$CH_2$—$CH_2$—$CH_2$—$CH_2$— and the like.

The term "$C_{1-4}$ alkoxy" refers to an —O—($C_{1-4}$ alkyl) group, wherein the $C_{1-4}$ alkyl is as defined above. Non-limiting examples include methoxy, ethoxy, propyloxy, butoxy and the like.

The term "halo$C_{1-4}$ alkyl" refers to a $C_{1-4}$ alkyl group substituted by one or more halogens, wherein the $C_{1-4}$ alkyl and halogen are as defined above.

The term "halo$C_{1-4}$ alkoxy" refers to a $C_{1-4}$ alkoxy group substituted by one or more halogens, wherein the $C_{1-4}$ alkoxy and halogen are as defined above.

The term "hydroxy$C_{1-4}$ alkyl" refers to a $C_{1-4}$ alkyl group substituted by hydroxy(s), wherein the alkyl is as defined above.

The term "$C_{3-6}$ cycloalkyl" refers to a saturated or partially unsaturated monocyclic hydrocarbon system having 3 to 6 carbon atoms. Representative examples include, but are not limited to cyclohexyl, cyclopentyl, cyclobutyl, cyclopropyl, cyclohexenyl and the like.

The term "3 to 6 membered heterocyclyl" refers to a saturated or partially unsaturated monocyclic hydrocarbon system having 3 to 6 ring atoms, wherein 1 to 3 ring atoms are heteroatoms selected from the group consisting of N, O and $S(O)_m$ (wherein m is 0, 1 or 2). Representative examples include, but are not limited to pyrrolidinyl, imidazolyl, tetrahydrofuranyl, tetrahydropyranyl, tetrahydrothienyl, dihydroimidazolyl, dihydrofuranyl, dihydropyrazolyl, dihydropyrrolyl, piperidinyl, piperazinyl, morpholinyl and the like.

The term "$C_{6-10}$ aryl" refers to a 6 to 10 membered all-carbon monocyclic ring or polycyclic fused ring (i.e. each ring in the system shares an adjacent pair of carbon atoms with another ring in the system) having a conjugated π-electron system, for example, phenyl and naphthyl, more preferably a phenyl. The aryl ring can be fused to the ring of heteroaryl, heterocyclyl or cycloalkyl, wherein the ring bound to the parent structure is the aryl ring. Non-limiting examples thereof include:

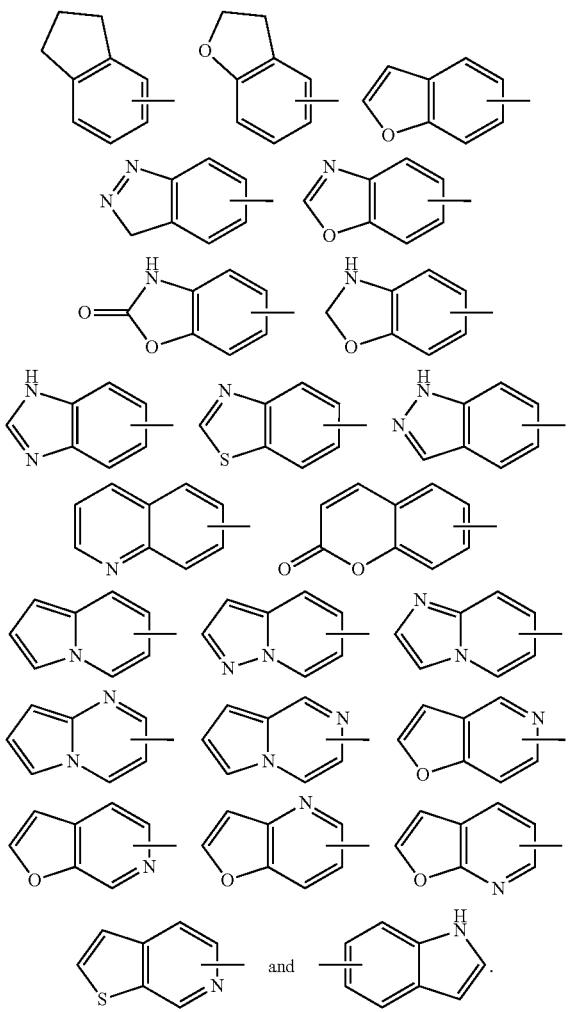

The term "5 to 10 membered heteroaryl" refers to a 5 to 10 membered heteroaromatic system having 1 to 4 heteroatoms selected from the group consisting of oxygen, sulfur and nitrogen. The 5 to 10 membered heteroaryl is preferably a 5 or 6 membered heteroaryl having 1 to 2 heteroatoms, for example quinolinyl, imidazolyl, furyl, thienyl, thiazolyl, pyrazolyl, oxazolyl, isoxazolyl, pyrrolyl, tetrazolyl, pyridyl, pyrimidinyl, thiadiazole, pyrazinyl and the like. The heteroaryl ring can be fused to the ring of aryl, heterocyclyl or cycloalkyl, wherein the ring bound to the parent structure is the heteroaryl ring. Non-limiting examples thereof include:

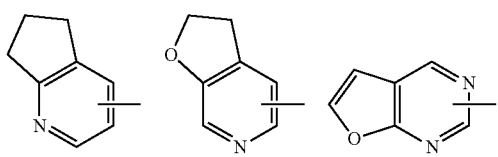

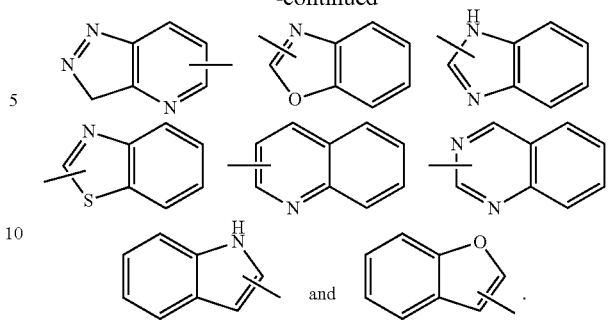

The term "hydroxy" refers to an —OH group.
The term "nitro" refers to a —NO$_2$ group.
The term "amino" refers to a —NH$_2$ group.
The term "cyano" refers to a —CN group.
The term "a bond" refers to a covalent bond represented by "—".

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without excessive effort. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

The term "antibody" as used herein includes all types of immunoglobulins, including IgG, IgM, IgA, IgD and IgE, or fragments thereof, which can be applied to the medicine used herein. The antibody can be a monoclonal antibody or a polyclonal antibody, and can be from a species of any origin, including, for example, mouse, rat, rabbit, horse or human. Antibody fragments that retain the specificity for protein or epitope such as CTLA4, PDL1 or PD1, which are combined with the antibodies used in the present invention, are also included in the scope of the term "antibody". These fragments can be produced by known techniques. The antibody can be chimeric or humanized, especially when it is used for therapeutic purposes.

The term "CTLA4 antibody" or "anti-CTLA4" refers to an antibody against cytotoxic T-lymphocyte antigen 4 (CTLA4). Exemplary antibodies include but are not limited to CTLA4 antagonist antibodies or CTLA4 antibodies, such as Ipilimumab (Bristol-Myers Squibb) and Tremelimumab (Pfizer).

The term "PDL1 antibody" or "anti-PDL1" refers to an antibody against programmed death ligand 1 (PDL1). Exemplary antibodies include but are not limited to Atezolizumab (Roche), Durvlumab (AstraZeneca), BMS-936559, CK-301 (Check Point Therapeutics), KN035 (Alphamab Oncology), BGB-A333 (BeiGene), CS1001 (Cstone Pharmaceuticals), HLX20 (Henlius Biotech), KL-A167 (Kelun Biotech), F520 (New Era Pharmaceutical), GR1405 (Zhixiang Jintai), and MSB2311 (MabSpace).

The term "PD1 antibody" or "anti-PD1" refers to an antibody against programmed death protein 1 (PD1). Exemplary antibodies include but are not limited to nivolumab (Bristol-Myers Squibb), labrolizumab (Merck), pembrolizumab (Merck Sharp & Dohme), Avelumab (Merck/Pfizer), Pidilizumab (Medivation), AMP-224, AMP-514 (GlaxoSmithKline), Spartalizumab (Novartis), Cemiplimab (Trade name Libtayo, Sanofi/Regeneron), Toripalimab (Junshi), Sintilimab (Innovent), Camrelizumab (Hengrui), Tislelizumab (BeiGene), GLS-010 (Gloria Pharmaceuticals), GB226 (Genor Biopharma), CS1003 (Cstone Pharmaceuticals), BAT-1306 (Bio-Thera), HX008 (Hanzhong/Hansi/Akeso), AK105 (Akeso), LZM009 (Livzon Pharm), HLX10 (Henlius Biotech).

DETAILED DESCRIPTION OF THE INVENTION

Figure 1:
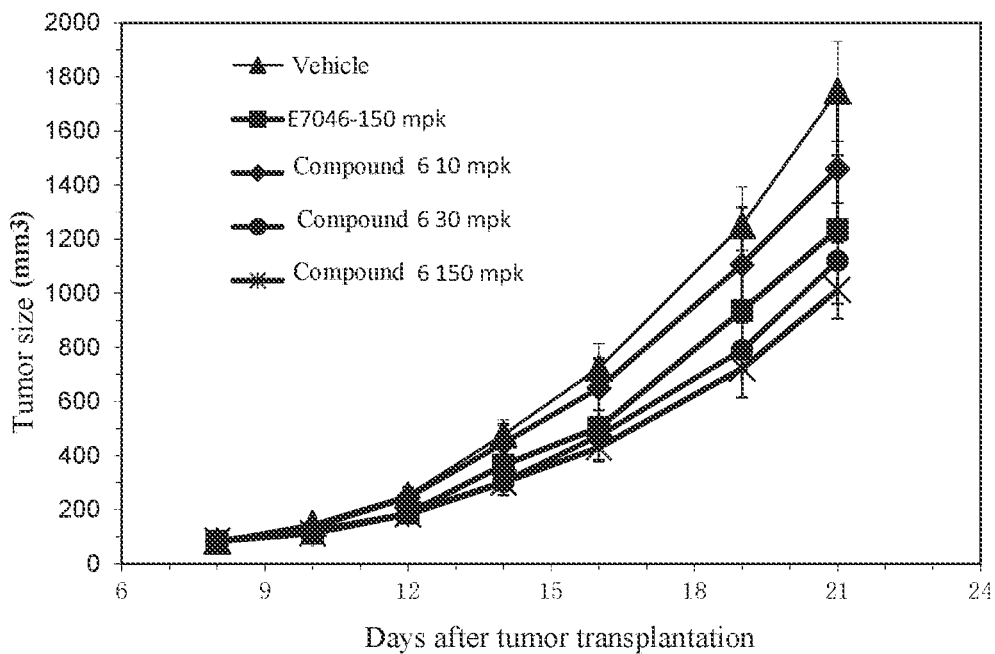
FIG. 1 shows the effect of different doses of compound 6 and E7046 on tumor growth in CT-26 colorectal cancer model.

By reading the following examples, the person skilled in the art will better understand the present invention. The following examples merely serve to illuminate the present invention.

In the examples of the present invention, the experiment methods that do not specify the specific conditions are generally conducted in accordance with conventional conditions, or in accordance with conditions recommended by the material or product manufacturers. The reagents without a specific source are commercially available conventional reagents.

The structures of the compounds were identified by nuclear magnetic resonance (NMR) and/or mass spectrometry (MS). NMR shifts (δ) are given in $10^{-6}$ (ppm). The solvent for determination was deuterated-chloroform ($CDCl_3$), deuterated dimethyl sulfoxide (DMSO-$d_6$), deuterated methanol ($CD_3OD$) or deuterated acetonitrile ($CD_3CN$). The internal standard was tetramethylsilane (TMS). The following abbreviations are used: s for singlet, bs for broad singlet, d for doublet, t for triplet, q for quartet, m for multiplet or massive, dd for double of doublet, etc.

Liquid chromatograph-mass spectrometer: SHIMADZU LCMS-2020, column: Kinetex® 5 m×30×2.1 mm S/N: H17-247175, column temperature: 50.0° C., mobile phase: A: water (0.0375% TFA), B: acetonitrile (0.01875% TFA), ionization mode: ESI, polarity: positive.

| Gradient elution | | |
|---|---|---|
| Time (minutes) | B (%) | Flow rate (mL/min) |
| 0.0 | 5 | 1.5 |
| 0.80 | 95 | 1.5 |
| 1.20 | 95 | 1.5 |
| 1.21 | 5 | 1.5 |
| 1.55 | 5 | 1.5 |

Nuclear magnetic resonance spectrometer: Bruker ARX-500 high resolution mass spectrometer and Bruker ARX-400 high resolution mass spectrometer.

MTT detection instrument: Thermo Scientific Multiskan GO full-wavelength microplate reader.

Qingdao GF254 silica gel plate is used as the thin-layer silica gel chromatography (TLC) plate. The dimension of the silica gel plate used in TLC is 0.15 mm to 0.2 mm, and the dimension of the silica gel plate used in product purification is 0.4 mm to 0.5 mm.

Yantai Huanghai 200 to 300 mesh silica gel is generally used as a carrier for column chromatography.

Unless otherwise stated, the reactions were carried out under argon atmosphere or nitrogen atmosphere.

Unless otherwise stated, the solution in the reaction refers to an aqueous solution.

Unless otherwise stated, the reaction temperature is room temperature.

The reaction process in the examples was monitored by thin layer chromatography (TLC).

Common Abbreviations

EP4: Prostaglandin E2 receptor 4
PGE2: Prostaglandin E2
COX: Cyclooxygenase
cAMP: Cyclic adenosine monophosphate
PKA: Protein kinase A
PI3K: Phosphatidylinositol 3 kinase
ERK: Extracellular regulated kinase
NSAIDs: Non-steroidal anti-inflammatory drugs
TNF-α: Tumor necrosis factor alpha
IL-12: Interleukin 12
NMR: Nuclear magnetic resonance
MS: Mass spectrometry
DMSO: Dimethyl sulfoxide
DMF: Dimethylformamide
TLC: Thin layer chromatography
HATU: 1-[Bis(dimethylamino)methylene]-1H-1,2,3-triazolo[4,5-b]pyridinium 3-oxide hexafluorophosphate
DIPEA: Diisopropylethylamine
LCMS: Liquid chromatography-mass spectrometry
HPLC: High performance liquid chromatography Rt: Retention time
DME: Dimethoxyethane
NBS: N-bromosuccinimide
AIBN: Azobisisobutyronitrile
DCM: Dichloromethane
Dppf: 1,1'-Bis(diphenylphosphino)ferrocene
TEA: Triethylamine
CDI: Carbonyldiimidazole
TFAA: Trifluoroacetic anhydride
BPO: Benzoyl peroxide
THF: Tetrahydrofuran
Xphos: 2-Dicyclohexylphosphino-2',4',6'-triisopropylbiphenyl
tBuBrettPhos: 2-(Di-tert-butylphosphino)-2',4',6'-triisopropyl-3,6-dimethoxy-1,1'-biphenyl
FDD: First dose double

Example 1

3-(1-(1-(4-(Trifluoromethyl)benzyl)-1H-indole-7-carboxamido)cyclopropyl)bicyclo[1.1.1]pentane-1-carboxylic acid 1

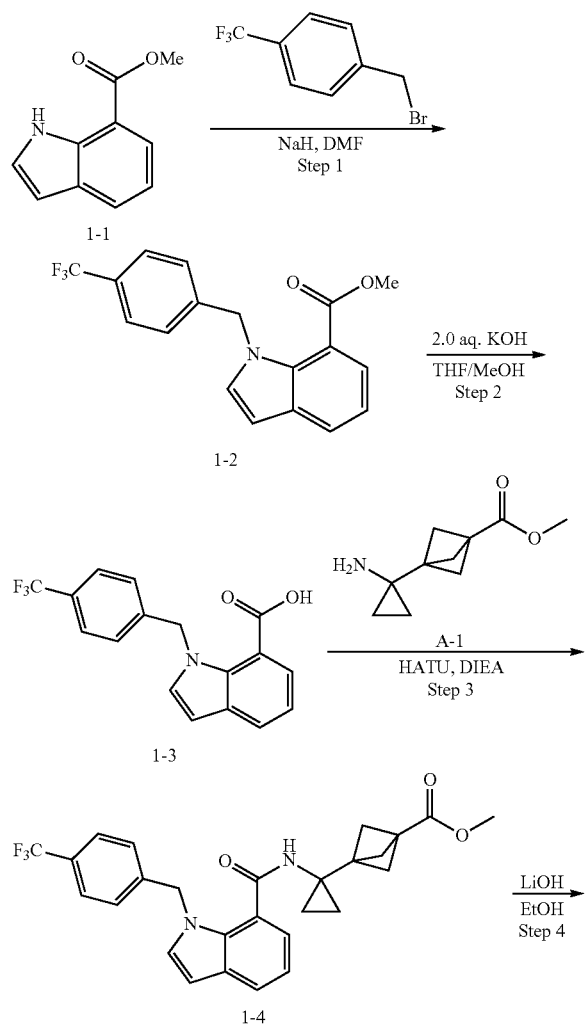

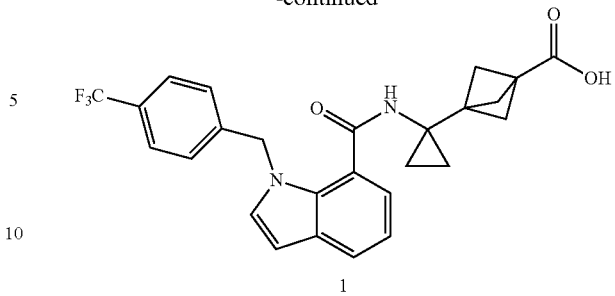

Step 1: Preparation of methyl 1-(4-(trifluoromethyl)benzyl)-1H-indole-7-carboxylate 1-2

Methyl 1H-indole-7-carboxylate 1-1 (5.00 g, 28.5 mmol) and 1-(bromomethyl)-4-(trifluoromethyl)benzene (7.75 g, 32.4 mmol, 5 mL) were dissolved in DMF (130 mL), followed by the slow addition of NaH (1.26 g, 31.3 mmol, purity: 60%) in an ice bath. The resulting mixture was stirred for 3 hours, followed by removing the ice bath. The resulting mixture was stirred at 20° C. for 6 hours. TLC (petroleum ether/ethyl acetate=5/1) showed that the raw material (Rf=0.40) was consumed completely, and a new major point was formed (Rf=0.5). The reaction mixture was then quenched with saturated aqueous $NH_4Cl$ solution (100 mL), and then extracted with ethyl acetate (100 mL). The organic layer was washed with brine (200 mL), dried over anhydrous sodium sulfate, filtered and concentrated. The resulting residue was purified by flash silica gel chromatography (ISCO®; 20 g SepaFlash® silica gel column, 0~3% ethyl acetate/petroleum ether gradient eluent) to obtain compound 1-2 (6.50 g, 18.7 mmol, yield: 65.5%) as a yellow solid. MS (ESI): 334.1 $[M+1]^+$.

Step 2: Preparation of 1-(4-(trifluoromethyl)benzyl)-1H-indole-7-carboxylic acid 1-3

Aqueous KOH solution (2 M, 45 mL) was added to a solution of compound 1-2 (3.00 g, 9.00 mmol) in methanol (45 mL) and tetrahydrofuran (45 mL). The resulting mixture was stirred at 25° C. for 12 hours. LCMS showed that the starting material was consumed completely, and a molecular weight peak of the desired product was detected (Rt=0.948 min). The reaction mixture was then concentrated at 45° C. to remove most of the methanol and tetrahydrofuran, acidified with 1 N aqueous hydrochloric acid to pH~6-7, washed with 1 N hydrochloric acid and extracted with ethyl acetate (100 mL). The organic layer was dried over anhydrous sodium sulfate, filtered and concentrated to obtain compound 1-3 (2.20 g, 6.89 mmol, yield: 76.5%) as a yellow solid. MS (ESI): 320.1 $[M+1]^+$.

General method for preparing methyl 3-(1-aminocyclopropyl)bicyclo[1.1.1]pentane-1-carboxylate A-1

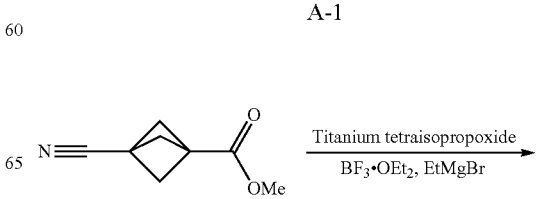

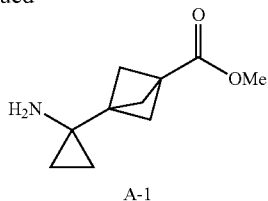

A-1

Titanium tetraisopropoxide (29.8 g, 99.7 mmol, 31 mL, purity: 95%) was added to a solution of methyl 3-cyanobicyclo[1.1.1]pentane-1-carboxylate (22.5 g, 99.2 mmol) in toluene (240 mL) under a nitrogen atmosphere at −20° C. EtMgBr (3 M, 60 mL) was added dropwise within 30 minutes under a nitrogen atmosphere at −20° C., and the temperature was kept between −20~−10° C. After stirring for 30 minutes, BF$_3$·Et$_2$O (27.6 g, 194 mmol, 24 mL) was added dropwise. The reaction mixture was stirred at −20° C. for 30 minutes and then at 25° C. for 12 hours. TLC (plate 1: petroleum ether/ethyl acetate=3/1) showed that the raw material (Rf=0.61) was consumed completely, and TLC (plate 2: petroleum ether/ethyl acetate=1/1) showed that a major product (Rf=0.24) was formed. The reaction mixture was quenched by slowly adding aqueous hydrochloric acid (1 N, 30 mL) at 0° C., and then the separated organic layer was discarded. The aqueous phase was basified to pH~12 with 10 M aqueous sodium hydroxide solution at 0° C., and extracted with ethyl acetate (200 mL×2). The combined organic layer was concentrated, and the resulting residue was purified by column chromatography (silica, petroleum ether/ethyl acetate=20/1 to 1/1) to obtain compound A-1 (3.9 g, 21.7 mmol, yield: 21.9%) as a yellow solid. MS (ESI): 182.3 [M+1]$^+$.

Step 3: Preparation of methyl 3-(1-(1-(4-(trifluoromethyl)benzyl)-1H-indole-7-carboxamido)cyclopropyl)bicyclo[1.1.1]pentane-1-carboxylate 1-4

DIPEA (742 mg, 5.74 mmol, 1.0 mL) was added to a solution of compound 1-3 (0.65 g, 2.04 mmol), compound A-1 (378 mg, 2.09 mmol) and HATU (814 mg, 2.14 mmol) in DMF (5 mL). The resulting mixture was stirred for 8 hours under a nitrogen atmosphere at 20° C. LCMS showed that the starting compound 1-3 was consumed, and a major molecular weight peak of the desired product was detected (Rt=0.947 min). The reaction mixture was diluted with ethyl acetate (40 mL), and washed with brine (50 mL×2). The organic layer was dried over anhydrous sodium sulfate, filtered and concentrated under reduced pressure. The resulting residue was purified by column chromatography (silica, petroleum ether/ethyl acetate=100/1 to 3/1, Rf=0.40) to obtain compound 1-4 (0.70 g, crude product) as a white solid. MS (ESI): 483.1 [M+1]$^+$.

Step 4: Preparation of 3-(1-(1-(4-(trifluoromethyl)benzyl)-1H-indole-7-carboxamido)cyclopropyl)bicyclo[1.1.1]pentane-1-carboxylic acid 1

LiOH·H$_2$O (4 M, 1 mL) was added to a solution of compound 1-4 (0.70 g, 1.50 mmol) in ethanol (10 mL). The resulting mixture was stirred at 65° C. for 24 hours. LCMS showed that the raw material was consumed completely, and a major molecular weight peak of the desired product was detected. The reaction mixture was concentrated at 50° C. to remove most of the ethanol. 30 mL of water was added, the resulting mixture was acidified to pH~5 with 1 N hydrochloric acid, and extracted with ethyl acetate (3×50 mL). The organic layers were combined, dried over anhydrous sodium sulfate, filtered and concentrated. The resulting residue was purified by HPLC (column: Phenomenex Synergi C18 150×25×10 μm; mobile phase: [water (0.225% formic acid)-acetonitrile]; B %: 50%-77%, 10 minutes) to obtain compound 1 (350 mg, 747 μmol, yield: 52%) as a white solid. MS (ESI): 469.2 [M+1]$^+$.

$^1$H NMR (400 MHz, DMSO-D$_6$): δ 12.21 (br s, 1H), 8.55 (s, 1H), 7.72 (dd, J=1.1, 7.8 Hz, 1H), 7.56 (d, J=8.2 Hz, 2H), 7.47 (d, J=3.2 Hz, 1H), 7.19 (dd, J=1.0, 7.2 Hz, 1H), 7.12-7.07 (m, 1H), 6.96 (d, J=8.2 Hz, 2H), 6.64 (d, J=3.2 Hz, 1H), 5.70 (s, 2H), 1.70 (s, 6H), 0.57-0.51 (m, 2H), 0.34-0.27 (m, 2H).

Example 2

3-(1-(1-((5-Phenylpyridin-2-yl)methyl)-1H-indole-7-carboxamido)cyclopropyl)bicyclo[1.1.1]pentane-1-carboxylic acid 2

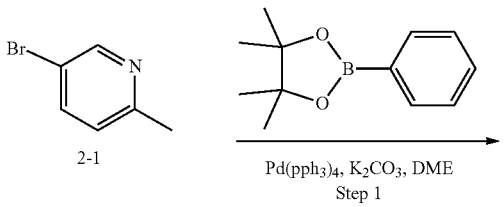

2-1

Pd(pph$_3$)$_4$, K$_2$CO$_3$, DME
Step 1

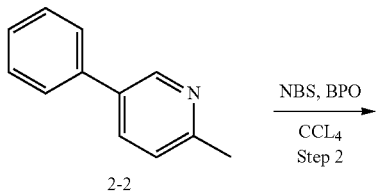

2-2

NBS, BPO
CCL$_4$
Step 2

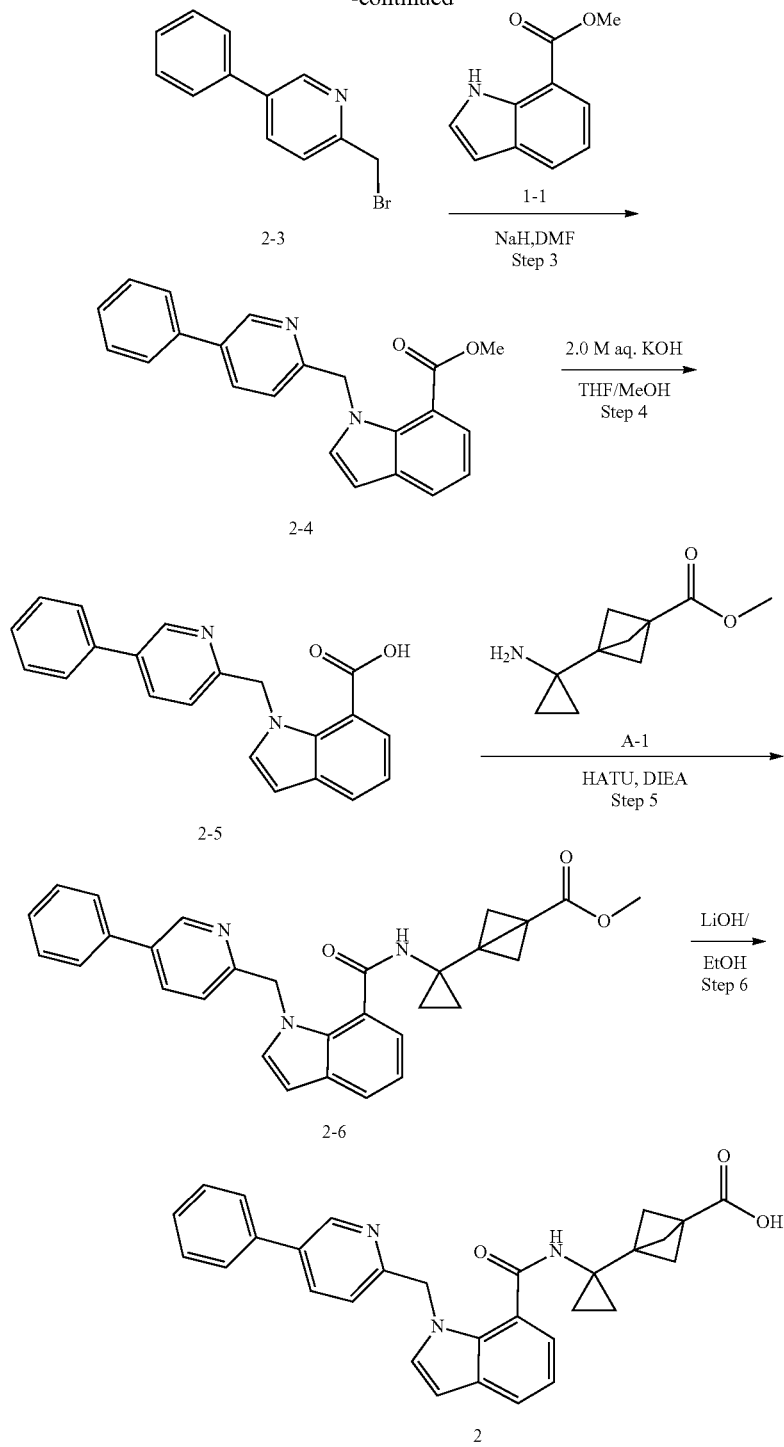

Step 1: Preparation of 2-methyl-5-phenylpyridine 2-2

Pd(PPh$_3$)$_4$ (5.04 g, 4.36 mmol), 4,4,5,5-tetramethyl-2-phenyl-1,3,2-dioxaborolane (20.0 g, 98.0 mmol) and K$_2$CO$_3$ (2 M, 66.0 mL) were added to a solution of 5-bromo-2-methylpyridine 2-1 (15.0 g, 87.2 mmol) in DME (150 mL) under a nitrogen atmosphere. The resulting mixture was stirred at 120° C. for 6 hours. TLC (petroleum ether/ethyl acetate=5/1) showed that the raw material (Rf=0.6) was consumed, and a new point was formed (Rf=0.37). The reaction mixture was extracted with ethyl acetate (100 mL). The organic layer was washed with brine (200 mL), dried over anhydrous sodium sulfate, filtered and concentrated under reduced pressure. The resulting residue was purified by flash silica gel chromatography (ISCO®; 10 g Sepa-Flash® silica column, the eluent was 2~10% ethyl acetate/ petroleum ether gradient, Rf=0.46) to obtain compound 2-2 (10.0 g, 59.0 mmol, yield: 67.7%) as a yellow liquid. MS (ESI): 170 [M+1]+.

$^1$H NMR (400 MHz, CDCl$_3$): δ 8.75 (d, J=2.3 Hz, 1H), 7.79 (dd, J=2.4, 8.0 Hz, 1H), 7.61-7.55 (m, 2H), 7.51-7.44 (m, 2H), 7.43-7.35 (m, 1H), 7.23 (d, J=7.9 Hz, 1H), 2.62 (s, 3H).

Step 2: Preparation of 2-(bromomethyl)-5-phenylpyridine 2-3

Benzoylbenzoic acid peroxide (720 mg, 2.97 mmol) was added to a solution of compound 2-2 (5.00 g, 29.5 mmol) and NBS (5.26 g, 29.5 mmol) in CCl$_4$ (100 mL). The resulting mixture was stirred at 75° C. for 10 hours. TLC (petroleum ether/ethyl acetate=5/1) showed that most of the starting material (Rf=0.45) was consumed, and a new major point was formed (Rf=0.57). The reaction mixture was concentrated at 50° C., and the resulting residue was purified by flash silica gel chromatography (ISCO®; 10 g Sepa-Flash® silica column, 0~3% ethyl acetate/petroleum ether gradient) to obtain compound 2-3 (1.50 g, 5.85 mmol, yield: 19.8%) as a pink solid. MS (ESI): 248 [M+1]+.

$^1$H NMR (400 MHz, DMSO-D$_6$): δ 8.93-8.83 (m, 1H), 8.11 (dd, J=2.4, 8.1 Hz, 1H), 7.78-7.72 (m, 2H), 7.65 (dd, J=0.6, 8.1 Hz, 1H), 7.55-7.49 (m, 2H), 7.48-7.42 (m, 1H), 4.76 (s, 2H).

Step 3: Preparation of methyl 1-((5-phenylpyridin-2-yl)methyl)-1H-indole-7-carboxylate 2-4

In accordance with a method similar to the method for preparing compound 1-2, methyl 1H-indole-7-carboxylate 1-1 was reacted with compound 2-3. The desired compound 2-4 (1.50 g, 4.38 mmol, yield: 72.4%) was obtained as a yellow solid. MS (ESI): 343.2 [M+1]+.

$^1$H NMR (400 MHz, DMSO-D$_6$): δ 8.76 (d, J=1.8 Hz, 1H), 7.94 (dd, J=2.3, 8.2 Hz, 1H), 7.83 (d, J=7.8 Hz, 1H), 7.69-7.61 (m, 3H), 7.51-7.35 (m, 4H), 7.10 (t, J=7.6 Hz, 1H), 6.75-6.66 (m, 2H), 5.74 (s, 2H), 3.70 (s, 3H).

Step 4: Preparation of 1-((5-phenylpyridin-2-yl)methyl)-1H-indole-7-carboxylic acid 2-5

In accordance with a method similar to the method for preparing compound 1-3, compound 2-4 was hydrolyzed to obtain compound 2-5 (0.80 g, crude product) as a yellow solid, which was used directly in the next step. MS (ESI): 329.2 [M+1]+.

Step 5: Preparation of methyl 3-(1-(1-((5-phenylpyridin-2-yl)methyl)-1H-indole-7-carboxamido)cyclopropyl)bicyclo[1.1.1]pentane-1-carboxylate 2-6

This reaction was conducted in accordance with a method similar to the method for preparing compound 1-4 to obtain compound 2-6 (0.50 g, crude product) as a white solid. MS (ESI): 429.3 [M+1]+.

Step 6: Preparation of 3-(1-(1-((5-Phenylpyridin-2-yl)methyl)-1H-indole-7-carboxamido)cyclopropyl)bicyclo[1.1.1]pentane-1-carboxylic acid 2

This reaction was conducted in accordance with a method similar to the method for preparing compound 1 to obtain compound 2 as a white solid. MS (ESI): 478.1 [M+1]+.

$^1$H NMR (400 MHz, DMSO-D$_6$): δ 8.84 (br s, 1H), 8.52 (s, 1H), 8.04-7.92 (m, 1H), 7.73 (d, J=7.9 Hz, 1H), 7.69-7.63 (m, 2H), 7.55-7.47 (m, 3H), 7.46-7.39 (m, 2H), 7.22-7.16 (m, 1H), 7.14-7.07 (m, 1H), 6.67 (d, J=3.1 Hz, 1H), 6.42 (br d, J=8.1 Hz, 1H), 5.76 (br s, 2H), 1.72 (s, 6H), 0.659-0.56 (m, 2H), 0.41-0.38 (m, 2H).

Example 3

3-(1-(1-(Quinolin-2-ylmethyl)-1H-indole-7-carboxamido)cyclopropyl)bicyclo[1.1.1]pentane-1-carboxylic acid 3

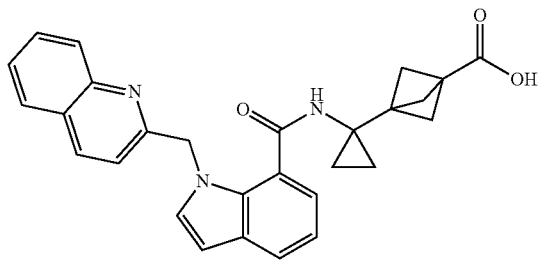

In accordance with a preparation method similar to the method described in Example 1, compound 1-2 was replaced with methyl 1-(quinolin-2-ylmethyl)-1H-indole-7-carboxylate, accordingly, compound 3 was obtained as a light yellow solid. MS (ESI): 452.1 [M+1]+.

$^1$H NMR (400 MHz, DMSO-D$_6$): δ 8.49 (s, 1H), 8.26 (br, 1H), 8.04-7.90 (m, 2H), 7.83-7.70 (m, 2H), 7.66-7.53 (m, 2H), 7.20-7.15 (m, 1H), 7.13-7.06 (m, 1H), 6.68 (d, J=3.2 Hz, 1H), 6.52 (d, J=8.6 Hz, 1H), 5.87 (s, 2H), 4.2 (br, 1H), 1.69 (s, 6H), 0.47-0.44 (m, 2H), 0.29-0.22 (m, 2H).

Example 4

3-(1-(1-(4-Chlorobenzyl)-1H-indole-7-carboxamido)cyclopropyl)bicyclo[1.1.1]pentane-1-carboxylic acid 4

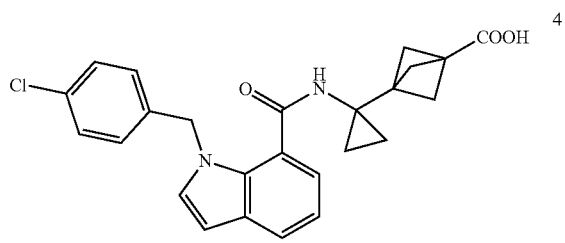 [SMILES: O=C(NC1(C23CC(C(=O)O)(C2)C3)CC1)c1cccc2ccn(Cc3ccc(Cl)cc3)c12]

In accordance with the method described in Example 1, compound 1-2 was replaced with methyl 1-(4-chlorobenzyl)-1H-indole-7-carboxylate, accordingly, compound 4 was obtained as an off-white solid. MS (ESI): 434.1 [M+1]+.

$^1$H NMR (400 MHz, CDCl$_3$): δ 7.77 (dd, J=0.9, 7.9 Hz, 1H), 7.23-7.14 (m, 3H), 7.14-7.07 (m, 2H), 6.72 (d, J=8.4 Hz, 2H), 6.63 (d, J=3.2 Hz, 1H), 6.06 (s, 1H), 5.60 (s, 2H), 1.94 (s, 6H), 0.76-0.68 (m, 2H), 0.52-0.46 (m, 2H).

Example 5
3-(1-(1-((6-Phenylpyridin-3-yl)methyl)-1H-indole-7-carboxamido)cyclopropyl)bicyclo[1.1.1]pentane-1-carboxylic acid 5
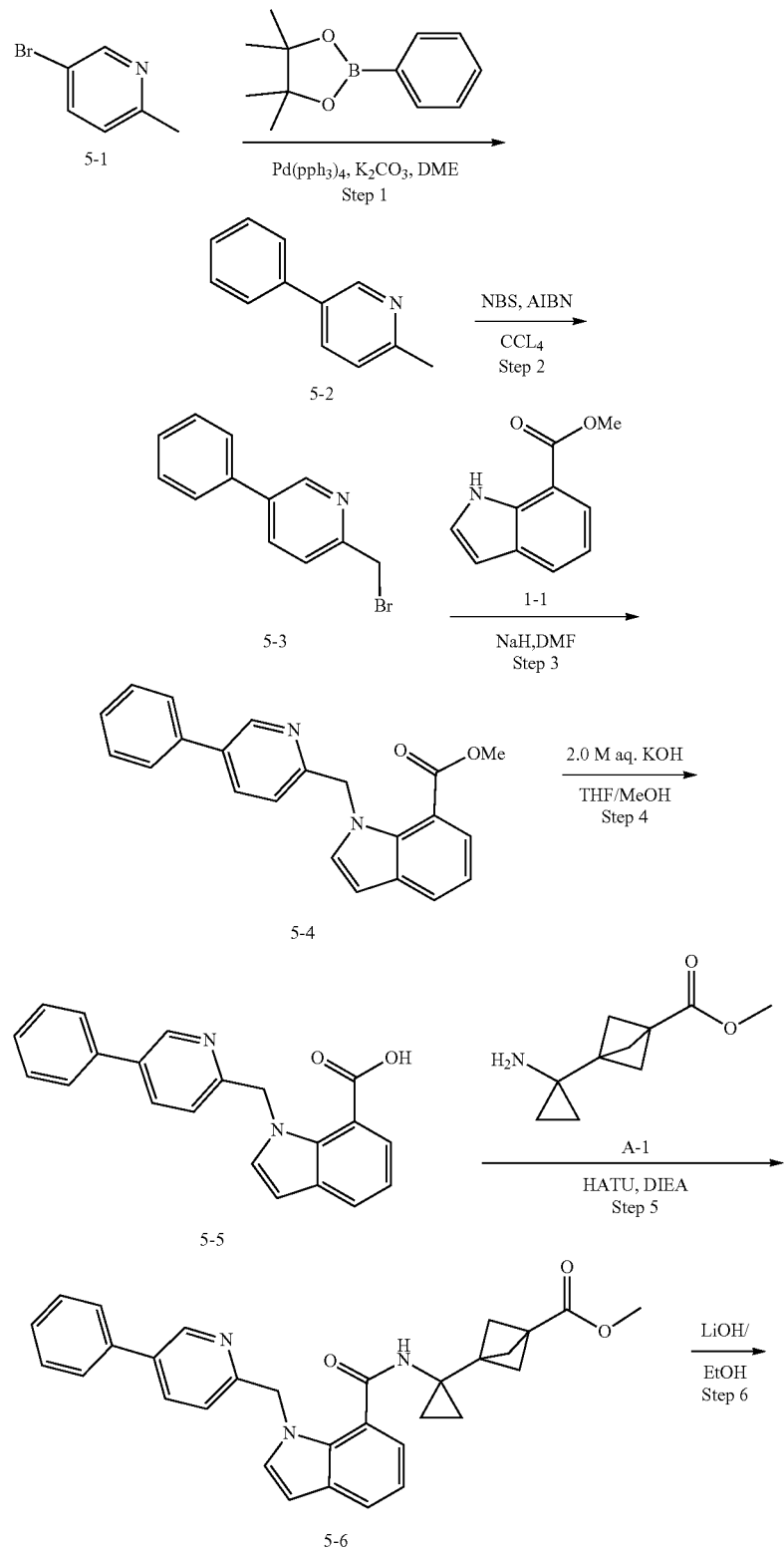

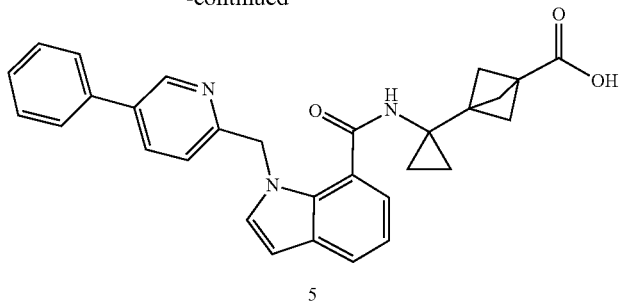

Step 1: Preparation of 5-methyl-2-phenylpyridine 5-2

Aqueous K₂CO₃ solution (2.00 M, 17.5 mL) and Pd(PPh₃)₄ (1.34 g, 1.16 mmol) were added to a solution of 2-bromo-5-methylpyridine 5-1 (4.00 g, 23.2 mmol) and 4,4,5,5-tetramethyl-2-phenyl-1,3,2-dioxaborolane a (5.31 g, 26.0 mmol) in DME (40.0 mL) under a nitrogen atmosphere. The resulting mixture was stirred at 110° C. for 15 hours. TLC (petroleum ether/ethyl acetate=20/1) showed that the raw material (Rf=0.55) was consumed completely, and a new major point was formed (Rf=0.50). The reaction mixture was cooled to room temperature, and extracted with ethyl acetate (20.0 mL×3). The combined organic layer was washed with water (20.0 mL×2) and brine (20.0 mL), dried over anhydrous sodium sulfate, filtered and concentrated under vacuum. The resulting residue was purified by column chromatography (silica, petroleum ether/ethyl acetate=1/0~30/1) to obtain compound 5-2 (4.50 g, 19.8 mmol, yield: 57.0%) as a yellow oil. MS (ESI): 170.1 [M+1]⁺.

Step 2: Preparation of 5-methyl-2-phenylpyridine 5-3

AIBN (217 mg, 1.33 mmol) was added to a solution of compound 5-2 (3.00 g, 13.2 mmol) and NBS (2.83 g, 15.9 mmol) in CCl₄ (30.0 mL) under a nitrogen atmosphere. The resulting mixture was stirred for 14 hours under a nitrogen atmosphere at 70° C. TLC (petroleum ether/ethyl acetate=20/1) showed that most of the raw material (Rf=0.40) was consumed, and a new major point was formed (Rf=0.33). Water (20.0 mL) was added, and the reaction mixture was extracted with CH₂C₂ (20 mL×3). The combined organic layer was washed with brine (20.0 mL×2), dried over anhydrous sodium sulfate, filtered and concentrated under vacuum. The resulting residue was purified by column chromatography (silica, petroleum ether/ethyl acetate=1/0~20/1) to obtain compound 5-3 (1.80 g, 4.81 mmol, yield: 36.2%) as a light yellow solid. MS (ESI): 248.1 [M+1]⁺.

Steps 3 to 6: Preparation of 3-(1-(1-((6-phenylpyridin-3-yl)methyl)-1H-indole-7-carboxamido)cyclopropyl)bicyclo[1.1.1]pentane-1-carboxylic acid 5

The conversion from compound 5-3 to the final product was conducted in accordance with a method similar to the method used in Example 2, accordingly, compound 5 was obtained as an off-white solid. MS (ESI): 478.2 [M+1]⁺.

¹H NMR (400 MHz, CDCl₃): δ12.24 (s, 1H), 8.73 (d, J=1.6 Hz, 1H), 8.15 (d, J=1.6 Hz, 1H), 7.89 (dd, J=8.0 Hz, 2H), 7.78 (dd, J=8.0 Hz, 1H), 7.59 (d, J=8.0 Hz, 1H), 7.44-7.39 (m, 3H), 7.26-7.22 (m, 1H), 7.17-7.16 (d, J=3.2 Hz, 1H), 7.12-7.09 (t, J=7.6 Hz, 1H), 6.66-6.65 (m, 1H), 6.21 (s, 1H), 5.69 (s, 2H), 1.92 (s, 6H), 0.72-0.70 (m, 2H), 0.53-0.52 (m, 2H).

Example 6

3-(1-(1-(Benzofuran-2-ylmethyl)-1H-indole-7-carboxamido)cyclopropyl)bicyclo[1.1.1]pentane-1-carboxylic acid 6

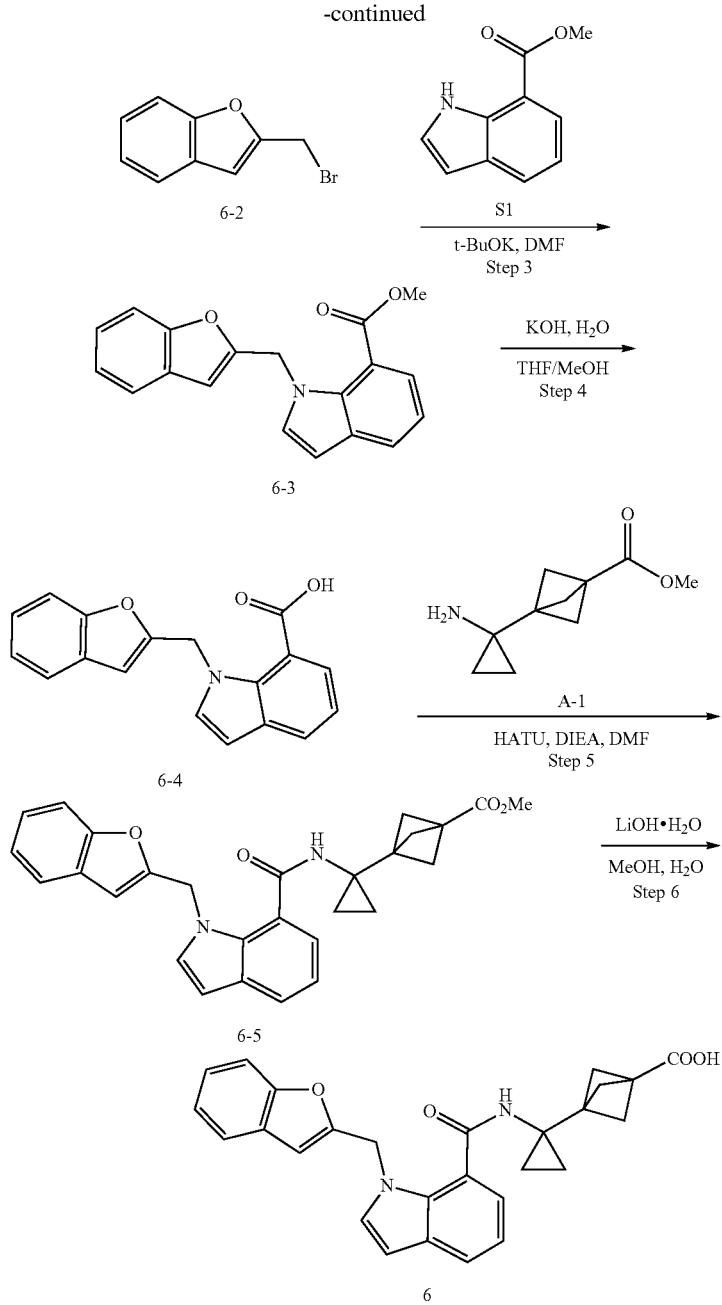

Step 1: Synthesis of benzofuran-2-ylmethanol 6-1

Benzofuran-2-carbaldehyde (3 g, 20.5 mmol) and anhydrous methanol (40 ml) were added successively to a reaction flask, and the resulting mixture was cool to 0° C. Sodium borohydride (0.545 g, 14.4 mmol) was added thereto in batches, and the the temperature was kept below 25° C. After completion of the addition, the reaction mixture was stirred at room temperature for 1 hour. After completion of the reaction, the solvent was removed under reduced pressure. 1 N aqueous HCl solution (15 ml) was added, and the resulting mixture was stirred at room temperature for 5 minutes. The mixture was adjusted to the pH 8-9 with saturated aqueous sodium bicarbonate solution, and extracted with ethyl acetate (10 ml×3). The combined organic phase was washed with saturated brine, dried over anhydrous sodium sulfate, and concentrated under reduced pressure to remove the solvent and obtain compound 6-1 (3.0 g, 20.27 mmol, yield: 98.9%) as a yellow oil. MS (ESI): 149.1 [M+1]$^+$.

$^1$H NMR (400 MHz, CDCl$_3$) δ: 7.55 (dd, J=8.4, 7.2 Hz, 1H), 7.47 (dd, J=8.8, 7.6 Hz, 1H), 7.29-7.19 (m, 2H), 6.66 (s, 1H), 4.77 (d, J=4.8 Hz, 2H).

Step 2: Synthesis of 2-(bromomethyl)benzofuran 6-2

Compound 6-1 (2.47 g, 16.7 mmol) and dry dichloromethane (32 ml) were added successively to a reaction flask, and the resulting mixture was cool to 0° C. Phosphorus tribromide (1.72 mL, 18.4 mmol) was slowly added dropwise thereto. After completion of the addition, the reaction mixture was warmed up to room temperature and stirred for 1 hour. TLC (petroleum ether:ethyl acetate=9:1) showed that the reaction was completed. The reaction mixture was adjusted to the pH 8-9 with saturated aqueous sodium bicarbonate solution, and extracted with dichloromethane (10 ml×3). The combined organic phase was washed with saturated brine, dried over anhydrous sodium sulfate, and concentrated under reduced pressure to remove the solvent and obtain compound 6-2 (3.36 g, yield: 95.9%) as a yellow oil.

Then, in accordance with the method described in Example 1, 1-(bromomethyl)-4-(trifluoromethyl)benzene was replaced with compound 6-2, accordingly, 3-(1-(1-(benzofuran-2-ylmethyl)-1H-indole-7-carboxamido)cyclopropyl)bicyclo[1.1.1]pentane-1-carboxylic acid 6 was obtained as an off-white solid. MS (ESI): 441.1 [M+1]$^+$.

$^1$H NMR (400 MHz, DMSO-D$_6$): δ 12.21 (s, 1H), 8.73 (s, 1H), 7.69 (d, J=7.6 Hz, 1H), 7.51 (d, J=3.2 Hz, 1H), 7.45 (t, J=7.8 Hz, 2H), 7.24-7.06 (m, 4H), 6.60 (d, J=3.2 Hz, 1H), 6.18 (s, 1H), 5.76 (s, 2H), 1.76 (s, 6H), 0.63 (d, J=7.2 Hz, 2H), 0.50 (t, J=5.6 Hz, 2H).

Example 7

3-(1-(5-Chloro-1-((5-phenylpyridin-2-yl)methyl)-1H-indole-7-carboxamido)cyclopropyl)bicyclo[1.1.1]pentane-1-carboxylic acid 7

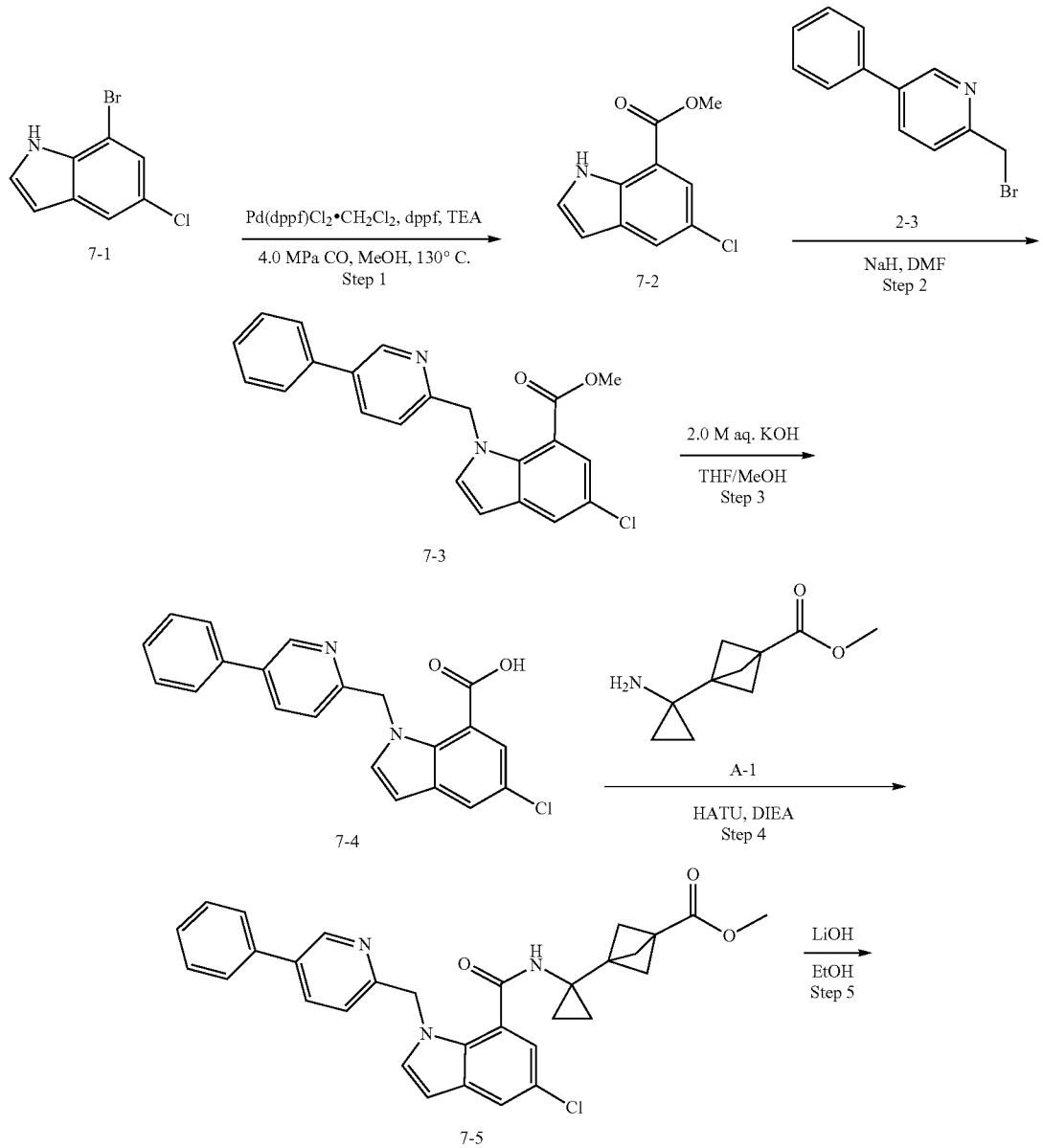

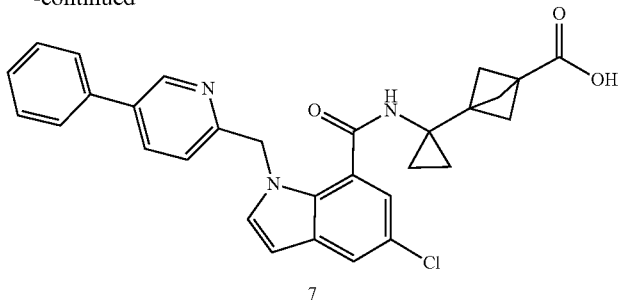

7

Step 1: Preparation of methyl 5-chloro-1H-indole-7-carboxylate 7-2

Pd(dppf)Cl$_2$CH$_2$Cl$_2$ (98.0 mg, 120 µmol), dppf (112 mg, 202 µmol) and TEA (2.80 mL) were added to a solution of 7-bromo-5-chloro-1H-indole 7-1 (1.40 g, 6.07 mmol) in methanol (50.0 mL). The resulting mixture was purged with carbon monoxide, and stirred for 48 hours under a CO atmosphere (4.0 MPa) at 130° C. LC-MS showed that the raw material was consumed completely, and the molecular weight of the desired product was detected (RT=0.880). The mixture was concentrated under reduced pressure, and the resulting residue was purified by column chromatography (silica, petroleum ether/ethyl acetate=1/0~20/1 gradient elution, Rf=0.55) to obtain compound 7-2 (900 mg, 4.29 mmol, yield: 70.7%) as a yellow solid. MS (ESI): 210.0 [M+1]$^+$.

$^1$H NMR (400 MHz, CDCl$_3$): δ 9.85 (s, 1H), 7.87 (d, 1H, J=2.0 Hz), 7.84 (d, 1H, J=1.8 Hz), 7.4-7.4 (m, 1H), 6.6-6.6 (m, 1H), 4.02 (s, 3H).

Steps 2 to 5: Preparation of 3-(1-(5-Chloro-1-((5-phenylpyridin-2-yl)methyl)-1H-indole-7-carboxamido)cyclopropyl)bicyclo[1.1.1]pentane-1-carboxylic acid 7

In accordance with the method described in Example 1, intermediate 7-2 was converted into the final product as an off-white solid. MS (ESI): 512.1 [M+1]$^+$.

$^1$H NMR (400 MHz, DMSO-d$_6$): δ 12.24 (d, J=1.6 Hz, 1H), 8.73 (d, J=1.6 Hz, 1H), 8.63 (s, 1H), 7.85 (dd, J=2.2, 8.2 Hz, 1H), 7.78 (d, J=2.1 Hz, 1H), 7.66-7.57 (m, 3H), 7.47 (t, J=7.5 Hz, 2H), 7.43-7.35 (m, 1H), 7.10 (d, J=1.8 Hz, 1H), 6.65 (d, J=3.2 Hz, 1H), 6.41 (d, J=8.2 Hz, 1H), 5.69 (s, 2H), 1.66 (s, 6H), 0.55-0.48 (m, 2H), 0.36-0.33 (m, 2H).

Example 8

3-(1-(5-Chloro-1-(4-(trifluoromethyl)benzyl)-1H-indole-7-carboxamido)cyclopropyl)bicyclo[1.1.1]pentane-1-carboxylic acid 8

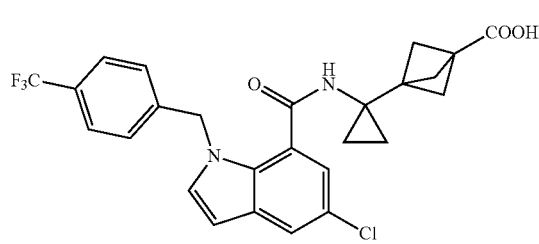

8

In accordance with the method described in Example 1, compound 1-2 was replaced with methyl 5-chloro-1-(4-(trifluoromethyl)benzyl)-1H-indole-7-carboxylate, accordingly, compound 8 was obtained as a white solid. MS (ESI): 503.1 [M+1]$^+$.

$^1$H NMR (400 MHz, DMSO-d$_6$): δ 8.45 (s, 1H), 8.12 (s, 1H), 7.55 (d, 1H, J=2.1 Hz), 7.34 (s, 1H), 7.31 (s, 1H), 7.30 (d, 1H, J=3.2 Hz), 6.89 (d, 1H, J=2.1 Hz), 6.71 (s, 1H), 6.69 (s, 1H), 6.40 (d, 1H, J=3.2 Hz), 5.43 (s, 2H), 1.43 (s, 6H), 0.3-0.3 (m, 2H), 0.0-0.0 (m, 2H).

Example 9

4-(1-(1-(4-(Trifluoromethyl)benzyl)-1H-indole-7-carboxamido)cyclopropyl)bicyclo[2.2.2]octane-1-carboxylic acid 9

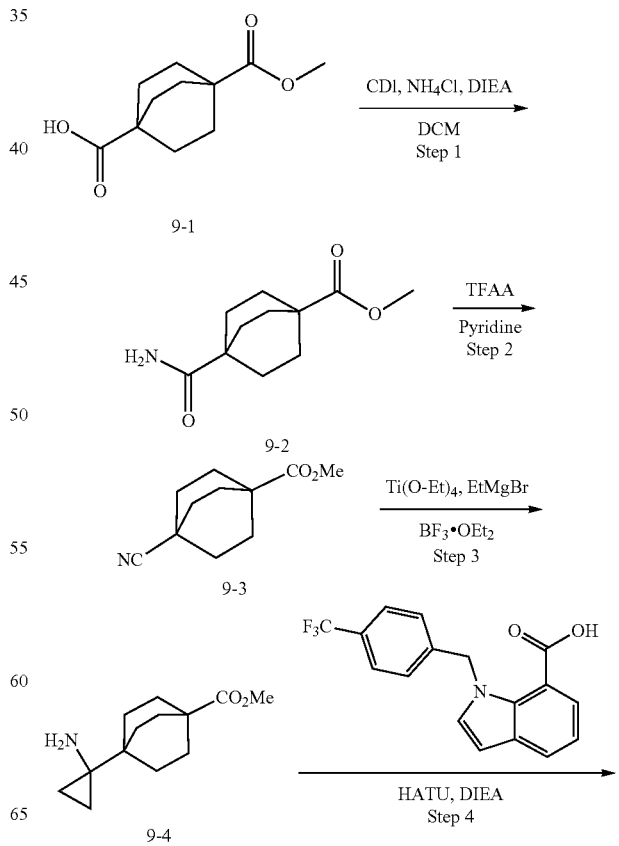

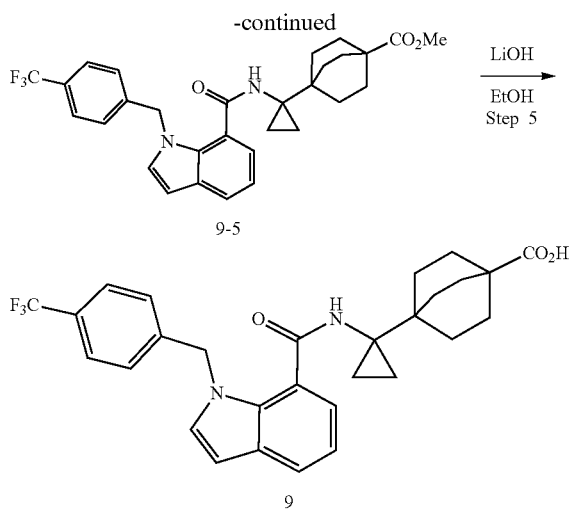

Step 1: Preparation of methyl 4-carbamoylbicyclo[2.2.2]octane-1-carboxylate 9-2

CDI (4.21 g, 25.9 mmol) was added to a solution of 4-(methoxycarbonyl)bicyclo[2.2.2]octane-1-carboxylic acid 9-1 (5.00 g, 23.5 mmol) in dichloromethane (50 mL). The resulting mixture was stirred at 25° C. for 1 hour. DIEA (3.99 g, 30.8 mmol) and NH$_4$Cl (1.51 g, 28.2 mmol) were added. The resulting mixture was stirred at 25° C. for 2 hours. TLC (petroleum ether/ethyl acetate=1/1, I 2) showed that the raw material (Rf=0.50) was consumed, and a new major point was formed (Rf=0.45). The reaction mixture was acidified to pH~3 with 1 N aqueous hydrochloric acid solution, and extracted with dichloromethane (30 mL×3). The combined organic phase was washed with brine (50 mL), dried over anhydrous sodium sulfate, filtered and concentrated under vacuum to obtain the crude compound 9-2 (4.00 g, 18.9 mmol, yield: 80.3%) as a white solid. MS (ESI): 211.1 [M+1]$^+$. This product was used directly in the next step without purification.

Step 2: Preparation of methyl 4-cyanobicyclo[2.2.2]octane-1-carboxylate 9-3

TFAA (9.06 g, 43.1 mmol) was added to a solution of compound 9-2 (4.00 g, 18.9 mmol) in pyridine (49.0 g, 619 mmol) at 0° C. The resulting mixture was stirred at 25° C. for 1 hour. TLC (petroleum ether/ethyl acetate=3/1) showed that the raw material (Rf=0.25, plate 1) was consumed, and a new point was detected (Rf=0.56, plate 2). The reaction mixture was acidified to pH=2~3 with 5.0 N aqueous hydrochloric acid solution, and extracted with dichloromethane (50 mL×3). The combined organic phase was washed with brine (80 mL×3), dried over anhydrous sodium sulfate, filtered and concentrated under vacuum. The resulting residue was purified by column chromatography (petroleum ether/ethyl acetate=50/1~3/1) to obtain compound 9-3 (1.10 g, 5.69 mmol, yield: 30.0%) as a white solid. MS (ESI): 194.1 [M+1]$^+$.

$^1$H NMR (400 MHz, CDCl$_3$): δ 3.66 (s, 3H), 2.03-1.92 (m, 6H), 1.89-1.77 (m, 6H).

Step 3: Preparation of methyl 4-(1-aminocyclopropyl)bicyclo[2.2.2]octane-1-carboxylate 9-4

Ti(O-Et)$_4$ (1.05 g, 4.58 mmol) was added dropwise to a solution of compound 9-3 (800 mg, 4.14 mmol) in toluene (15 mL) at 25° C. The resulting mixture was stirred at 25° C. for 15 minutes. EtMgBr (3 M, 2.76 mL) was added dropwise at −20° C., and the resulting mixture was stirred at −20° C. for 15 minutes. BF$_3$·Et$_2$O (1.20 g, 8.43 mmol) was added dropwise at −20° C., and the resulting mixture was stirred at 25° C. for 24 hours. LC-MS showed that the raw material was consumed, and the desired molecular weight was detected (detected at RT=0.838). 10 mL of 1 N aqueous hydrochloric acid solution and 15 mL of water were added, and the resulting mixture was washed with ethyl acetate (15 mL×3). The aqueous solution was basified to pH=8~9 with 10 M aqueous NaOH solution, and extracted with ethyl acetate (25 mL×3). The combined organic phase was washed with brine (50 mL), dried over anhydrous sodium sulfate, filtered and concentrated under vacuum to obtain a residue. The residue was used directly in the next step without purification. Compound 9-4 (0.200 g, crude product) was obtained as a yellow oil. MS (ESI): 224.1 [M+1]$^+$.

Step 4: Preparation of methyl 4-(1-(1-(4-(trifluoromethyl)benzyl)-1H-indole-7-carboxamido)cyclopropyl)bicyclo[2.2.2]octane-1-carboxylate 9-5

Compound 9-4 (92.3 mg, 413 μmol), HATU (160 mg, 420 μmol) and DIPEA (185 μL, 1.06 mmol) were added to a solution of compound 1-3 (120 mg, 375 μmol) in DMF (2.00 mL). The resulting mixture was stirred at 25° C. for 1 hour. LC-MS showed that the starting compound 1-3 was consumed, and the molecular weight of the desired product was detected (RT=1.051). 10 mL of water was added, and the resulting mixture was extracted with ethyl acetate (10 mL×3). The combined organic phase was washed with brine (20 mL×2), dried over anhydrous sodium sulfate, filtered and concentrated under vacuum. The resulting residue was purified by column chromatography (petroleum ether/ethyl acetate=50/1~3/1, plate 1: petroleum ether/ethyl acetate=3/1, Rf=0.45) to obtain compound 9-5 (140 mg, 236 μmol, yield: 62.9%) as a white solid. MS (ESI): 525.2 [M+1]$^+$.

Step 5: Preparation of 4-(1-(1-(4-(trifluoromethyl)benzyl)-1H-indole-7-carboxamido)cyclopropyl)bicyclo[2.2.2]octane-1-carboxylic acid 9

An aqueous solution of LiOH·H$_2$O (4 M, 1.86 mL) was added to a solution of compound 9-5 (140 mg, 236 μmol) in methanol (2.00 mL). The resulting mixture was stirred at 60° C. for 1 hour. LC-MS showed that the raw material was consumed completely, and the molecular weight of the desired product was detected (RT=1.022). The reaction mixture was concentrated to remove methanol. 9 mL of 1 N aqueous hydrochloric acid solution was added, and the resulting mixture was extracted with ethyl acetate (15 mL×3). The combined organic phase was concentrated under vacuum, and the resulting residue was purified by preparative HPLC (column: Shim-pack C18 150×25×10 μm; mobile phase: [water (0.225% formic acid)-acetonitrile]; B %: 45%-75%, 10 min) to obtain compound 9 (75.6 mg, 146 μmol, yield: 61.9%) as a light green solid. MS (ESI): 511.2 [M+1]$^+$.

$^1$H NMR (400 MHz, CDCl$_3$): δ7.78 (dd, J=1.2, 7.9 Hz, 1H), 7.48 (d, J=8.2 Hz, 2H), 7.22 (dd, J=1.0, 7.2 Hz, 1H), 7.16-7.10 (m, 2H), 6.86 (d, J=7.9 Hz, 2H), 6.66 (d, J=3.2 Hz, 1H), 5.95 (s, 1H), 5.74 (s, 2H), 1.77-1.72 (m, 6H), 1.46-1.41 (m, 6H), 0.78-0.72 (m, 2H), 0.34-0.28 (m, 2H).

Example 10
3-(1-(1-((5-Morpholinopyridin-2-yl)methyl)-1H-indole-7-carboxamido)cyclopropyl)bicyclo[1.1.1]pentane-1-carboxylic acid 10
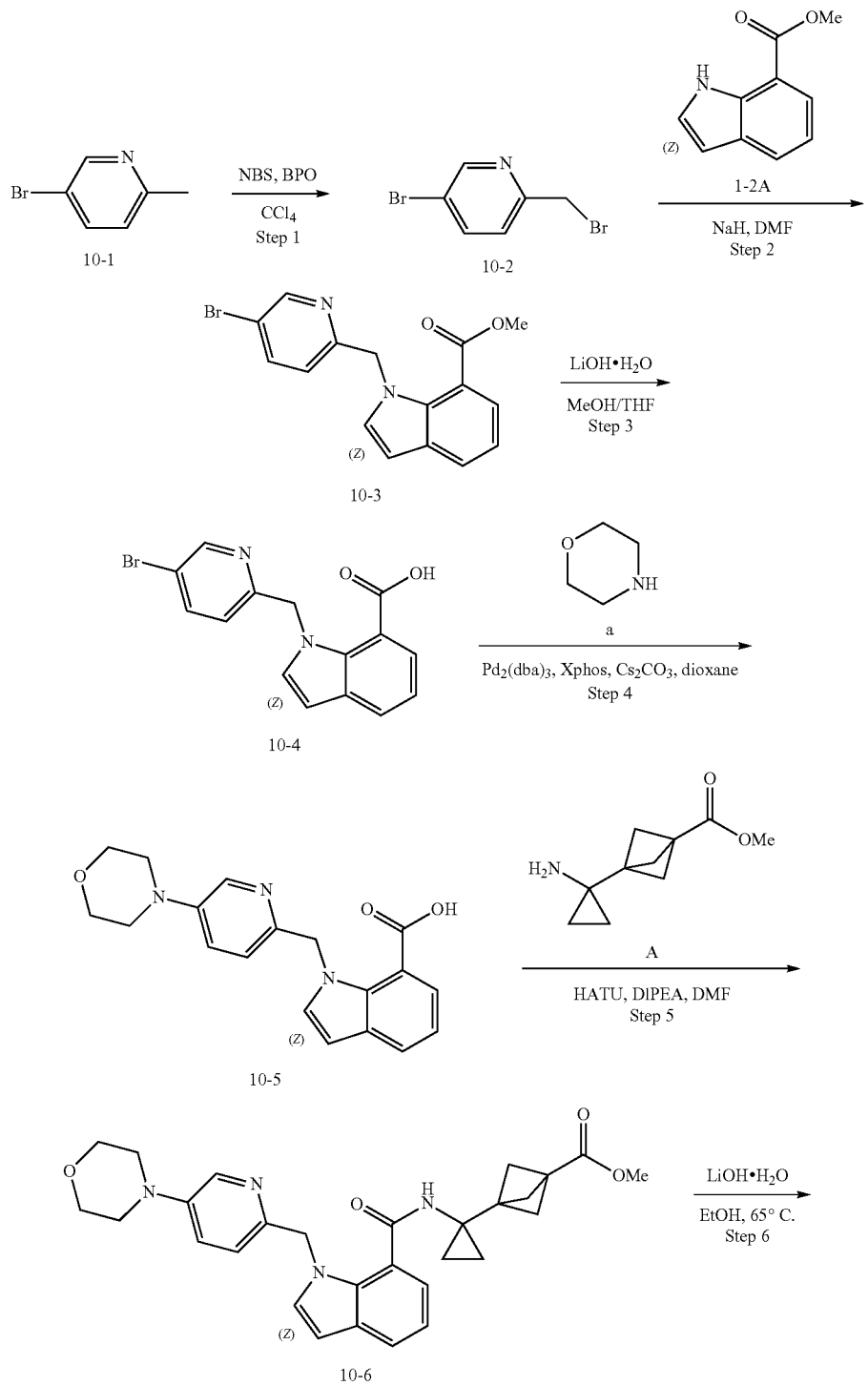

-continued

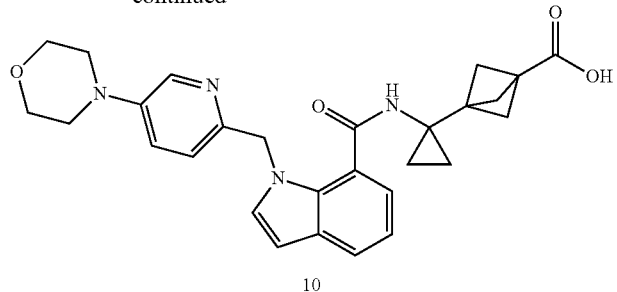

10

Step 1: Preparation of 5-bromo-2-(bromomethyl)pyridine 10-2

NBS (22.7 g, 127 mmol) and BPO (1.30 g, 5.35 mmol) were added to a solution of 5-bromo-2-methylpyridine 10-1 (20.0 g, 116 mmol) in tetrachloromethane (200 mL). The resulting mixture was stirred at 76° C. for 12 hours. TLC (petroleum ether/ethyl acetate=30/1) showed that compound 10-1 (Rf=0.6) was consumed, and two new points were formed (Rf=0.65, Rf=0.7). The reaction mixture was washed with water (70.0 mL×3), dried over anhydrous sodium sulfate, filtered and concentrated. The resulting residue was purified by column chromatography (silica, petroleum ether/ethyl acetate=1/0-5/1, Rf=0.65). Compound 10-2 (9.00 g, yield: 30.3%, purity: 98.3%) was identified by LCMS as a pale yellow oil. MS (ESI): 249.1 [M+1]$^+$.

$^1$H NMR (400 MHz, DMSO-$d_6$): δ 8.55 (d, J=2.32 Hz, 1H), 7.74 (dd, J=8.31, 2.45 Hz, 1H), 7.28 (d, J=8.31 Hz, 1H), 4.45 (s, 2H).

Step 2: Preparation of methyl 1-((5-bromopyridin-2-yl)methyl)-1H-indole-7-carboxylate 10-3

NaH (1.03 g, 43.0 mmol) was added to a solution of methyl 1H-indole-7-carboxylate 1-2A (7.54 g, 43.0 mmol) in DMF (40.0 mL) at 0° C. under a nitrogen atmosphere. The resulting mixture was stirred at 25° C. for 30 minutes. A solution of 5-bromo-2-(bromomethyl)pyridine 10-2 (9.00 g, 35.8 mmol) in DMF (40.0 mL) was added at 0° C. under a nitrogen atmosphere. The resulting mixture was stirred at 25° C. for 30 minutes. LC-MS showed that the starting compound 1-2A was consumed completely. The reaction mixture was diluted with water (100 mL), and extracted with ethyl acetate (300 mL×2). The combined organic layer was washed with brine (100 mL×2), dried over anhydrous sodium sulfate, filtered and concentrated. The resulting residue was purified by column chromatography (silica, petroleum ether/ethyl acetate=1/0 to 2/1) to obtain compound 10-3 (6.80 g, yield: 54.4%, purity: 99.0%) as a brown solid. MS (ESI): 345.1 [M+1]$^+$.

$^1$H NMR (400 MHz, CDCl$_3$): δ 8.52 (d, J=2.1 Hz, 1H), 7.74 (dd, J=1.2, 7.9 Hz, 1H), 7.60-7.50 (m, 2H), 7.13 (d, J=3.2 Hz, 1H), 7.06 (t, J=7.6 Hz, 1H), 6.60 (d, J=3.3 Hz, 1H), 6.44 (d, J=8.3 Hz, 1H), 5.61 (s, 2H), 3.68 (s, 3H).

Step 3: Preparation of 1-((5-bromopyridin-2-yl)methyl)-1H-indole-7-carboxylic acid 10-4

A solution of LiOH·H$_2$O (9.9 g, 176 mmol) in water (90.0 mL) was added to a solution of compound 10-3 (6.8 g, 19.7 mmol) in methanol (90.0 mL) and THF (90.0 mL). The resulting mixture was stirred at 25° C. for 12 hours. LC-MS showed that compound 10-3 was consumed completely, and the desired molecular weight was detected (RT=0.861). The reaction mixture was concentrated to remove methanol and THF, acidified to pH=5~6 with aqueous hydrochloric acid solution (1 M), and a large amount of solid precipitated. The mixture was filtered, and the solid was collected to obtain compound 10-4 (4.00 g, yield: 61.3%) as a white solid. MS (ESI): 331.1 [M+1]$^+$.

$^1$H NMR (400 MHz, DMSO-$d_6$): δ 8.57 (s, 1H), 7.87-7.93 (m, 1H), 7.78-7.83 (m, 1H), 7.57 (d, J=3.30 Hz, 1H), 7.47-7.53 (m, 1H), 7.05-7.14 (m, 1H), 6.65-6.70 (m, 1H), 6.48-6.56 (m, 1H), 5.75-5.84 (m, 2H).

Step 4: Preparation of 1-((5-morpholinopyridin-2-yl)methyl)-1H-indole-7-carboxylic acid 10-5

Morpholine (126 mg, 1.45 mmol, 127 μL), XPhos (69.1 mg, 144 μmol) and Cs$_2$CO$_3$ (944 mg, 2.90 mmol) were added to a solution of compound 10-4 (240 mg, 724 μmol) in dioxane (12.0 mL). The resulting mixture was degassed and purged with nitrogen 3 times. Pd$_2$(dba)$_3$ (66.3 mg, 72.4 μmol) was added, and the resulting mixture was stirred for 2 hours at 120° C. under a nitrogen atmosphere. LCMS showed that compound 10-4 was consumed completely, and the desired molecular weight was detected (RT=0.233). The mixture was filtered, and the filtrate was concentrated. The resulting residue was purified by preparative HPLC (neutral) to obtain compound 10-5 (120 mg, yield: 41.9%, purity: 85.4%) as a pale yellow solid. MS (ESI): 337.1 [M+1]$^+$.

Step 5: Preparation of methyl 3-(1-(1-((5-morpholinopyridin-2-yl)methyl)-1H-indole-7-carboxamido)cyclopropyl)bicyclo[1.1.1]pentane-1-carboxylate 10-6

A mixture of compound 10-5 (50.0 mg, 148 μmol), methyl 3-(1-aminocyclopropyl)bicyclo[1.1.1]pentane-1-carboxylate A1 (27.0 mg, 149 μmol), HATU (57.0 mg, 149 μmol) and DIEA (57.8 mg, 447 μmol, 78.0 μL) in DMF (1.0 mL) was stirred at 25° C. for 4 hours. LCMS showed that compound 10-5 was consumed completely, and the desired molecular weight was detected (RT=0.792). TLC (ethyl acetate) showed that compound 10-5 (Rf=0.30) was consumed completely, and two new points were formed (Rf=0.41, Rf=0.6). The reaction mixture was diluted with water (5 mL), and extracted with ethyl acetate (10 mL×2). The combined organic layer was washed with brine (20 mL×2), dried over anhydrous sodium sulfate, filtered and concentrated. The resulting residue was purified by preparative TLC (silica, ethyl acetate, Rf=0.6) to obtain compound 10-6 (60.0 mg, yield: 80.8%) as a white solid. MS (ESI): 501.1 [M+1]$^+$.

Step 6: Preparation of 3-(1-(1-((5-morpholinopyridin-2-yl)methyl)-1H-indole-7-carboxamido)cyclopropyl)bicyclo[1.1.1]pentane-1-carboxylic acid 10

A solution of LiOH·H$_2$O (49.0 mg, 1.17 mmol) in water (0.3 mL) was added to a solution of compound 10-6 (60.0 mg, 119 µmol) in ethanol (3.00 mL). The resulting mixture was stirred at 65° C. for 12 hours. LCMS showed that compound 10-6 was consumed completely, and the desired molecular weight was detected (RT=0.777). The reaction mixture was acidified to pH=6 to 7, and directly purified by preparative HPLC (column: Phenomenex Synergi C18 150×25×10 µm; mobile phase: [water (0.225% FA)-ACN]; B %: 12%-42%, 10 minutes) to obtain compound 10 (16.6 mg, yield: 28.3%, purity: 99.4%) as a pale yellow solid. MS (ESI): 487.2 [M+1]$^+$.

$^1$H NMR (400 MHz, DMSO-d$_6$): δ 12.24 (s, 1H), 8.50 (s, 1H), 8.17 (d, J=2.81 Hz, 1H), 7.67 (dd, J=7.83, 1.22 Hz, 1H), 7.41 (d, J=3.18 Hz, 1H), 7.10-7.15 (m, 2H), 7.08-7.03 (m, 1H), 6.59 (d, J=3.18 Hz, 1H), 6.30 (d, J=8.68 Hz, 1H), 5.52 (s, 2H), 3.73-3.69 (m, 4H), 3.08-3.05 (m, 4H), 1.70 (s, 6H), 0.62-0.58 (m, 2H), 0.50-0.45 (m, 2H).

Example 11

3-(1-(1-([2,3'-Bipyridin]-6'-ylmethyl)-1H-indole-7-carboxamido)cyclopropyl)bicyclo[1.1.1]pentane-1-carboxylic acid 11

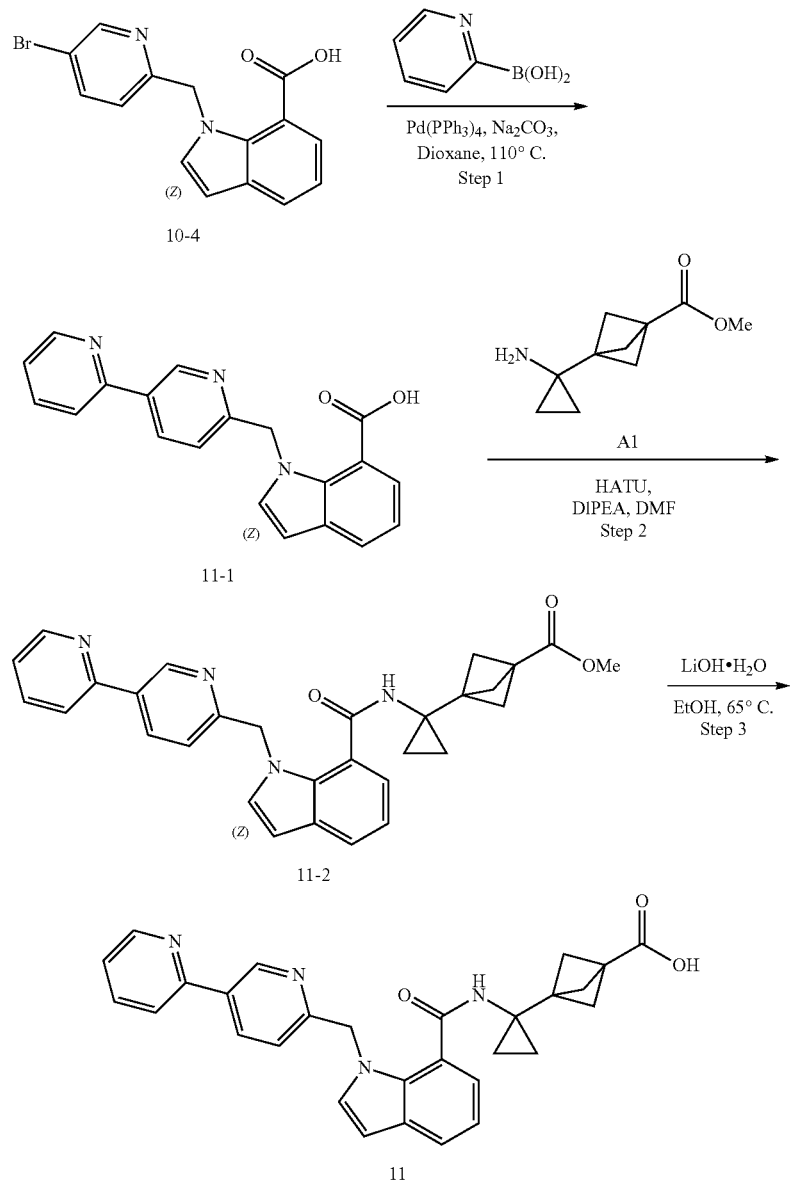

Step 1: Preparation of 1-([2,3'-bipyridin]-6'-ylmethyl)-1H-indole-7-carboxylic acid 11-1

Pd(PPh$_3$)$_4$ (44.0 mg, 38.0 µmol) was added to a solution of compound 10-4 (200 mg, 603 µmol), pyridin-2-ylboronic acid (80.0 mg, 650 µmol) and Na$_2$CO$_3$ (212.0 mg, 2.00 mmol) in water (1.5 mL) and dioxane (6 mL). The resulting mixture was stirred for 8 hours under a nitrogen atmosphere at 100° C. LCMS showed that compound 10-4 was consumed, and the desired molecular weight was detected (RT=0.794). The reaction mixture was filtered, and the filtrate was concentrated under reduced pressure. The resulting residue was purified by reversed phase HPLC (0.1% FA) to obtain compound 11-1 (120 mg, yield: 29.6%, purity: 96.2%) as a white solid. MS (ESI): 330.3 [M+1]⁺.

Step 2: Preparation of methyl 3-(1-(1-([2,3'-bipyridin]-6'-ylmethyl)-1H-indole-7-carboxamido)cyclopropyl)bicyclo[1.1.1]pentane-1-carboxylate 11-2

A mixture of compound 11-1 (50.0 mg, 150 μmol), methyl 3-(1-aminocyclopropyl)bicyclo[1.1.1]pentane-1-carboxylate A1 (27.0 mg, 149 μmol), HATU (57.0 mg, 149 μmol) and DIEA (57.8 mg, 447 μmol, 78.0 μL) in DMF (1.0 mL) was stirred at 25° C. for 4 hours. LCMS showed that compound 11-1 was consumed completely, and the desired molecular weight was detected (RT=0.692). The reaction mixture was diluted with water (5 mL), and extracted with ethyl acetate (10 mL×2). The combined organic layer was washed with brine (20 mL×2), dried over anhydrous sodium sulfate, filtered and concentrated. The resulting residue was purified by preparative TLC (SiO₂, ethyl acetate, Rf=0.5) to obtain compound 11-2 (58.0 mg, yield: 79%) as a white solid. MS (ESI): 493.1 [M+1]⁺.

Step 3: Preparation of 3-(1-(1-([2,3'-bipyridin]-6'-ylmethyl)-1H-indole-7-carboxamido)cyclopropyl)bicyclo[1.1.1]pentane-1-carboxylic acid 11

A solution of LiOH·H₂O (49.0 mg, 1.17 mmol) in water (0.3 mL) was added to a solution of compound 11-2 (58.0 mg, 117 μmol) in ethanol (3.00 mL). The resulting mixture was stirred at 65° C. for 12 hours. LCMS showed that compound 11-2 was consumed completely, and the desired molecular weight was detected (RT=0.777). The reaction mixture was acidified to pH=6 to 7, and directly purified by preparative HPLC (column: Phenomenex Synergi C18 150× 25×10 μm; mobile phase: [water (0.225% FA)-ACN]; B %: 12%-42%, 10 minutes) to obtain compound 11 (24 mg, 50.2 μmol, yield: 42.9%) as a pale yellow solid. MS (ESI): 479.5 [M+1]⁺.

¹H NMR (400 MHz, DMSO-d₆): δ 12.34 (s, 1H), 9.14 (d, J=2.0 Hz, 1H), 8.66 (d, J=4.8 Hz, 1H), 8.43 (s, 1H), 8.18 (dd, J=2.2, 8.2 Hz, 1H), 7.98-7.93 (m, 1H), 7.89 (d, J=1.6 Hz, 1H), 7.70 (d, J=7.6 Hz, 1H), 7.51 (d, J=3.2 Hz, 1H), 7.37 (dd, J=4.9, 7.1 Hz, 1H), 7.13 (s, 1H), 7.08 (d, J=7.6 Hz, 1H), 6.64 (d, J=3.2 Hz, 1H), 6.39 (d, J=8.2 Hz, 1H), 5.69 (s, 2H), 1.61 (s, 6H), 0.49 (s, 2H), 0.34-0.33 (m, 2H).

Example 12

3-(1-(1-([3,3'-Bipyridin]-6-ylmethyl)-1H-indole-7-carboxamido)cyclopropyl)bicyclo[1.1.1]pentane-1-carboxylic acid 12

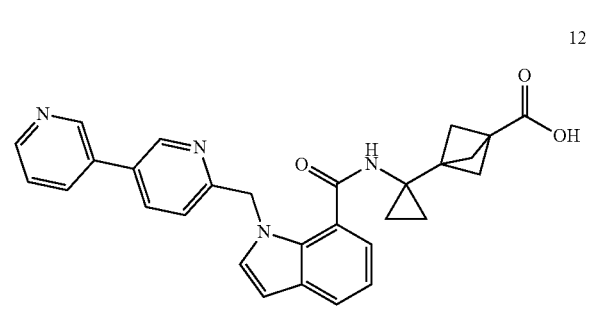 [SMILES: O=C(NC1(C23CC(C(=O)O)(C2)C3)CC1)c1cccc2ccn(Cc3ccc(-c4cccnc4)cn3)c12]

In accordance with a preparation method similar to the method described in Example 11, compound 11-0 in Step 1 was replaced with pyridin-3-ylboronic acid, accordingly, compound 12 was obtained as a light yellow solid. MS (ESI): 479.5.

¹H NMR (400 MHz, DMSO-d₆): δ 12.21 (s, 1H), 8.85 (dd, J=11.25, 1.83 Hz, 2H), 8.60 (dd, J=4.71, 1.53 Hz, 1H), 8.46-8.48 (m, 1H), 8.08 (dt, J=8.07, 1.90 Hz, 1H), 7.93 (dd, J=8.13, 2.38 Hz, 1H), 7.72 (dd, J=7.82, 1.10 Hz, 1H), 7.49-7.53 (m, 2H), 7.14-7.18 (m, 1H), 7.07-7.12 (m, 1H), 6.66 (d, J=3.18 Hz, 1H), 6.39 (d, J=8.19 Hz, 1H), 5.73 (s, 2H), 1.63 (s, 6H), 0.51-0.56 (m, 2H), 0.33-0.39 (m, 2H).

Example 13

3-(1-(1-([3,4'-Bipyridin]-6-ylmethyl)-1H-indole-7-carboxamido)cyclopropyl)bicyclo[1.1.1]pentane-1-carboxylic acid 13

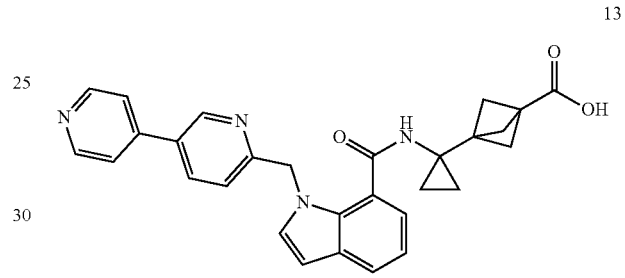

In accordance with a preparation method similar to the method described in Example 11, compound 11-0 in Step 1 was replaced with pyridin-4-ylboronic acid, accordingly, compound 13 was obtained as a light yellow solid. MS (ESI): 479.5.

¹H NMR (400 MHz, DMSO-d₆): δ 12.20 (s, 1H), 8.90 (d, J=2.0 Hz, 1H), 8.67-8.63 (m, 2H), 8.47 (s, 1H), 7.99 (dd, J=2.4, 8.3 Hz, 1H), 7.74-7.68 (m, 3H), 7.52 (d, J=3.2 Hz, 1H), 7.19-7.14 (m, 1H), 7.12-7.07 (m, 1H), 6.66 (d, J=3.2 Hz, 1H), 6.40 (d, J=8.3 Hz, 1H), 5.74 (s, 2H), 1.65 (s, 6H), 0.57-0.52 (m, 2H), 0.39-0.33 (m, 2H).

Example 14

3-(1-(1-((5-(1-Methyl-1H-pyrazol-4-yl)pyridin-2-yl)methyl)-1H-indole-7-carboxamido)cyclopropyl)bicyclo[1.1.1]pentane-1-carboxylic acid 14

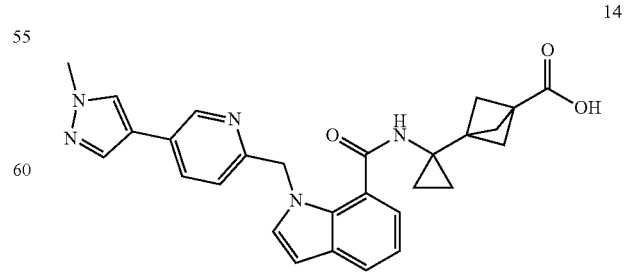

In accordance with a preparation method similar to the method described in Example 11, compound 11-0 in Step 1 was replaced with (1-methyl-1H-pyrazol-4-yl)boronic acid, accordingly, compound 14 was obtained as a white solid. MS (ESI): 482.2.

¹H NMR (400 MHz, DMSO-d₆): δ 12.20 (s, 1H), 8.69 (d, J=1.71 Hz, 1H), 8.50 (s, 1H), 8.15 (s, 1H), 7.85 (d, J=0.61 Hz, 1H), 7.68-7.72 (m, 2H), 7.48 (d, J=3.18 Hz, 1H), 7.14-7.16 (m, 1H), 7.06-7.10 (m, 1H), 6.63 (d, J=3.18 Hz, 1H), 6.28 (d, J=8.19 Hz, 1H), 5.62 (s, 2H), 3.86 (s, 3H), 1.69 (s, 6H), 0.54-0.57 (m, 2H), 0.39-0.43 (m, 2H).

Example 15

3-(1-(1-((5-(1H-Pyrazol-4-yl)pyridin-2-yl)methyl)-1H-indole-7-carboxamido)cyclopropyl) bicyclo[1.1.1]pentane-1-carboxylic acid 15

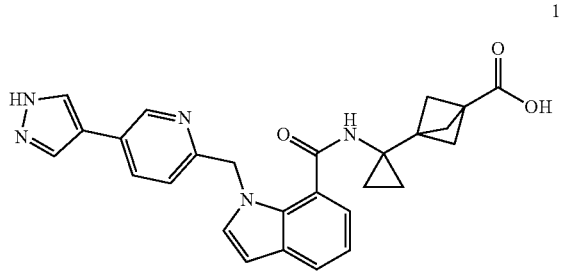

15

In accordance with a preparation method similar to the method described in Example 11, compound 11-0 in Step 1 was replaced with (1H-pyrazol-4-yl)boronic acid, accordingly, compound 15 was obtained as a light yellow solid. MS (ESI): 467.2.

¹H NMR (400 MHz, DMSO-d₆): δ 12.30 (s, 1H), 8.74 (d, J=1.59 Hz, 1H), 8.51-8.47 (m, 1H), 8.32-7.86 (m, 2H), 7.72 (dd, J=17.03, 8.04, 1.71 Hz, 2H), 7.48 (d, J=3.18 Hz, 1H), 7.16-7.13 (m, 1H), 7.10-7.05 (m, 1H), 6.63 (d, J=3.18 Hz, 1H), 6.29 (d, J=8.19 Hz, 1H), 5.62 (s, 2H), 1.68 (s, 6H), 0.56-0.53 (m, 2H), 0.43-0.40 (m, 2H).

Example 16

3-(1-(1-((5-(1-(3-Hydroxypropyl)-1H-pyrazol-4-yl)pyridin-2-yl)methyl)-1H-indole-7-carboxamido)cyclopropyl)bicyclo[1.1.1]pentane-1-carboxylic acid 16

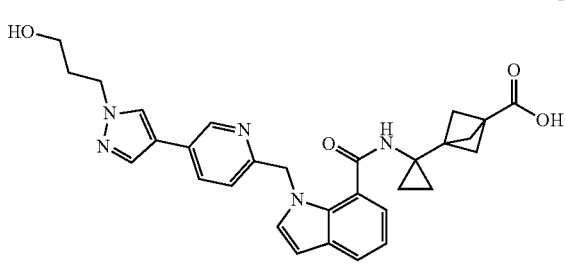

16

In accordance with a preparation method similar to the method described in Example 11, compound 11-0 in Step 1 was replaced with 3-(4-(4,4,5,5-tetramethyl-1,3,2-dioxaborane-2-yl)-1H-pyrazol-1-yl)propan-1-ol, accordingly, compound 16 was obtained as a white solid. MS (ESI): 526.2.

¹H NMR (400 MHz, DMSO-d₆): δ 12.20 (s, 1H), 8.70 (d, J=2.0 Hz, 1H), 8.46 (s, 1H), 8.20 (s, 1H), 7.86 (s, 1H), 7.72-7.67 (m, 2H), 7.48 (d, J=3.1 Hz, 1H), 7.13 (s, 1H), 7.08 (d, J=7.6 Hz, 1H), 6.62 (d, J=2.9 Hz, 1H), 6.29 (d, J=8.1 Hz, 1H), 5.62 (s, 2H), 4.16 (t, J=7.0 Hz, 2H), 3.39 (s, 2H), 1.95-1.89 (m, 2H), 1.64 (s, 6H), 1.24 (s, 1H), 0.57-0.51 (m, 2H), 0.42 (d, J=1.2 Hz, 2H).

Example 17

3-(1-(1-((5-(3-Hydroxypiperidin-1-yl)pyridin-2-yl)methyl)-1H-indole-7-carboxamido)cyclo propyl) bicyclo[1.1.1]pentane-1-carboxylic acid 17

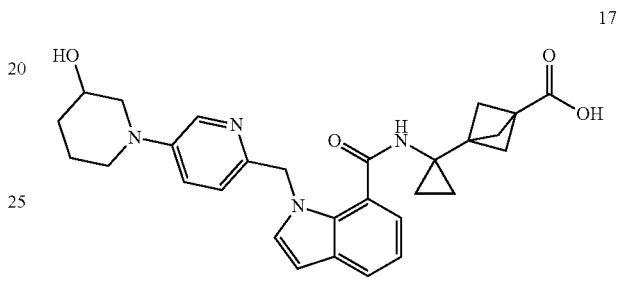

17

In accordance with a preparation method similar to the method described in Example 11, compound 11-0 in Step 1 was replaced with piperidin-3-ol, and Cs₂CO₃ (787 mg, 2.42 mmol), 2-(dimethylamino)acetic acid (25 mg, 242 μmol) and cuprous iodide (70.0 mg, 367 mol) were added in DMSO. The reaction was carried out for 13 hours at 127° C. under a nitrogen atmosphere. The other reaction steps were the same, accordingly, compound 17 was obtained as a pale yellow solid. MS (ESI): 501.1.

¹H NMR (400 MHz, DMSO-d₆): δ 12.20 (s, 1H), 8.46 (s, 1H), 8.13 (d, J=2.29 Hz, 1H), 7.66 (d, J=7.32 Hz, 1H), 7.40 (d, J=3.20 Hz, 1H), 7.12 (d, J=7.32 Hz, 1H), 7.04-7.09 (m, 2H), 6.57 (d, J=3.02 Hz, 1H), 6.29 (d, J=8.51 Hz, 1H), 5.47 (s, 2H), 5.32 (t, J=4.89 Hz, 1H), 3.49-3.60 (m, 4H), 3.17 (d, J=5.03 Hz, 1H), 2.00 (d, J=7.32 Hz, 2H), 1.76 (s, 1H), 1.64 (s, 6H), 1.46 (d, J=2.20 Hz, 1H), 0.55 (s, 2H), 0.41-0.46 (m, 2H).

Example 18

3-(1-(1-((5-Cyclopropylpyridin-2-yl)methyl)-1H-indole-7-carboxamido)cyclopropyl)bicyclo[1.1.1]pentane-1-carboxylic acid 18

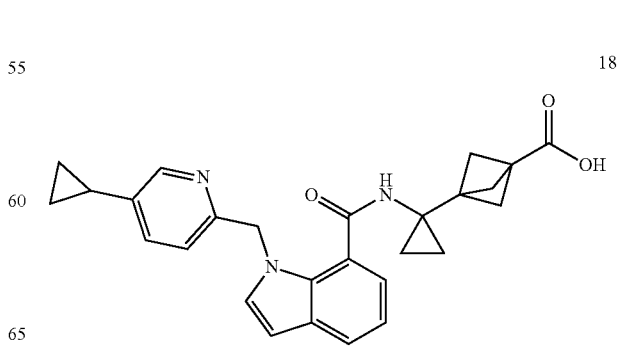

18

In accordance with a preparation method similar to the method described in Example 11, compound 11-0 in Step 1 was replaced with cyclopropylboronic acid, accordingly, compound 18 was obtained as a white solid. MS (ESI): 442.2.

¹H NMR (400 MHz, DMSO-d₆): δ 12.20 (s, 1H), δ 8.43 (s, 1H), 8.28 (d, J=2.3 Hz, 1H), 7.68 (dd, J=1.2, 7.8 Hz, 1H), 7.44 (d, J=3.2 Hz, 1H), 7.20-7.11 (m, 2H), 7.09-7.03 (m, 1H), 6.60 (d, J=3.2 Hz, 1H), 6.20 (d, J=7.7 Hz, 1H), 5.58 (s, 2H), 1.88 (s, 1H), 1.64 (s, 6H), 0.97-0.89 (m, 2H), 0.66-0.61 (m, 2H), 0.59-0.54 (m, 2H), 0.40-0.31 (m, 2H).

Example 19

3-(1-(1-((5-(2-(Hydroxymethyl)phenyl)pyridin-2-yl)methyl)-1H-indole-7-carboxamido)cyclopropyl)bicyclo[1.1.1]pentane-1-carboxylic acid 19

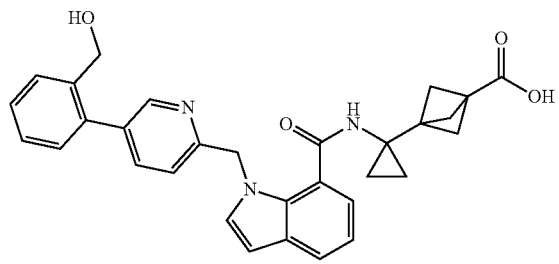

19

In accordance with a preparation method similar to the method described in Example 11, compound 11-0 in Step 1 was replaced with (2-(hydroxymethyl)phenyl)boronic acid, accordingly, compound 19 was obtained as a white solid. MS (ESI): 508.2.

¹H NMR (400 MHz, DMSO-d₆): δ 12.20 (s, 1H), 8.53 (s, 1H), 8.48 (d, J=1.75 Hz, 1H), 7.73 (dd, J=7.88, 1.00 Hz, 1H), 7.61 (dd, J=8.07, 2.19 Hz, 1H), 7.53-7.58 (m, 2H), 7.41 (td, J=7.47, 1.19 Hz, 1H), 7.34 (td, J=7.47, 1.19 Hz, 1H), 7.19 (s, 1H), 7.17 (s, 1H), 7.08-7.12 (m, 1H), 6.66 (d, J=3.13 Hz, 1H), 6.29 (d, J=8.00 Hz, 1H), 5.74 (s, 2H), 4.34 (s, 2H), 1.72 (s, 6H), 0.54-0.59 (m, 2H), 0.32-0.37 (m, 2H).

Example 20

3-(1-(1-(Benzofuran-2-ylmethyl)-1H-indole-7-carboxamido)ethyl)bicyclo[1.1.1]pentane-1-carboxylic acid 20, (S)-3-(1-(1-(benzofuran-2-ylmethyl)-1H-indole-7-carboxamido)ethyl)bicyclo[1.1.1]pentane-1-carboxylic acid 20-5 and (R)-3-(1-(1-(benzofuran-2-ylmethyl)-1H-indole-7-carboxamido)ethyl)bicyclo[1.1.1]pentane-1-carboxylic acid 20-6

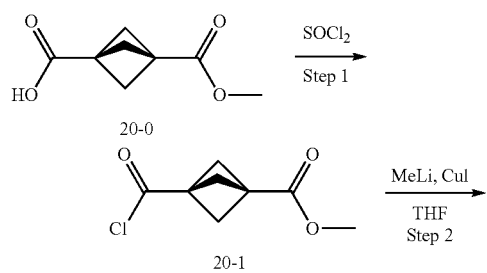

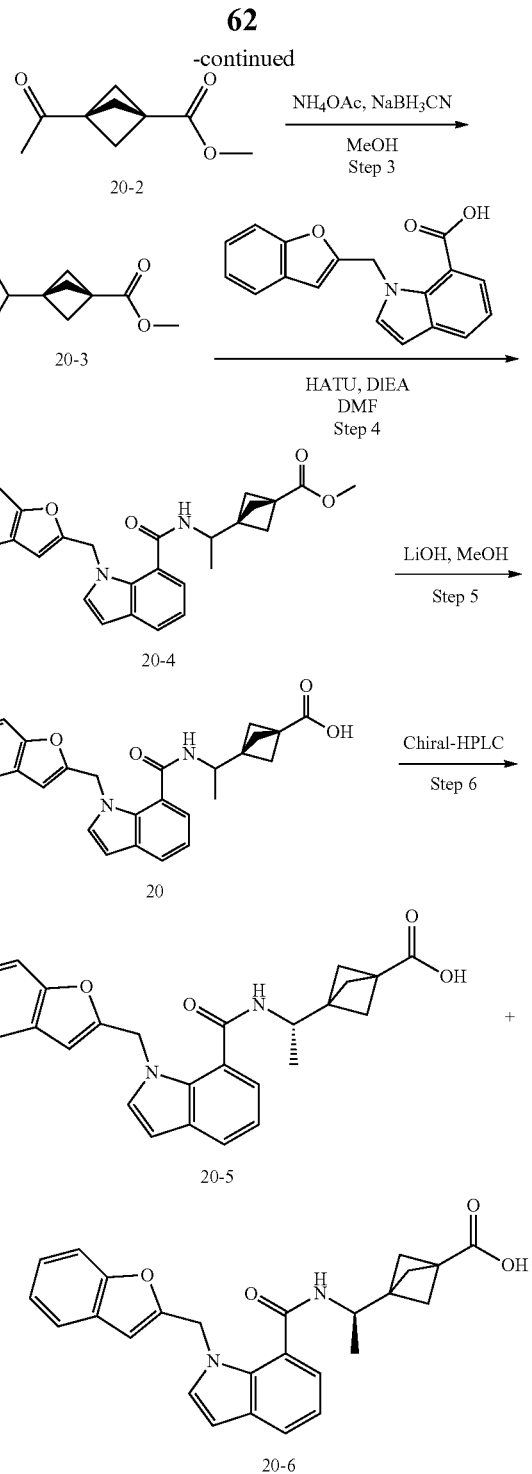

Step 1: Preparation of methyl 3-(chlorocarbonyl)bicyclo[1.1.1]pentane-1-carboxylate 20-1

A solution of 3-(methoxycarbonyl)bicyclo[1.1.1]pentane-1-carboxylic acid (100 mg, 0.59 mmol) in SOCl₂ (2 mL) was stirred at 80° C. for 1.5 hours. The reaction mixture was concentrated to obtain compound 20-1 (110 mg, yield: 100%) as a white solid, which was used in the next step without purification.

Step 2: Preparation of methyl 3-acetylbicyclo[1.1.1]pentane-1-carboxylate 20-2

MeLi (0.88 mL, 1.6 M in THF, 1.4 mmol) was added dropwise to a suspension of CuI (134 mg, 0.71 mmol) in anhydrous THF (2 mL) at 0° C. under a nitrogen atmosphere. The reaction mixture was cooled to −78° C., and a solution of compound 20-1 (110 mg, 0.59 mmol) in anhydrous THF (2 mL) was added dropwise. The reaction mixture was stirred at −78° C. for 2 hours. Methanol (0.6 mL) was added, and the resulting mixture was warmed up to room temperature. Saturated $NH_4Cl$ solution (10 mL) was added, and the resulting mixture was extracted with EtOAc (20 mL×3). The combined organic layer was washed with water and brine, dried over anhydrous $Na_2SO_4$, filtered and concentrated. The resulting residue was purified by column chromatography (silica gel, eluted with hexane/EtOAc from 5:1 to 2:1 (v/v)) to obtain compound 20-2 (75 mg, yield: 76%), as a pale yellow solid. MS (ESI): 169.1 $[M+1]^+$.

1H NMR (400 MHz, $CDCl_3$) δ: 3.62 (s, 3H), 2.24 (s, 6H), 2.07 (s, 3H).

Step 3: Preparation of methyl 3-(1-aminoethyl)bicyclo[1.1.1]pentane-1-carboxylate 20-3

A mixture of compound 20-2 (293 mg, 1.74 mmol), $NH_4OAc$ (805 mg, 10.46 mmol) and $NaBH_3CN$ (164 mg, 2.61 mmol) in MeOH (6 mL) was stirred at room temperature for 2 hours. LCMS showed that the reaction was complete. The reaction mixture was concentrated, and purified by column chromatography (silica gel, eluted with DCM/MeOH from 30:1 (v/v) to 10:1 (v/v)) to obtain compound 20-3 (800 mg, crude product, yield: 100%) as a transparent oil. MS (ESI): 170.1 $[M+1]^+$.

Step 4: Preparation of methyl 3-(1-(1-(benzofuran-2-ylmethyl)-1H-indole-7-carboxamido)ethyl)bicyclo[1.1.1]pentane-1-carboxylate 20-4

DIPEA (197 mg, 1.53 mmol) was added to a solution of compound 20-3 (150 mg, 0.51 mmol), 1-(benzofuran-2-ylmethyl)-1H-indole-7-carboxylic acid (800 mg, 0.51 mmol) and HATU (232 mg, 0.61 mmol) in DMF (6 mL). The resulting mixture was stirred at room temperature overnight. LCMS showed that the reaction was complete. The reaction mixture was poured into water (5 mL), and extracted with ethyl acetate (15 mL×3). The combined organic layer was washed with brine, dried over $Na_2SO_4$, filtered and concentrated under vacuum. The resulting residue was purified by column chromatography (silica gel, eluted with PE/EtOAc from 5:1 to 1:2 (v/v)) to obtain compound 20-4 (117 mg, yield: 52%) as a pale yellow solid. MS (ESI): 443.0 $[M+1]^+$.

Step 5: Preparation of 3-(1-(1-(benzofuran-2-ylmethyl)-1H-indole-7-carboxamido)ethyl)bicyclo[1.1.1]pentane-1-carboxylic acid 20

$LiOH \cdot H_2O$ (2 M, 0.15 mL, 0.30 mmol) was added to a solution of compound 20-4 (106 mg, 0.24 mmol) in MeOH (4 mL). The resulting mixture was stirred at 50° C. overnight. LCMS showed that the reaction was complete. The reaction mixture was acidified to pH~5 with 1 M HCl, and extracted with ethyl acetate (15 mL×3). The combined organic layer was washed with brine, dried over $Na_2SO_4$, filtered and concentrated under vacuum to obtain compound 20 (80 mg, yield: 78%) as an off-white solid. MS (ESI): 429.0 $[M+1]^+$.

$^1$H NMR (400 MHz, DMSO-$d_6$) δ: 12.29 (brs, 1H), 8.32 (d, J=6.0 Hz, 1H), 7.70 (d, J=7.2 Hz, 1H), 7.57 (d, J=3.2 Hz, 1H), 7.50 (d, J=8.0 Hz, 1H), 7.44 (d, J=8.0 Hz, 1H), 7.22-7.09 (m, 4H), 6.61 (d, J=2.8 Hz, 1H), 6.39 (s, 1H), 5.91 (d, J=16.0 Hz, 1H), 5.68 (d, J=16.0 Hz, 1H), 4.18-4.11 (m, 1H), 1.82 (s, 6H), 0.93 (d, J=6.8 Hz, 3H).

Step 6: Preparation of (R)-3-(1-(1-(benzofuran-2-ylmethyl)-1H-indole-7-carboxamido)ethyl)bicyclo[1.1.1]pentane-1-carboxylic acid 20-5 and (S)-3-(1-(1-(benzofuran-2-ylmethyl)-1H-indole-7-carboxamido)ethyl)bicyclo[1.1.1]pentane-1-carboxylic acid 20-6

Racemate 20 (80 mg, 0.19 mmol) was separated by chiral HPLC (CHIRALPAK AD-3 (4.6×100 mm, 3 m), mobile phase: MeOH, column temperature: 35° C.) to obtain compounds 20-5 (20 mg, Rt=1.68 min, yield: 50%) and 20-6 (20 mg, Rt=3.09 min, yield: 50%), both of which were white solids.

Compound 20-5, MS (ESI): 429.0 $[M+1]^+$.

$^1$H NMR (400 MHz, DMSO-$d_6$) δ: 12.29 (brs, 1H), 8.34 (d, J=6.0 Hz, 1H), 7.70 (d, J=7.2 Hz, 1H), 7.57 (d, J=3.2 Hz, 1H), 7.50 (d, J=8.0 Hz, 1H), 7.44 (d, J=8.0 Hz, 1H), 7.22-7.06 (m, 4H), 6.61 (d, J=2.8 Hz, 1H), 6.39 (s, 1H), 5.92 (d, J=16.0 Hz, 1H), 5.68 (d, J=16.0 Hz, 1H), 4.18-4.11 (m, 1H), 1.82 (s, 6H), 0.93 (d, J=6.8 Hz, 3H).

Compound 20-6, MS (ESI): 429.0 $[M+1]^+$.

$^1$H NMR (400 MHz, DMSO-$d_6$) δ: 12.46 (brs, 1H), 8.34 (d, J=8.0 Hz, 1H), 7.69 (d, J=8.0 Hz, 1H), 7.57 (d, J=3.2 Hz, 1H), 7.50 (d, J=6.8 Hz, 1H), 7.44 (d, J=8.0 Hz, 1H), 7.22-7.05 (m, 4H), 6.61 (d, J=3.2 Hz, 1H), 6.39 (s, 1H), 5.92 (d, J=16.4 Hz, 1H), 5.68 (d, J=16.4 Hz, 1H), 4.18-4.11 (m, 1H), 1.83 (s, 6H), 0.93 (d, J=6.8 Hz, 3H).

Example 21

3-(1-(1-((5-Fluorobenzofuran-2-yl)methyl)-1H-indole-7-carboxamido)cyclopropyl)bicyclo[1.1.1]pentane-1-carboxylic acid 21

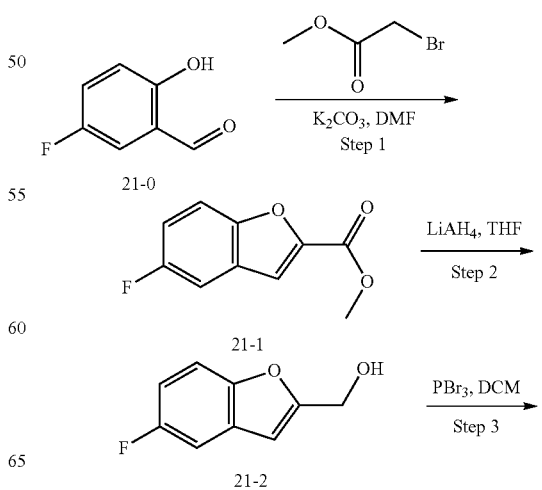

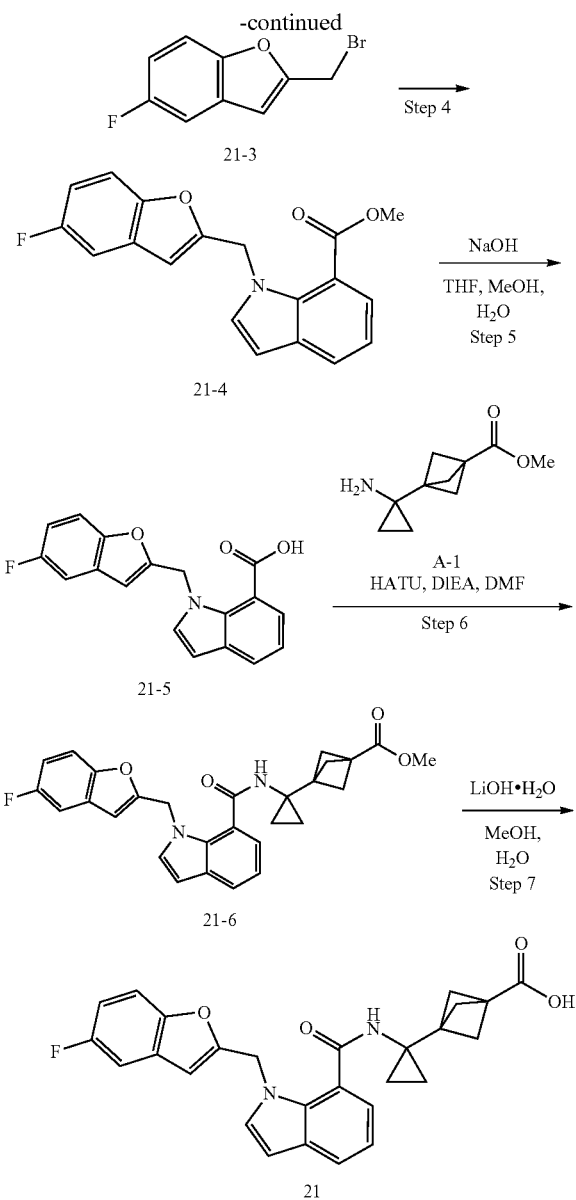

Step 2: Synthesis of (5-fluorobenzofuran-2-yl)methanol 21-2

Compound 21-1 (2.1 g, 10.82 mmol) and tetrahydrofuran (50 mL) were added to a reaction flask. The resulting mixture was stirred under a nitrogen atmosphere, and cooled to 0° C. in an ice bath. Lithium tetrahydroaluminum (2.05 g, 54.10 mmol) was slowly added thereto in batches, and the temperature was kept at 0° C. After completion of the addition, the reaction solution was stirred at 0° C. for 1 hour. Water (2 mL), 15% aqueous sodium hydroxide solution (2 mL) and water (4 mL) were successively and slowly added dropwise to the reaction solution, and the temperature was kept at 0° C. After completion of the addition, the reaction solution was warmed up to room temperature, and stirred for 1 hour. The reaction solution was filtered, and the filtrate was collected and dried over anhydrous sodium sulfate to obtain compound 21-2 (1.71 g, yield: 95.1%) as a colorless oil. MS (ESI): 149.2 [M+1]$^+$.

Step 3: Synthesis of 2-(bromomethyl)-5-fluorobenzofuran 21-3

Compound 21-2 (1.0 g, 6.02 mmol) and anhydrous dichloromethane (20 mL) were added to a reaction flask. The resulting mixture was stirred and cooled to 0° C. in an ice bath. Phosphorus tribromide (1.8 g, 6.62 mmol) was slowly added dropwise thereto. After completion of the addition, the reaction mixture was stirred at room temperature for 1 hour. TLC (petroleum ether:ethyl acetate=5:1) showed that the reaction was completed, and the solvent was removed under reduced pressure. The resulting residue was adjusted to the pH 8-9 with saturated aqueous sodium bicarbonate solution, and extracted with dichloromethane (20 ml×3). The combined organic phase was washed with saturated brine, dried over anhydrous sodium sulfate, and concentrated under reduced pressure to remove the solvent and obtain compound 21-3 (1.3 g, yield: 94.3%) as a yellow solid. MS (ESI): 228.0 [M+1]$^+$.

Steps 4 to 7

In accordance with the method described in Example 1, 1-(bromomethyl)-4-(trifluoromethyl)benzene was replaced with compound 21-3, accordingly, compound 21 was obtained as an off-white solid. MS (ESI): 459.1 [M+1]$^+$.

$^1$H NMR (400 MHz, DMSO-D$_6$): δ 12.24 (s, 1H), 8.72 (s, 1H), 7.77 (d, J=8.0 Hz, 1H), 7.46-7.52 (m, 2H), 7.22-7.29 (m, 2H), 7.02-7.09 (m, 2H), 6.60 (d, J=3.2 Hz, 1H), 6.21 (s, 1H), 5.75 (s, 2H), 1.69 (s, 6H), 0.59-0.62 (m, 2H), 0.45-0.48 (m, 2H).

Example 22

3-(1-(1-(((6-Fluorobenzofuran-2-yl)methyl)-1H-indole-7-carboxamido)cyclopropyl)bicyclo[1.1.1]pentane-1-carboxylic acid 22

Step 1: Synthesis of methyl 5-fluorobenzofuran-2-carboxylate 21-1

5-Fluoro-2-hydroxybenzaldehyde 21-0 (3.0 g, 21.41 mmol), methyl bromoacetate (4.91 g, 32.12 mmol), potassium carbonate (5.91 g, 42.82 mmol) and N,N-dimethylformamide (120 mL) were successively added to a reaction flask. The reaction solution was heated to 80° C. and stirred overnight under a nitrogen atmosphere. After completion of the reaction, the reaction solution was poured into water and extracted with ethyl acetate (200 mL×3). The organic phase was washed successively with water and saturated brine, dried over anhydrous sodium sulfate, and concentrated under reduced pressure to remove the solvent. The resulting crude product was purified by silica gel column [eluent: petroleum ether-ethyl acetate (20:1-5:1)] to obtain compound 21-1 (2.1 g, yield: 51.8%) as a yellow solid. MS (ESI): 195.2 [M+1]$^+$.

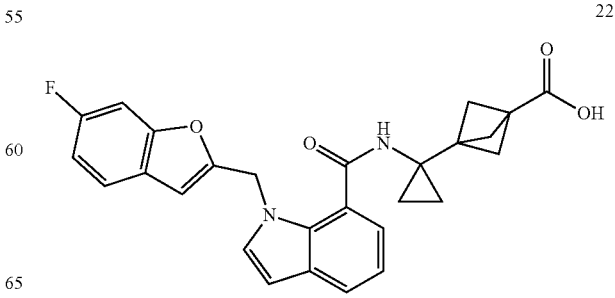

In accordance with the method described in Example 21, compound 21-0 was replaced with 4-fluoro-2-hydroxybenzaldehyde, accordingly, compound 22 was obtained as an off-white solid. MS (ESI): 459.1 [M+1]+.

$^1$H NMR (400 MHz, DMSO-D$_6$): δ 12.24 (s, 1H), 8.72 (s, 1H), 7.69 (d, J=8.0 Hz, 1H), 7.46-7.67 (m, 2H), 7.39-7.42 (d, J=8.0, 1H), 7.22-7.24 (d, J=7.9, 1H), 7.02-7.09 (m, 2H), 7.03 (s, 1H), 6.64 (d, J=3.2 Hz, 1H), 6.6 (s, 1H), 5.75 (s, 2H), 1.69 (s, 6H), 0.64-0.62 (m, 2H), 0.44-0.46 (m, 2H).

Example 23

3-(1-(1-(Benzo[d]oxazol-2-ylmethyl)-1H-indole-7-carboxamido)cyclopropyl)bicyclo[1.1.1]pentane-1-carboxylic acid 23

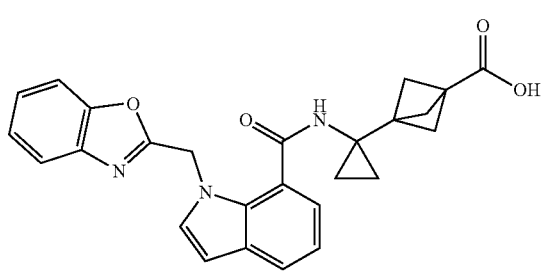

In accordance with the method described in Example 21, compound 21-0 was replaced with methyl benzo[d]oxazole-2-carboxylate, accordingly, compound 23 was obtained as a white solid. MS (ESI): 442.2[M+1]+.

$^1$H NMR (400 MHz, DMSO-d6) δ: 12.20 (s, 1H), 8.57 (s, 1H), 7.87 (d, J=7.6 Hz, 2H), 7.69-7.6 (m, 2H), 7.56-7.52 (m, 2H), 7.34-7.18 (m, 2H), 6.67 (s, 1H), 6.23 (s, 2H), 1.72 (s, 6H), 0.56-0.47 (m, 4H).

Example 24

3-(1-(1-(Benzo[d]thiazol-2-ylmethyl)-1H-indole-7-carboxamido)cyclopropyl)bicyclo[1.1.1]pentane-1-carboxylic acid 24

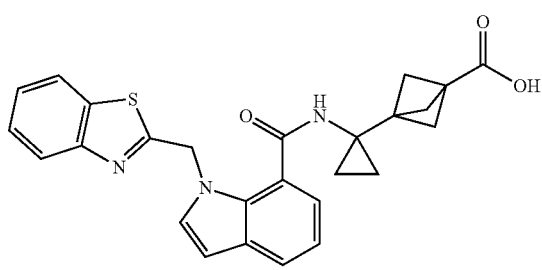

In accordance with the method described in Example 21, compound 21-0 was replaced with methyl benzo[d]thiazol-2-carboxylate, accordingly, compound 24 was obtained as a white solid. MS (ESI): 458.2[M+1]+.

$^1$H NMR (400 MHz, DMSO-d6) δ: 12.20 (s, 1H), 8.57 (s, 1H), 7.87 (d, J=7.6 Hz, 2H), 7.46-7.42 (m, 2H), 7.34-7.18 (m, 2H), 6.67 (s, 1H), 6.03 (s, 2H), 1.72 (s, 6H), 0.56-0.47 (m, 4H).

Example 25

3-(1-(1-(Benzofuran-2-ylmethyl)-1H-pyrrolo[3,2-c]pyridine-7-carboxamido)cyclopropyl)bicyclo[1.1.1]pentane-1-carboxylic acid 25

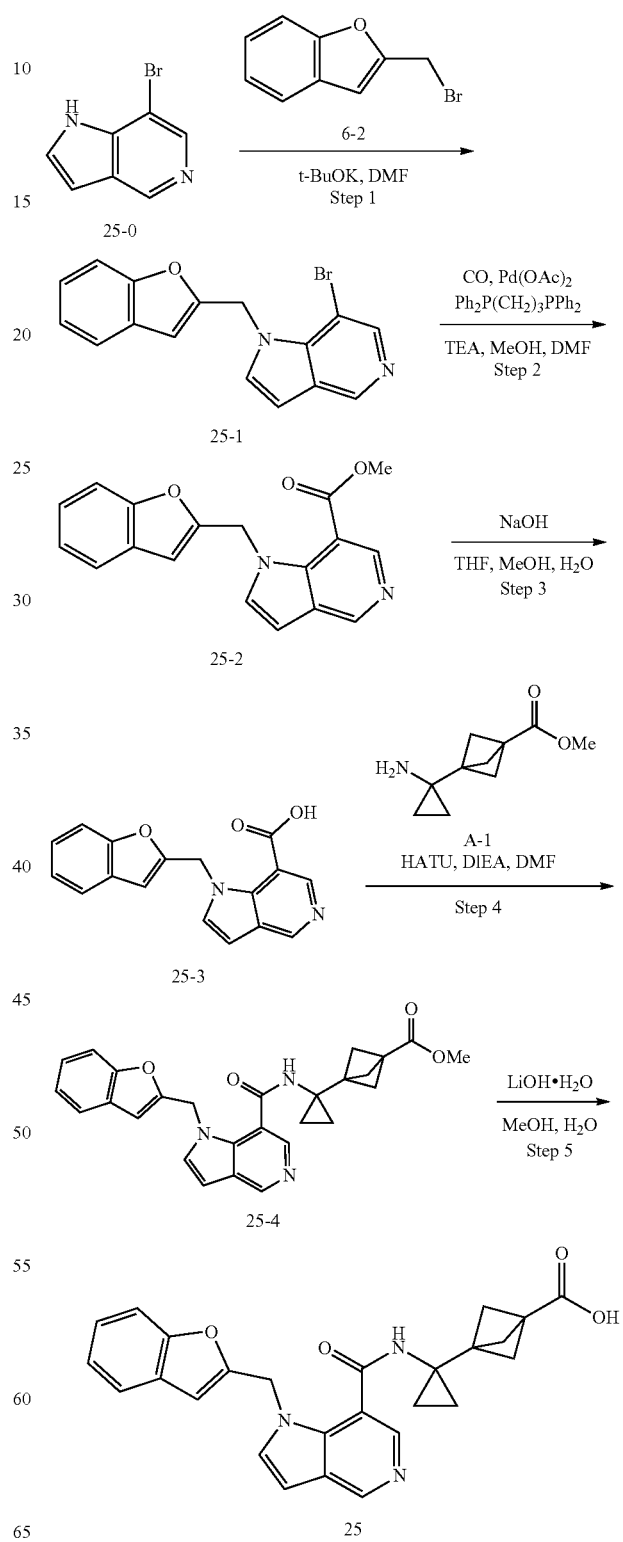

Step 1: Synthesis of 1-(benzofuran-2-ylmethyl)-7-bromo-1H-pyrrolo[3,2-c]pyridine 25-1 t-BuOK (1.53 g, 13.63 mmol) was added to a solution of 7-bromo-1H-pyrrolo[3,2-c]pyridine 25-0 (1.79 g, 9.09 mmol) in DMF (80 mL) at 0° C., followed by the addition of compound 6-2 (2.5 g, crude product, 11.36 mmol). The resulting mixture was stirred at room temperature overnight. The reaction mixture was poured into water (200 ml), and extracted with ethyl acetate (100 ml×2). The combined organic layer was washed with brine, dried over $Na_2SO_4$, filtered and concentrated under vacuum. The resulting crude product was purified by column chromatography (petroleum ether/ethyl acetate=10/1-5/1) to obtain compound 25-1 (2.5 g, yield: 84%) as a yellow oil. MS (ESI): 327.0 $[M+1]^+$.

Step 2: Synthesis of methyl 1-(benzofuran-2-ylmethyl))-1H-pyrrolo[3,2-c]pyridine-7-carboxylate 25-2

$Pd(OAc)_2$ (171 mg, 0.764 mmol), $Ph_2P(CH_2)_3PPh_2$ (318 mg, 0.764 mmol) and TEA (2.31 g, 22.9 mmol) were added to a solution of compound 25-1 (2.5 g, 7.64 mmol) in MeOH (21 ml) and DMF (14 ml). The resulting mixture was stirred for 48 hours under a CO atmosphere at 80° C. The reaction mixture was poured into water (100 ml), and extracted with ethyl acetate (100 ml×2). The combined organic layer was washed with brine, dried over $Na_2SO_4$, filtered and concentrated under vacuum. The resulting crude product was purified by column chromatography (petroleum ether/ethyl acetate=10/1~2/1) to obtain compound 25-2 (1.3 g, yield: 55%) as a yellow oil. MS (ESI): 307.2 $[M+1]^+$.

$^1$H NMR (400 MHz, DMSO-$d_6$) δ: 9.02 (s, 1H), 8.58 (s, 1H), 7.95 (s, 1H), 7.77 (d, J=3.6 Hz, 1H), 7.56 (dd, J=7.2, 0.8 Hz, 1H), 7.44-7.42 (m, 1H), 7.24-7.18 (m, 2H), 6.85 (d, J=3.6 Hz, 1H), 6.56 (d, J=0.8 Hz, 1H), 5.89 (s, 2H), 3.91 (s, 3H).

Step 3: Synthesis of 1-(benzofuran-2-ylmethyl)-1H-pyrrolo[3,2-c]pyridine-7-carboxylic acid 25-3

An aqueous NaOH solution (2 M, 4.9 mL, 9.8 mmol) was added to a solution of compound 25-2 (2 g, 1.96 mol) in THF (10 mL) and methanol (10 mL). The resulting mixture was stirred at room temperature overnight. The reaction mixture was concentrated to remove MeOH and THF. The resulting residue was poured into water (30.0 mL), and acidified to pH~6 with 1 N aqueous hydrochloric acid solution. The resulting precipitate was collected by filtration to obtain compound 25-3 (350 mg, yield: 61%) as a white solid. MS (ESI): 293.0 $[M+1]^+$.

$^1$H NMR (400 MHz, DMSO-$d_6$) δ: 13.60 (brs, 1H), 9.02 (s, 1H), 8.61 (s, 1H), 7.77 (d, J=3.2 Hz, 1H), 7.54 (dd, J=7.6, 0.8 Hz, 1H), 7.43 (t, J=7.6 Hz, 1H), 7.26-7.16 (m, 2H), 6.86 (d, J=3.2 Hz, 1H), 6.50 (s, 1H), 6.01 (s, 2H).

Step 4: Synthesis of methyl 3-(1-(1-(1-(benzofuran-2-ylmethyl)-1H-pyrrolo[3,2-c]pyridine-7-carboxamido)cyclopropyl)bicyclo[1.1.1]pentane-1-carboxylate 25-4

DIPEA (77 mg, 0.6) was added to a solution of compound 25-3 (60 mg, 0.2 mmol), compound A-1 (41 mg, 0.22 mmol) and HATU (114 mg, 0.3 mmol) in DMF (5 mL). The resulting mixture was stirred at room temperature overnight. The reaction mixture was poured into water (10 mL), and extracted with ethyl acetate (10 mL×3). The combined organic layer was washed with brine, dried over $Na_2SO_4$, filtered and concentrated under vacuum. The resulting crude product was purified by column chromatography (petroleum ether/ethyl acetate=10/1~2/1) to obtain compound 25-4 (60 mg, yield: 64%) as a yellow oil. MS (ESI): 456.0 $[M+1]^+$.

Step 5: Synthesis of 3-(1-(1-(benzofuran-2-ylmethyl)-1H-pyrrolo[3,2-c]pyridine-7-carboxamido)cyclopropyl)bicyclo[1.1.1]pentane-1-carboxylic acid 25

An aqueous solution of $LiOH \cdot H_2O$ (2 M, 0.33 mL, 0.66 mmol) was added to a solution of compound 25-4 (60 mg, 0.13 mmol) in MeOH (3 mL). The resulting mixture was stirred at 50° C. overnight. The reaction mixture was concentrated to remove MeOH. The resulting residue was acidified to pH~5 with 1 M aqueous hydrochloric acid solution. The resulting precipitate was collected by filtration to obtain compound 25 (30 mg, yield: 51%) as a white solid. MS (ESI): 441.1 $[M+1]^+$. MS (ESI): 442.2 $[M+1]^+$.

$^1$H NMR (400 MHz, DMSO-$d_6$) δ: 12.25 (s, 1H), 8.99 (s, 1H), 8.92 (s, 1H), 8.30 (s, 1H), 7.64 (d, J=3.6 Hz, 1H), 7.49 (d, J=7.2 Hz, 1H), 7.43 (d, J=8.0 Hz, 1H), 7.25-7.15 (m, 2H), 6.78 (d, J=3.2 Hz, 1H), 6.31 (s, 1H), 5.82 (s, 2H), 1.76 (s, 6H), 0.64 (t, J=7.6 Hz, 2H), 0.53 (t, J=1.6 Hz, 2H).

Example 26

3-(1-(1-(Benzofuran-2-ylmethyl)-1H-pyrrolo[3,2-c]pyridine-7-carboxamido)ethyl)bicyclo[1.1.1]pentane-1-carboxylic acid 26, (S)-3-(1-(1-(benzofuran-2-ylmethyl)-1H-pyrrolo[3,2-c]pyridine-7-carboxamido)ethyl)bicyclo[1.1.1]pentane-1-carboxylic acid 26-1, (R)-3-(1-(1-(benzofuran-2-ylmethyl)-1H-pyrrolo[3,2-c]pyridine-7-carboxamido)ethyl)bicyclo[1.1.1]pentane-1-carboxylic acid 26-2

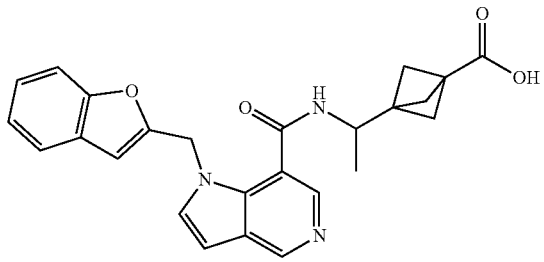

26

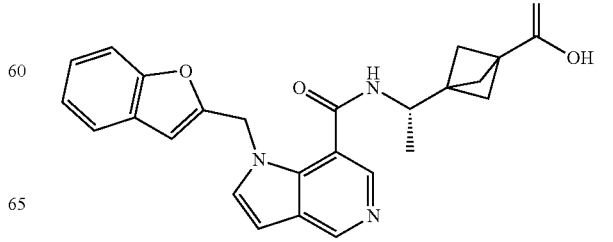

26-1

26-2

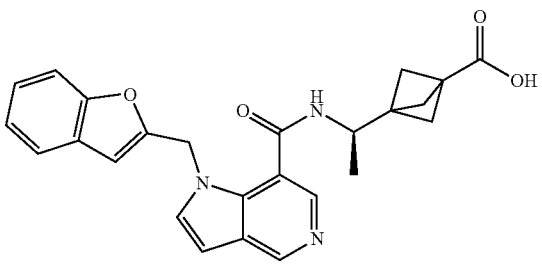

In accordance with the method described in Example 23, compound A1 was replaced with compound 21-3, accordingly, compound 26 was obtained as an off-white solid. MS (ESI): 430.1 [M+1]$^+$.

$^1$H NMR (400 MHz, DMSO-d$_6$) δ: 12.29 (s, 1H), 8.92 (s, 1H), 8.56 (d, J=8.4 Hz, 1H), 8.27 (s, 1H), 7.69 (d, J=3.2 Hz, 1H), 7.51 (d, J=7.2 Hz, 1H), 7.43 (d, J=8.4 Hz, 1H), 7.24-7.16 (m, 2H), 6.78 (d, J=3.2 Hz, 1H), 6.47 (s, 1H), 5.92 (d, J=16.4 Hz, 1H), 5.74 (d, J=16.4 Hz, 1H), 4.15 (t, J=7.2 Hz, 1H), 1.83 (s, 6H), 0.94 (d, J=6.8 Hz, 3H).

Racemate 26 (80 mg, 0.19 mmol) was separated by chiral HPLC (CHIRALPAK AD-3 (4.6×100 mm, 3 m), mobile phase: MeOH) to obtain compounds 26-1 (Rt=1.68 min, 20 mg, yield: 50%) and 26-2 (Rt=3.09 min, 20 mg, yield: 50%), both of which were white solids.

Compound 26-1 was a white solid. MS (ESI): 430.1 [M+1]$^+$.

$^1$H NMR (400 MHz, DMSO-d$_6$) δ: 12.29 (s, 1H), 8.92 (s, 1H), 8.56 (d, J=8.4 Hz, 1H), 8.27 (s, 1H), 7.69 (d, J=3.2 Hz, 1H), 7.51 (d, J=7.2 Hz, 1H), 7.43 (d, J=8.4 Hz, 1H), 7.24-7.16 (m, 2H), 6.78 (d, J=3.2 Hz, 1H), 6.47 (s, 1H), 5.92 (d, J=16.4 Hz, 1H), 5.74 (d, J=16.4 Hz, 1H), 4.15 (t, J=7.2 Hz, 1H), 1.83 (s, 6H), 0.94 (d, J=6.8 Hz, 3H).

Compound 26-2 was a white solid. MS (ESI): 430.1 [M+1]$^+$.

$^1$H NMR (400 MHz, DMSO-d$_6$) δ: 12.29 (s, 1H), 8.92 (s, 1H), 8.56 (d, J=8.0 Hz, 1H), 8.27 (s, 1H), 7.69 (d, J=3.2 Hz, 1H), 7.51 (d, J=7.2 Hz, 1H), 7.43 (d, J=8.4 Hz, 1H), 7.24-7.16 (m, 2H), 6.78 (d, J=3.2 Hz, 1H), 6.47 (s, 1H), 5.92 (d, J=16.4 Hz, 1H), 5.74 (d, J=16.4 Hz, 1H), 4.15 (t, J=7.2 Hz, 1H), 1.83 (s, 6H), 0.94 (d, J=6.8 Hz, 3H).

In accordance with the method described in Example 23, appropriate compounds were used as starting materials, accordingly, the following example compounds were obtained:

Example 29

3-(1-(1-(Benzofuran-2-ylmethyl-d)-1H-indole-7-carboxamido)cyclopropyl)bicyclo[1.1.1]pentane-1-carboxylic acid 29

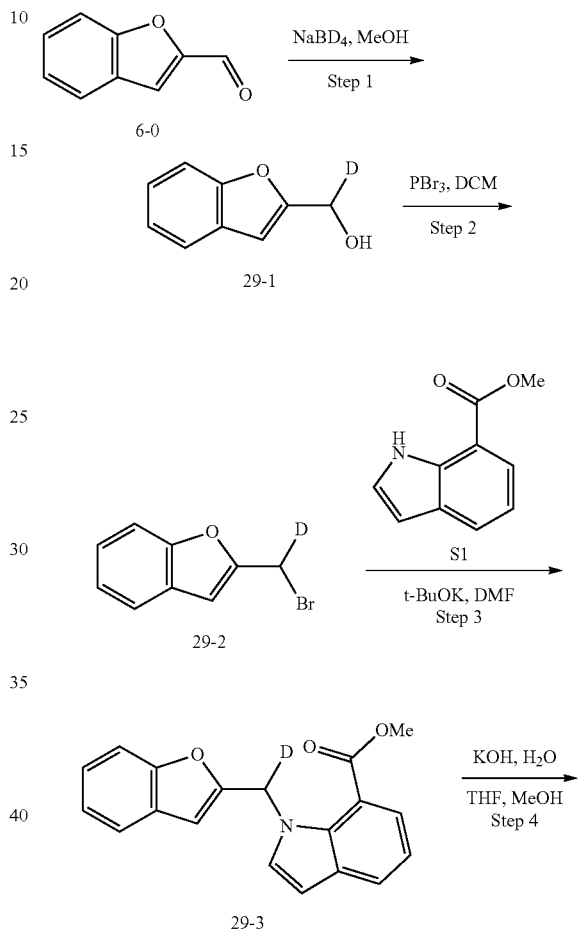

| Example | Chemical name | MS (ESI): [M + 1]$^+$ | $^1$H NMR (400 MHZ, DMSO-d$_6$) |
|---|---|---|---|
| 27 | 3-(1-(1-(((5-Fluoro-benzofuran-2-yl)methyl)-1H-pyrrolo[3,2-c]pyridine-7-carboxamido)cyclopropyl)bicyclo[1.1.1]pentane-1-carboxylic acid | 460.1 | δ: 12.21 (s, 1H), 8.95 (s, 1H), 8.91 (s, 1H), 8.28 (s, 1H), 7.61 (d, J = 4.0 Hz, 1H), 7.45-7.42 (m, 1H), 7.30-7.27 (m, 1H), 7.08-7.03 (m, 1H), 6.76 (d, J = 4.0 Hz, 1H), 6.25 (s, 1H), 5.81 (s, 2H), 1.73 (s, 6H), 0.64-0.61 (m, 2H), 0.51-0.48 (m, 2H) |
| 28 | 3-(1-(1-(((5-(Trifluoro-methyl)benzofuran-2-yl)methyl)-1H-pyrrolo[3,2-c]pyridine-7-carboxamido)cyclopropyl)bicyclo[1.1.1]pentane-1-carboxylic acid | 510.4 | δ: 12.19 (s, 1H), 8.94 (brs, 2H), 8.30 (brs, 1H), 7.92 (s, 1H), 7.66-7.55 (m, 3H), 6.78 (d, J = 3.6 Hz, 1H), 6.38 (s, 1H), 5.86 (s, 2H), 1.72 (s, 6H), 0.63 (q, J = 5.6 Hz, 2H), 0.46 (q, J = 5.6 Hz, 2H) |

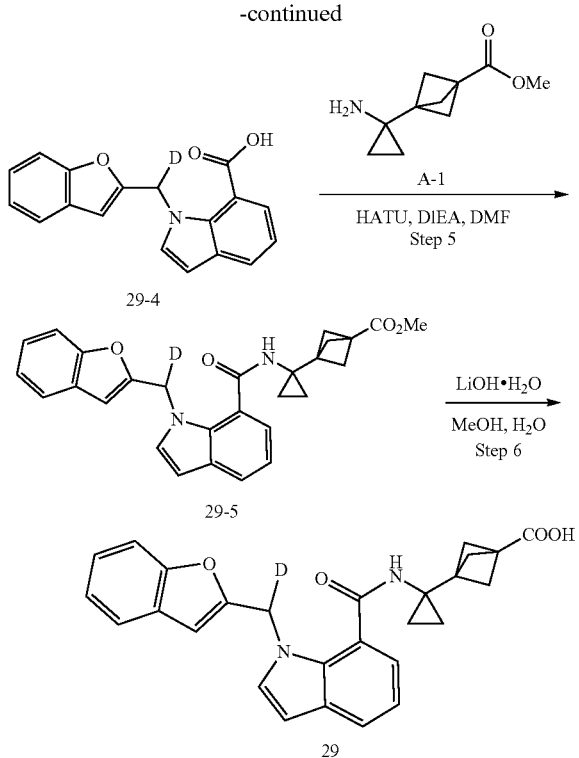

Step 1: Synthesis of benzofuran-2-ylmethan-d-ol 29-1

Compound 6-0 (3 g, 20.5 mmol) and anhydrous methanol (40 ml) were added successively to a reaction flask, and the resulting mixture was cool to 0° C. Sodium borohydride-d₄ (0.545 g, 14.4 mmol) was added thereto in batches, and the the temperature was kept below 25° C. After completion of the addition, the reaction mixture was stirred at room temperature for 1 hour. After completion of the reaction, the solvent was removed under reduced pressure. 1 N aqueous HCl solution (15 ml) was added, and the resulting mixture was stirred at room temperature for 5 minutes. The mixture was adjusted to the pH 8-9 with saturated aqueous sodium bicarbonate solution, and extracted with ethyl acetate (10 ml×3). The combined organic phase was washed with saturated brine, dried over anhydrous sodium sulfate, and concentrated under reduced pressure to remove the solvent and obtain compound 29-1 (3.0 g) as a yellow oil. MS (ESI): 150.1 [M+1]$^+$.

Step 2: Synthesis of 2-(bromomethyl-d)benzofuran 29-2

Compound 29-1 (2.47 g, 16.7 mmol) and dry dichloromethane (32 ml) were added successively to a reaction flask, and the resulting mixture was cool to 0° C. Phosphorus tribromide (1.72 mL, 18.4 mmol) was slowly added dropwise thereto. After completion of the addition, the reaction mixture was warmed up to room temperature and stirred for 1 hour. TLC (petroleum ether:ethyl acetate=9:1) showed that the reaction was completed. The reaction mixture was adjusted to the pH 8-9 with saturated aqueous sodium bicarbonate solution, and extracted with dichloromethane (10 ml×3). The combined organic phase was washed with saturated brine, dried over anhydrous sodium sulfate, and concentrated under reduced pressure to remove the solvent and obtain compound 29-2 (3.31 g, yield: 95%) as a yellow oil. The product was used directly in the next step.

Then, in accordance with the method described in Example 6, compound 6-2 was replaced with compound 29-2, accordingly, compound 29 was obtained as a white solid. MS (ESI): 442.1 [M+1]$^+$.

$^1$H NMR (400 MHz, DMSO-D₆): δ 12.24 (s, 1H), 8.75 (s, 1H), 7.77 (d, J=8.0 Hz, 1H), 7.43-7.30 (m, 2H), 7.28-7.21 (m, 2H), 7.17 (d, J=6.8 Hz, 1H), 7.14-7.09 (m, 1H), 6.64 (d, J=3.2 Hz, 1H), 6.21 (s, 1H), 6.06 (s, 1H), 5.95 (s, 1H), 1.76 (s, 6H), 0.64-0.62 (m, 2H), 0.52-0.49 (m, 2H).

Example 30

3-(1-(1-(1-Benzofuran-2-ylmethyl-d2)-1H-indole-7-carboxamido)cyclopropyl)bicyclo[1.1.1]pentane-1-carboxylic acid 30

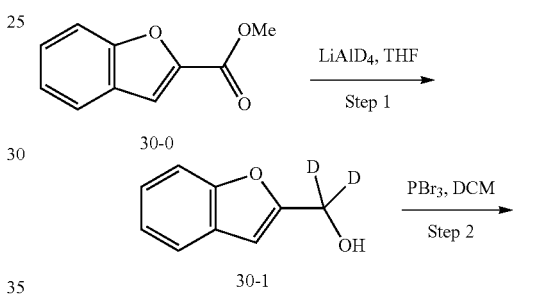

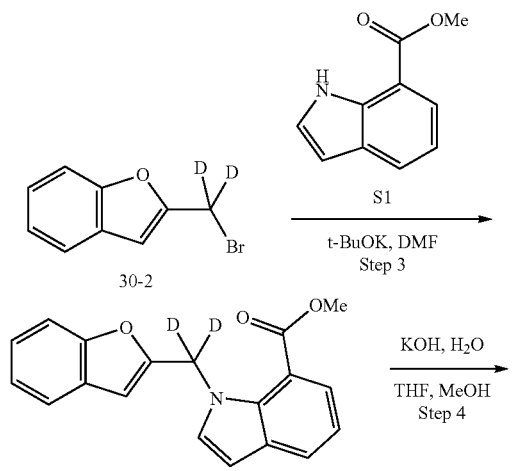

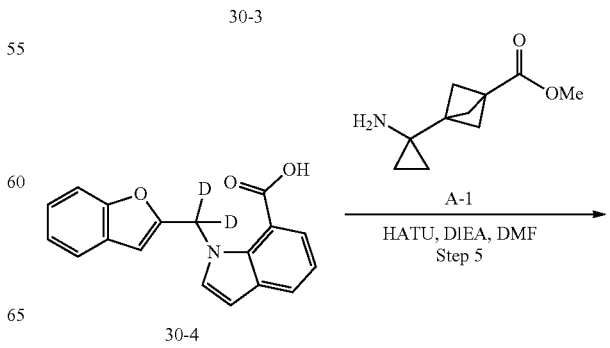

-continued

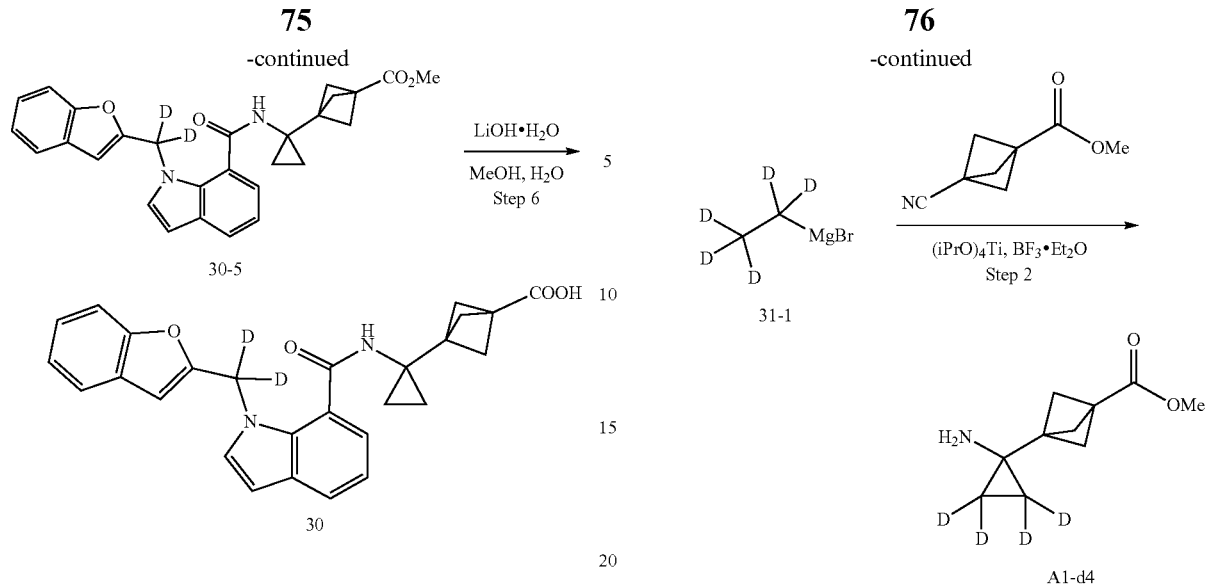

30-5

30

Step 1: Synthesis of benzofuran-2-ylmethan-d2-ol 30-1

Methyl benzofuran-2-carboxylate 30-0 (1.9 g, 10.8 mmol) and tetrahydrofuran (50 mL) were added to a reaction flask. The resulting mixture was stirred under a nitrogen atmosphere, and cooled to 0° C. in an ice bath. Lithium tetrahydroaluminum-d4 (2.2 g, 54.10 mmol) was slowly added thereto in batches, and the temperature was kept at 0° C. After completion of the addition, the reaction solution was stirred at 0° C. for 1 hour. Water (2 mL), 15% aqueous sodium hydroxide solution (2 mL) and water (4 mL) were successively and slowly added dropwise to the reaction solution, and the temperature was kept at 0° C. After completion of the addition, the reaction solution was warmed up to room temperature, and stirred for 1 hour. The reaction solution was filtered, and the filtrate was collected and dried over anhydrous sodium sulfate to obtain compound 30-1 (1.48 g, yield: 91%) as a colorless oil. MS (ESI): 151.2 [M+1]$^+$.

Then, in accordance with the method described in Example 6, compound 6-1 was replaced with compound 30-1, accordingly, compound 30 was obtained as a white solid. MS (ESI): 443.1 [M+1]$^+$.

$^1$H NMR (400 MHz, DMSO-D$_6$): δ 12.24 (s, 1H), 8.75 (s, 1H), 7.77 (d, J=8.0 Hz, 1H), 7.43-7.30 (m, 2H), 7.28-7.21 (m, 2H), 7.17 (d, J=6.8 Hz, 1H), 7.14-7.09 (m, 1H), 6.64 (d, J=3.2 Hz, 1H), 6.21 (s, 1H), 6.06 (s, 1H), 1.76 (s, 6H), 0.64-0.62 (m, 2H), 0.52-0.49 (m, 2H).

Example 31

3-(1-(1-(1-(Benzofuran-2-ylmethyl)-1H-indole-7-carboxamido)cyclopropyl-2,2,3,3-d4)bicyclo[1.1.1]pentane-1-carboxylic acid 31

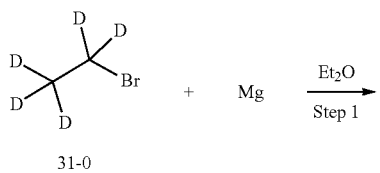

31-0

Step 1: Synthesis of Deuterated Grignard Reagent

Ether (50 ml), bromoethane-d5 (5.6 g, 50 mmol) and magnesium bars (1.32 g, 55 mmol) were added to a dry round bottom flask equipped with a reflux tube. The resulting mixture was stirred under a nitrogen atmosphere. A small amount of iodine was added, and the reaction mixture was heated to reflux. When most of the magnesium bars were consumed, heating was stopped. The resulting deuterated Grignard reagent 31-1 was used for the next step.

Step 2: Synthesis of methyl 3-(1-aminocyclopropyl-2,2,3,3-d4)bicyclo[1.1.1]pentane-1-carboxylate Titanium tetraisopropoxide (5.9 g, 21 mmol, 6 mL, purity: 95%) was added to a solution of methyl 3-cyanobicyclo[1.1.1]pentane-1-carboxylate (3.0 g, 20 mmol) in toluene (50 mL) under a nitrogen atmosphere at −20° C. Compound 31-1 (1 M, 42 mL, 42 mmol) was added dropwise within 30 minutes under a nitrogen atmosphere at −20° C., and the temperature was kept between −20∼−10° C. After stirring for 30 minutes, BF$_3$·Et$_2$O (6 g, 42 mmol, 5.2 mL) was added dropwise. The reaction mixture was stirred at −20° C. for 30 minutes and then at 25° C. for 12 hours. TLC (plate 1: petroleum ether/ethyl acetate=3/1) showed that the raw material (Rf=0.61) was consumed completely, and TLC (plate 2: petroleum ether/ethyl acetate=1/1) showed that a major product (Rf=0.24) was formed. The reaction mixture was quenched by slowly adding aqueous hydrochloric acid (1 N, 30 mL) at 0° C., and then the separated organic layer was discarded. The aqueous phase was basified to pH∼12 with 10 M aqueous sodium hydroxide solution at 0° C., and extracted with ethyl acetate (200 mL×2). The combined organic layer was concentrated, and the resulting residue was purified by column chromatography (silica, petroleum ether/ethyl acetate=20/1 to 1/1) to obtain methyl 3-(1-aminocyclopropyl-2,2,3,3-d4)bicyclo[1.1.1]pentane-1-carboxylate (1.2 g, 6.4 mmol, yield: 32%) as a yellow solid. MS (ESI): 186.1 [M+1]$^+$.

Then, in accordance with the method described in Example 6, compound A1 was replaced with methyl 3-(1-aminocyclopropyl-2,2,3,3-d4)bicyclo[1.1.1]pentane-1-carboxylate A1-d4, accordingly, compound 31 was obtained as an off-white solid. MS (ESI): 445.1 [M+1]$^+$.

¹H NMR (400 MHz, DMSO-D₆): δ 12.24 (s, 1H), 8.75 (s, 1H), 7.77 (d, J=8.0 Hz, 1H), 7.43-7.30 (m, 2H), 7.28-7.21 (m, 2H), 7.17 (d, J=6.8 Hz, 1H), 7.14-7.09 (m, 1H), 6.64 (d, J=3.2 Hz, 1H), 6.21 (s, 1H), 6.06 (s, 1H), 5.75 (s, 2H), 1.76 (s, 6H).

Example 32

3-(1-(1-(1-(Benzofuran-2-ylmethyl)-5-fluoro-1H-indole-7-carboxamido)cyclopropyl)bicyclo[1.1.1]pentane-1-carboxylic acid 32

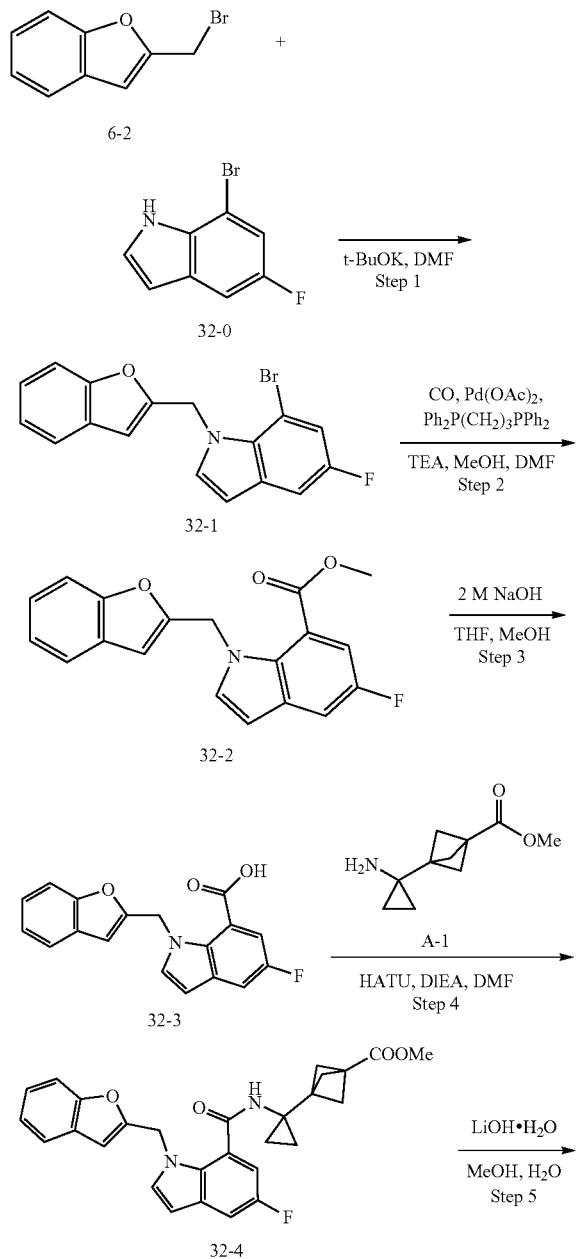

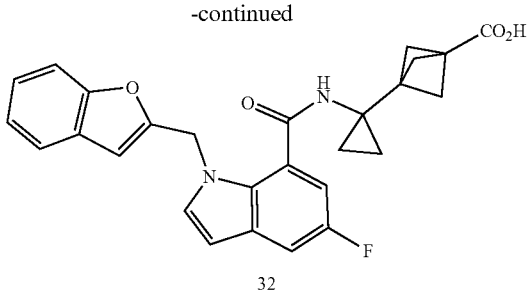

32

Step 1: Synthesis of 1-(benzofuran-2-ylmethyl)-7-bromo-5-fluoro-1H-indole 32-1

Compound 6-2 (251 mg, 1.17 mmol) and N,N-dimethylformamide (10 mL) were added to a reaction flask, and the resulting mixture was cooled to 0° C. in an ice bath under stirring. Potassium tert-butoxide (171 mg, 1.52 mmol) and 7-bromo-5-fluoro-1H-indole 32-0 (295 mg, 1.40 mmol) were added successively. After completion of the addition, the reaction solution was stirred at room temperature for 1 hour. After completion of the reaction, the reaction solution was poured into water and extracted with ethyl acetate (100 mL×3). The organic phase was washed successively with water and saturated brine, dried over anhydrous sodium sulfate, and concentrated under reduced pressure to remove the solvent. The resulting crude product was purified by silica gel column [eluent: petroleum ether-ethyl acetate (20:1-10:1)] to obtain compound 32-1 (390 mg, yield: 96.5%) as a yellow oil. MS (ESI): 344.1[M+1]⁺.

Step 2: Synthesis of methyl 1-(benzofuran-2-ylmethyl)-5-fluoro-1H-indole-7-carboxylate 32-2

Compound 32-1 (390 mg, 1.14 mmol), palladium acetate (26 mg, 0.12 mmol), 1,3-bis(diphenylphosphine)propane (47 mg, 0.12 mmol), methanol (5 mL), N,N-dimethylformamide (10 mL) and triethylamine (344 mg, 3.41 mmol) were added successively to a reaction flask. The reaction system was purged three times by a carbon monoxide balloon, and stirred under a carbon monoxide atmosphere at 90° C. for 48 hours. After completion of the reaction, the reaction solution was poured into water and extracted with ethyl acetate (50 mL×3). The organic phase was washed successively with water and saturated brine, dried over anhydrous sodium sulfate, and concentrated under reduced pressure to remove the solvent. The resulting crude product was purified by silica gel column [eluent: petroleum ether-ethyl acetate (30:1-1:1)] to obtain compound 32-2 (173 mg, yield: 47.1%) as a yellow oil. MS (ESI): 324.1[M+1]⁺.

Step 3: Synthesis of 1-(benzofuran-2-ylmethyl)-5-fluoro-1H-indole-7-carboxylic acid 32-3

Compound 32-2 (173 mg, 0.54 mmol), tetrahydrofuran (5 mL), methanol (5 mL) and 2 M NaOH (1.34 mL, 2.68 mmol) were added successively to a reaction flask, and the resulting mixture was stirred at room temperature overnight. After completion of the reaction, the solvent was removed under reduced pressure. Water (5 mL) was added, and the resulting mixture was adjusted to the pH 1-2 with 1 M aqueous HCl solution. The mixture was filtered, and the filter cake was washed with water to obtain compound 32-3 (156 mg, yield: 94.5%) as a yellow solid. MS (ESI): 310.0[M+1]$^+$.

Step 4: Synthesis of methyl 3-(1-(1-(1-(benzofuran-2-ylmethyl)-5-fluoro-1H-indole-7-carboxamido)cyclopropyl)bicyclo[1.1.1]pentane-1-carboxylate 32-4

Compound 32-3 (90 mg, 0.29 mmol), compound A-1 (63 mg, 0.35 mmol), HATU (133 mg, 0.35 mmol), N,N-dimethylformamide (4 mL) and N,N-diisopropylethylamine (75 mg, 0.58 mmol) were added successively to a reaction flask, and the resulting mixture was stirred at room temperature overnight. After completion of the reaction, the reaction solution was poured into water and extracted with ethyl acetate (10 mL×3). The organic phase was washed successively with water and saturated brine, dried over anhydrous sodium sulfate, and concentrated under reduced pressure to remove the solvent. The resulting crude product was purified by silica gel column [eluent: petroleum ether-ethyl acetate (10:1-2:1)] to obtain compound 32-4 (112 mg, yield: 81.8%) as a yellow solid. MS (ESI): 473.1[M+1]$^+$.

Step 5: Synthesis of 3-(1-(1-(1-(benzofuran-2-ylmethyl)-5-fluoro-1H-indole-7-carboxamido)cyclopropyl)bicyclo[1.1.1]pentane-1-carboxylic acid 32

Compound 32-4 (112 mg, 0.24 mmol), methanol (5 mL) and 2 M aqueous LiOH solution (0.18 mL, 0.36 mmol) were added successively to a reaction flask, and the resulting mixture was heated to 50° C. and stirred overnight. After completion of the reaction, the solvent was removed under reduced pressure. Water (4 mL) was added, and the resulting mixture was adjusted to the pH 5-6 with 1 M aqueous HCl solution. The mixture was filtered, and the filter cake was washed with water and dried to obtain compound 32 (15 mg, yield: 13.9%) as a white solid. MS (ESI): 459.1[M+1]$^+$.

$^1$H NMR (400 MHz, DMSO-d6) δ: 12.24 (s, 1H), 8.83 (s, 1H), 7.58 (d, J=3.2 Hz, 1H), 7.49-7.41 (m, 3H), 7.23-7.12 (m, 2H), 7.05 (dd, J=12.0, 7.2 Hz, 1H), 6.59 (d, J=3.2 Hz, 1H), 6.18 (s, 1H), 5.72 (s, 2H), 1.73 (s, 6H), 0.61 (q, J=4.8 Hz, 2H), 0.49 (q, J=5.6 Hz, 2H).

Biological Activity Assay

Test Example 1: Determination of MCF7 cAMP a) MCF7 cells (ATCC, 6000 cells/well/40 μl) were inoculated into a 384-well cell culture plate containing a medium (DMEM containing 10% FBS and 1×PS), and incubated overnight at 37° C. and 5% $CO_2$.
b) The medium was removed, 40 μl/well of serum-free medium was added, and the cells were incubated at 37° C. and 5% $CO_2$ for 5 hours.
c) The medium was replaced with 18 μL/well of HBSS buffer (Hepes 20 mM, 0.1% BSA, 500 μM IBMX).
d) The compound in DMSO was diluted (1/5 dilution, 9+0 dose).
e) 2 μL of the compound in d) was added to 98 μL of HBSS buffer.
f) 1 μL/well of the diluted compound in e) was added to the cells, with a final starting concentration of 1 μM, and the cells were incubated at 37° C. for 1 hour.
g) The cells were stimulated with 1 μL/well of PGE2 (10 mM DMSO stock solution) (final concentration: 10 nM, and DMSO final concentration: 0.2%), and incubated at 37° C. for 30 minutes.
h) After the incubation, 10 μL/well of cAMP-d2 and 10 μL/well of anti-cAMP were added, RT 1 h.
i) HTRF signals (665 nm/615 nm) were read on Envision.

Data Analysis:
High control: 1 μM E7046
Low control: DMSO
Background: 30 μL/well of lysis buffer+10 μL/well of anti-cAMP
Analytical data: original date—background Inhibition %: 100−100×(high control−analytical data)/(high control−low control)

| ID | MCF7 cAMP $IC_{50}$ (nM) |
|---|---|
| E7046 | 11.2 |
| MF-766 | 1.3 |
| Compound 1 | 2.4 |
| Compound 2 | 0.89 |
| Compound 3 | 7.8 |
| Compound 4 | 61 |
| Compound 5 | 5.5 |
| Compound 6 | 1.1 |
| Compound 7 | 0.13 |
| Compound 8 | 2.9 |
| Compound 9 | 1.1 |
| Compound 10 | 72 |
| Compound 11 | 30 |
| Compound 12 | 62.9 |
| Compound 13 | 11.5 |
| Compound 14 | 24.4 |
| Compound 15 | 14.5 |
| Compound 16 | 215 |
| Compound 17 | 35 |
| Compound 18 | 62.9 |
| Compound 19 | 106.4 |
| Compound 20 | 34 |
| Compound 20-5 | 14 |
| Compound 20-6 | 78 |
| Compound 21 | 0.9 |
| Compound 22 | 1.4 |
| Compound 23 | 8.0 |
| Compound 24 | 12 |
| Compound 25 | 1.5 |
| Compound 26 | 60 |
| Compound 26-1 | 30 |
| Compound 26-2 | >100 |
| Compound 27 | 1.2 |
| Compound 28 | 1.5 |
| Compound 29 | 1.5 |
| Compound 30 | 1.1 |
| Compound 31 | 1.2 |
| Compound 32 | 0.75 |

The results showed that the compounds of the present invention had an excellent activity on inhibiting PGE2/EP4 signal transduction.

Test Example 2: Clearance Assay in Liver Cells

Liver cell type: mouse
Product catalog: M00505
Species: ICR/CD-1
Sex: male
Source: BioreoclmationIVT
Procedures:
1. Preparation of working solution
a. 10 mM stock solutions of test compound and positive control were prepared in an appropriate solvent (DMSO).

b. 198 μL of 50% acetonitrile/50% water and 2 μL of 10 mM solution were mixed in a separate conical tube to obtain 100 μM test compound and positive control.
2. Preparation of liver cells
a. The incubation medium and liver cell thawing medium were placed in a 37° C. water bath, and heated for at least 15 minutes before use.
b. A vial of cryopreserved liver cells was transferred from the storage, ensuring that the vial was kept at a low temperature until the thawing process was conducted. The cells were thawed by placing the vial in a 37° C. water bath and gently shaking the vial for 2 minutes. After completion of the thawing, the vial was sprayed with 70% ethanol and transferred to a biological safety cabinet.
c. The liver cells were transferred to a 50 mL conical tube containing the thawing medium by a large-bore pipette tip. The 50 mL conical tube was placed in a centrifuge and centrifuged at 100 g for 10 minutes. After completion of the centrifugation, the thawing medium was sucked out, and the liver cells were resuspended in enough medium to produce $1.5 \times 10^6$ cells/mL.
3. Procedures of stability assay
a. 198 μL of liver cells were pipetted into each well of a 96-well uncoated plate. The plate was placed in an incubator to warm up the liver cells for 10 minutes.
b. 2 μL of 100 μM test compound or positive control was pipetted into each well of the 96-well uncoated plate to start the reaction. The plate was placed into the incubator at the set time point.
c. The contents of the wells were transferred in 25 μL of aliquots at the time points of 0, 15, 30, 60, 90 and 120 minutes. The aliquot was mixed with 6 volumes (150 μL) of acetonitrile containing internal standard IS (100 nM alprazolam, 200 nM caffeine, and 100 nM tolbutamide) to stop the reaction. The sample was vortex-mixed for 5 minutes, and centrifuged at 3220 g for 45 minutes. An aliquot of 100 μL of supernatant was diluted with 100 μL of ultrapure water, and the mixture was used for LC/MS/MS analysis. All incubations were performed in duplicate.
d. Data analysis
All calculations were performed using Microsoft Excel. The peak area was determined by the extracted ion chromatogram. The in vitro half-life (t½) of the parent compound was determined by the regression analysis of the compound disappearance percentage versus time curve.

The in vitro half-life (t½) was determined by the slope value k:

$$t\frac{1}{2} = 0.693/k$$

The in vitro t½ (in minutes) was converted to in vitro intrinsic clearance (CLint, in $\mu L/min/0.5 \times 10^6$ cells) by using the following equation (average of repeated determinations):

| CLint = kV/N |
|---|
| V = Incubation volume (0.2 mL) |
| N = Number of liver cells per well ($0.1 \times 10^6$ cells) |

| ID | CLint uL/min/$10^6$ cells |
|---|---|
| E7046 | 20.1 |
| MF-766 | 12.5 |
| Compound 1 | 7.1 |
| Compound 2 | 19 |

| CLint = kV/N |
|---|
| V = Incubation volume (0.2 mL) |
| N = Number of liver cells per well ($0.1 \times 10^6$ cells) |

| ID | CLint uL/min/$10^6$ cells |
|---|---|
| Compound 6 | 2.9 |
| Compound 7 | 34 |
| Compound 9 | 20 |
| Compound 21 | 1.93 |
| Compound 25 | 1.35 |

The results showed that the compounds of the present invention had an excellent stability in liver cell, thereby having an excellent metabolic stability.

Test Example 3: Inhibitory Effect of Compound 6 on CT-26 Colorectal Tumor in Mouse Efficacy study on allograft tumor: each 6-week-old female BALB/c mouse was subcutaneously inoculated with $1 \times 10^6$ CT26 cancer cells (National Experimental Cell Resource Sharing Service Platform, Resource Number 3111CCCC). When the tumor reached about 60 to 80 mm³, the tumor-bearing mice were randomly grouped to the vehicle group or treatment group. Compound 6 was administered orally (p.o.) in a 0.5% MC suspension at a dose of 10, 30 or 150 mg/kg, once a day. The mice in the vehicle group were orally administered with distilled water every day, and the administration time was the same as that of the compound 6 group. The tumor volume and body weight were recorded 2 to 3 times a week. The results are shown in FIG. 1 and FIG. 2.

It can be seen from FIG. 1 that when administered alone, different doses of compound 6 and E7046 had a significant inhibitory effect on the growth of CT-26 tumor. At the same dose, compound 6 was significantly better than E7046.

Figure 2:
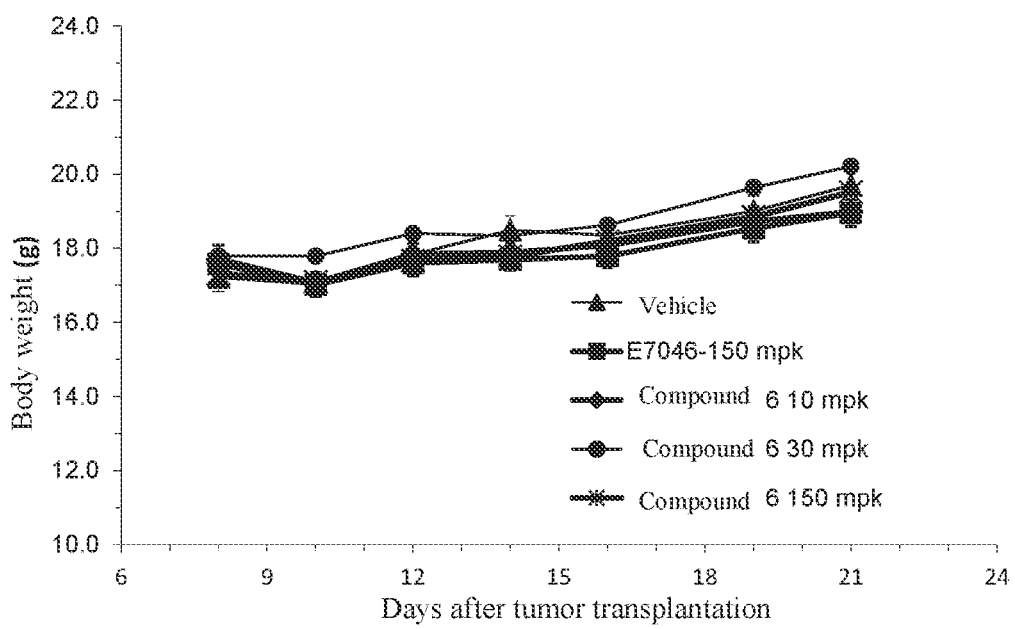
FIG. 2 shows the effect of different doses of compound 6 and E7046 on mouse body weight in CT-26 colorectal cancer model.

FIG. 2 showed that compound 6 and E7046 had no significant effect on the body weight of mouse.

Test Example 4: Inhibitory Effect of Compound 6 and Anti-PD-1 Antibody Administered Alone or in Combination on CT-26 Colorectal Tumor in Mouse Efficacy study on allograft tumor: each 6-week-old female BALB/c mouse was subcutaneously inoculated with $1 \times 10^6$ CT26 cancer cells. When the tumor reached about 60 to 80 mm³, the tumor-bearing mice were randomly grouped to the vehicle group or treatment group. When administered alone or in combination, compound 6 was administered orally (p.o.) in a 0.5% MC suspension at a dose of 30 or 150 mg/kg, once a day. When administered alone or in combination, anti-PD-1 antibody (Invivomab anti-mouse PD-1 (CD279), Abcam) was administered intraperitoneally at a dose of 5 mg/kg, once every 4 days, for a total of 3 times (Q4D×3). The mice in the vehicle group and PD-1 antibody-administered alone group were orally administered with distilled water every day, and the administration time was the same as that of the compound 6 group. The tumor volume and body weight were recorded 2 to 3 times a week. The results are shown in FIG. 3 and FIG. 4.

Figure 3:
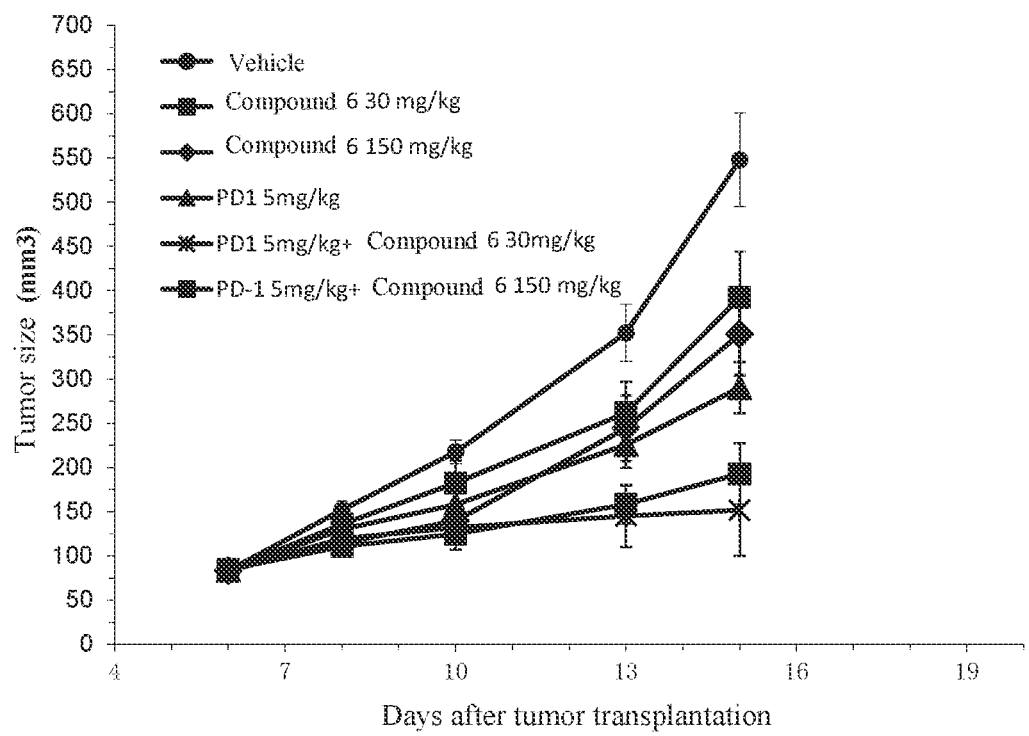
FIG. 3 shows the effect of different doses of compound 6 and anti-PD-1 antibody on tumor growth when administered alone or in combination in CT-26 colorectal cancer model.

It can be seen from FIG. 3 that when compound 6 was administered alone or in combination with the anti-PD-1 antibody, it had a good inhibitory effect on the growth of CT-26 tumor in mouse.

Figure 4:
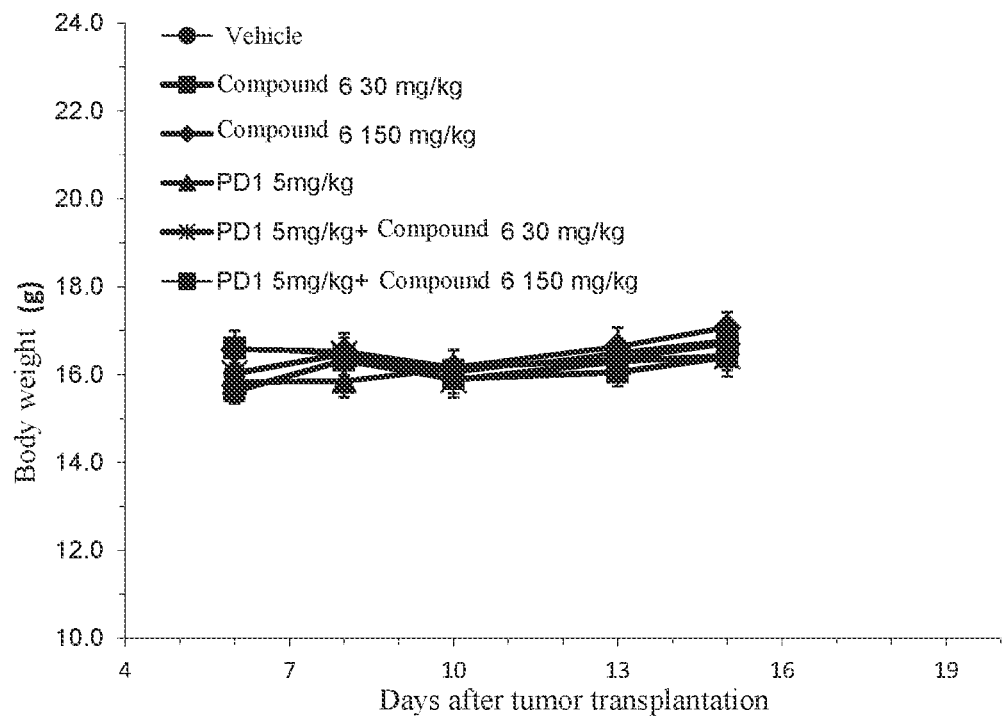
FIG. 4 shows the effect of different doses of compound 6 and anti-PD-1 antibody on mouse body weight when administered alone or in combination in CT-26 colorectal cancer model.

FIG. 4 shows that when compound 6 was administered alone or in combination with the anti-PD-1 antibody, it had no significant effect on the body weight of mouse.

Test Example 5: Inhibitory Effect of Compound 6 and Anti-PD-1 Antibody Administered Alone or in Combination on EM-6 Breast Tumor in Mouse Efficacy study on allograft tumor: each 6-week-old female BALB/c mouse was subcutaneously inoculated with $5\times10^5$ EMT-6 cancer cells. When the tumor reached about 60 to 80 mm$^3$, the tumor-bearing mice were randomly grouped to the vehicle group or treatment group. When administered alone or in combination, compound 6 was administered orally (p.o.) in a 0.5% MC suspension at a dose of 30 mg/kg, once a day. When administered alone or in combination, anti-PD-1 antibody (Invivomab anti-mouse PD-1 (CD279), Abcam) was administered intraperitoneally at a dose of 20 mg/kg on the first administration, and at a dose of 10 mg/kg on the following administrations once every 5 days. The mice in the vehicle group and PD-1 antibody-administered alone group were orally administered with distilled water every day, and the administration time was the same as that of the compound 6 group. The tumor volume and body weight were recorded 2 to 3 times a week. The results are shown in FIG. 5 and FIG. 6.

Figure 5:
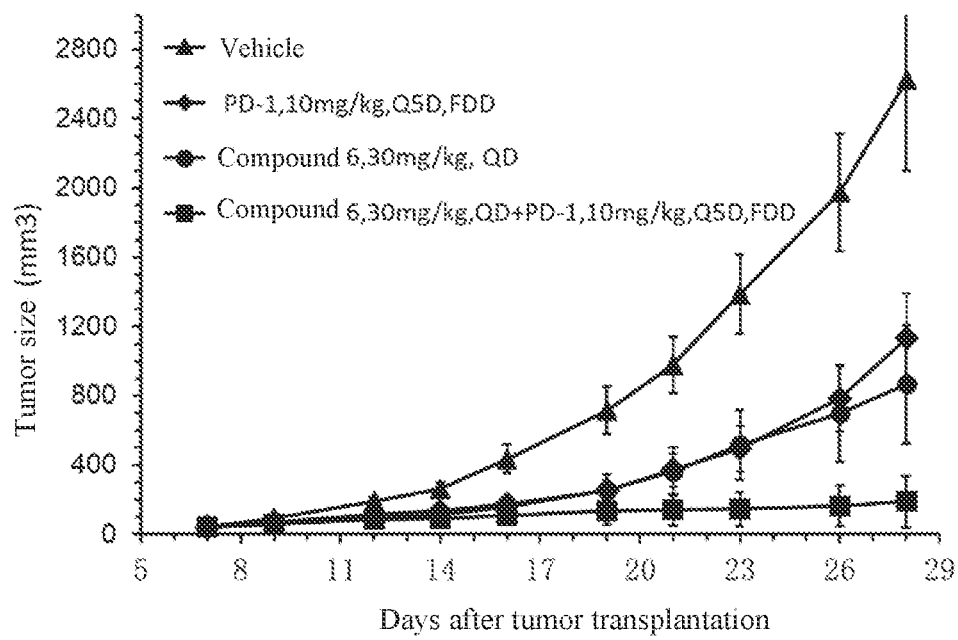
FIG. 5 shows the effect of different doses of compound 6 and anti-PD-1 antibody on tumor growth when administered alone or in combination in EMT-6 breast cancer model.

It can be seen from FIG. 5 that when compound 6 was administered alone or in combination with the anti-PD-1 antibody, it had a good inhibitory effect on the EMT-6 breast tumor in mouse.

Figure 6:
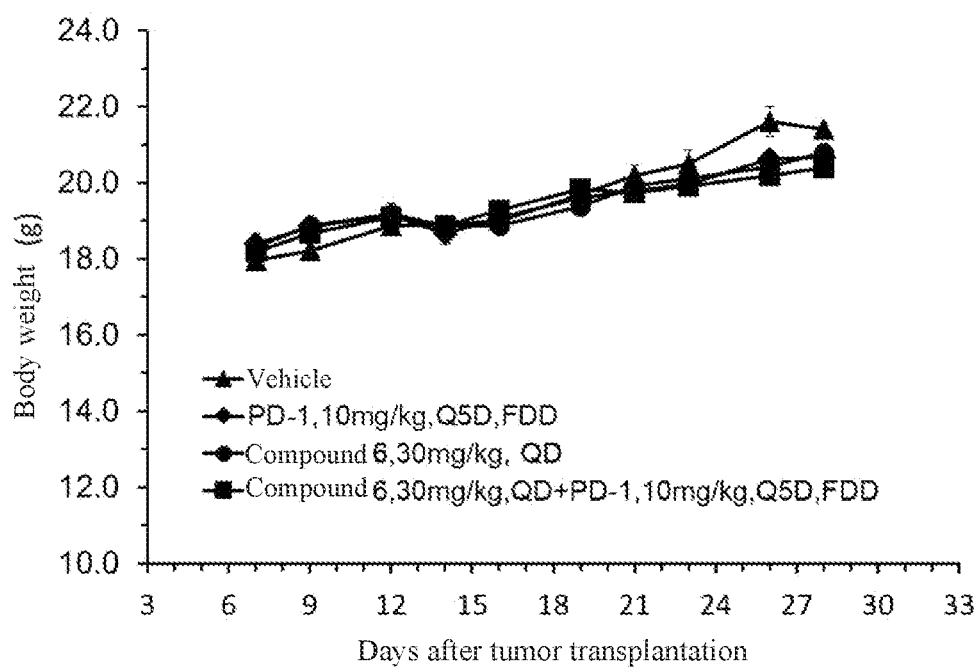
FIG. 6 shows the effect of different doses of compound 6 and anti-PD-1 antibody on mouse body weight when administered alone or in combination in breast cancer tumor model.

FIG. 6 shows that when compound 6 was administered alone or in combination with the anti-PD-1 antibody, it had no significant effect on the body weight of mouse.

What is claimed is:

1. A compound of formula (I):

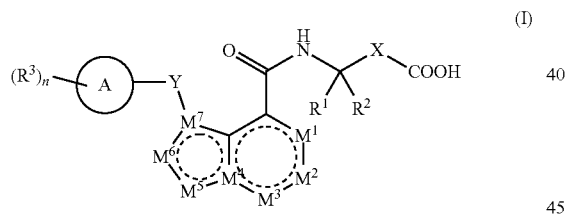

(I)

or a tautomer, mesomer, racemate, enantiomer, diastereomer thereof, or mixture thereof, or a pharmaceutically acceptable salt thereof,
wherein:
$M^1$, $M^2$, $M^3$, $M^5$, and $M^6$ are a C—$R^4$;
$M^4$ is a C atom;
$M^7$ is an N-atom:
ring A is selected from the group consisting of $C_{6-10}$ aryl, $C_{3-6}$ cycloalkyl, 5 to 10 membered heteroaryl and 3 to 6 membered heterocyclyl;

X is 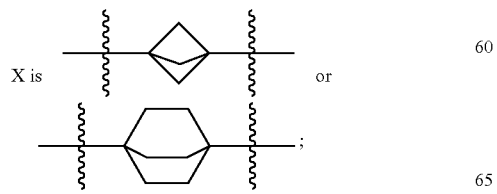 ;

Y is selected from the group consisting of a bond, $C_{1-4}$ alkylene, —CR$^5$R$^6$—, —O—, —OC$_{1-4}$ alkylene-, —NR$^9$C$_{1-4}$ alkylene- and —NR$^9$—, wherein the $C_{1-4}$ alkylene is optionally substituted by one or more substituents selected from the group consisting of H atom, D atom, halogen, hydroxy, cyano, amino, nitro, $C_{1-4}$ alkyl, $C_{1-4}$ alkoxy, haloC$_{1-4}$ alkyl, haloC$_{1-4}$ alkoxy, hydroxyC$_{1-4}$ alkyl, $C_{3-6}$ cycloalkyl, 3 to 6 membered heterocyclyl, $C_{6-10}$ aryl and 5 to 10 membered heteroaryl;

$R^1$ and $R^2$ are identical or different and are each independently selected from the group consisting of H atom, D atom, cyano, $C_{1-4}$ alkyl, $C_{1-4}$ alkoxy, $C_{3-6}$ cycloalkyl, 3 to 6 membered heterocyclyl, —C(O)OR$^4$, C(O)NR$^7$R$^8$, —COR$^4$, —S(O)$_m$R$^4$, —NR$^7$R$^8$, $C_{6-10}$ aryl and 5 to 10 membered heteroaryl, wherein the $C_{1-4}$ alkyl and $C_{1-4}$ alkoxy are each independently optionally substituted by one or more substituents selected from the group consisting of H atom, D atom, halogen, hydroxy, cyano, amino, nitro, $C_{1-4}$ alkyl, $C_{1-4}$ alkoxy, haloC$_{1-4}$ alkyl, haloC$_{1-4}$ alkoxy, hydroxyC$_{1-4}$ alkyl, $C_{3-6}$ cycloalkyl, 3 to 6 membered heterocyclyl, —C(O)OR$^4$, C(O)NR$^7$R$^8$, —COR$^4$, —NR$^4$C(O)NR$^7$R$^8$, —OC(O)NR$^7$R$^8$, —NR$^7$C(O)OR$^4$, —S(O)$_m$R$^4$, —NR$^7$R$^8$, $C_{6-10}$ aryl and 5 to 10 membered heteroaryl; or, $R^1$ and $R^2$ together with the atom to which they are attached form a $C_{3-6}$ cycloalkyl or 3 to 6 membered heterocyclyl, wherein the $C_{3-6}$ cycloalkyl and 3 to 6 membered heterocyclyl are each independently optionally substituted by one or more substituents selected from the group consisting of D atom, halogen, hydroxy, cyano, amino, nitro, —C(O)OR$^4$, C(O)NR$^7$R$^8$, —COR$^4$, —NR$^4$C(O)NR$^7$R$^8$, —OC(O)NR$^7$R$^8$, —NR$^7$C(O)OR$^4$, —S(O)$_m$R$^4$, —NR$^7$R$^8$, $C_{1-4}$ alkyl, $C_{1-4}$ alkoxy, haloC$_{1-4}$ alkyl, haloC$_{1-4}$ alkoxy, hydroxyC$_{1-4}$ alkyl, $C_{3-6}$ cycloalkyl, 3 to 6 membered heterocyclyl, $C_{6-10}$ aryl and 5 to 10 membered heteroaryl;

each $R^3$ is identical or different and each is independently selected from the group consisting of H atom, D atom, halogen, hydroxy, cyano, amino, nitro, $C_{1-4}$ alkyl, $C_{1-4}$ alkoxy, $C_{3-6}$ cycloalkyl, 3 to 6 membered heterocyclyl, $C_{6-10}$ aryl, 5 to 10 membered heteroaryl, —C(O)R$^4$, —C(O)OR$^4$, —OC(O)NR$^7$R$^8$, —NR$^7$C(O)OR$^4$, —S(O)$_m$R$^4$, —NR$^7$R$^8$ and —C(O)NR$^7$R$^8$, wherein the $C_{1-4}$ alkyl, $C_{1-4}$ alkoxy, $C_{3-6}$ cycloalkyl, 3 to 6 membered heterocyclyl, $C_{6-10}$ aryl and 5 to 10 membered heteroaryl are each independently optionally substituted by one or more substituents selected from the group consisting of $C_{1-4}$ alkyl, hydroxyC$_{1-4}$ alkyl, $C_{1-4}$ alkoxy, haloC$_{1-4}$ alkyl, haloC$_{1-4}$ alkoxy, halogen, hydroxy, cyano, amino and nitro;

$R^4$ is selected from the group consisting of H atom, D atom, halogen, hydroxy, amino, $C_{1-4}$ alkyl, $C_{1-4}$ alkoxy, $C_{3-6}$ cycloalkyl, 3 to 6 membered heterocyclyl, $C_{6-10}$ aryl and 5 to 10 membered heteroaryl, wherein the $C_{1-4}$ alkyl, $C_{1-4}$ alkoxy, $C_{3-6}$ cycloalkyl, 3 to 6 membered heterocyclyl, $C_{6-10}$ aryl and 5 to 10 membered heteroaryl are each independently optionally substituted by one or more substituents selected from the group consisting of $C_{1-4}$ alkyl, hydroxyC$_{1-4}$ alkyl, $C_{1-4}$ alkoxy, haloC$_{1-4}$ alkyl, haloC$_{1-4}$ alkoxy, halogen, hydroxy, cyano, amino and nitro;

$R^5$ and $R^6$ are each independently selected from the group consisting of H atom, D atom, $C_{1-4}$ alkyl, $C_{3-6}$ cycloalkyl, 3 to 6 membered heterocyclyl, $C_{6-10}$ aryl and 5 to 10 membered heteroaryl, wherein the $C_{1-4}$ alkyl, $C_{3-6}$ cycloalkyl, 3 to 6 membered heterocyclyl, $C_{6-10}$ aryl and 5 to 10 membered heteroaryl are each independently optionally substituted by one or more substituents selected from the group consisting of $C_{1-4}$ alkyl, hydroxy$C_{1-4}$ alkyl, $C_{1-4}$ alkoxy, halo$C_{1-4}$ alkyl, halo$C_{1-4}$ alkoxy, halogen, hydroxy, cyano, amino and nitro; or, $R^5$ and $R^6$ together with the atom to which they are attached form a $C_{3-6}$ cycloalkyl or 3 to 6 membered heterocyclyl, wherein the $C_{3-6}$ cycloalkyl and 3 to 6 membered heterocyclyl are each independently optionally substituted by one or more substituents selected from the group consisting of halogen, hydroxy, cyano, amino, nitro, $C_{1-4}$ alkyl, $C_{1-4}$ alkoxy, halo$C_{1-4}$ alkyl, halo$C_{1-4}$ alkoxy, hydroxy$C_{1-4}$ alkyl, $C_{3-6}$ cycloalkyl, 3 to 6 membered heterocyclyl, $C_{6-10}$ aryl and 5 to 10 membered heteroaryl;

$R^7$ and $R^8$ are each independently selected from the group consisting of H atom, D atom, $C_{1-4}$ alkyl, halo$C_{1-4}$ alkyl, $C_{3-6}$ cycloalkyl, 3 to 6 membered heterocyclyl, $C_{6-10}$ aryl and 5 to 10 membered heteroaryl, wherein the $C_{1-4}$ alkyl, halo$C_{1-4}$ alkyl, $C_{3-6}$ cycloalkyl, 3 to 6 membered heterocyclyl, $C_{6-10}$ aryl and 5 to 10 membered heteroaryl are each independently optionally substituted by one or more substituents selected from the group consisting of $C_{1-4}$ alkyl, hydroxy$C_{1-4}$ alkyl, $C_{1-4}$ alkoxy, halo$C_{1-4}$ alkyl, halo$C_{1-4}$ alkoxy, halogen, hydroxy, cyano, amino and nitro;

$R^9$ is selected from the group consisting of H atom, D atom and $C_{1-4}$ alkyl, wherein the $C_{1-4}$ alkyl is optionally substituted by one or more substituents selected from the group consisting of hydroxy$C_{1-4}$ alkyl, $C_{1-4}$ alkoxy, halo$C_{1-4}$ alkyl, halo$C_{1-4}$ alkoxy, halogen, hydroxy, cyano, amino and nitro;

m is 0, 1 or 2; and n is 0, 1, 2, 3 or 4.

2. The compound of formula (I) according to claim 1, being a compound of formula (II):

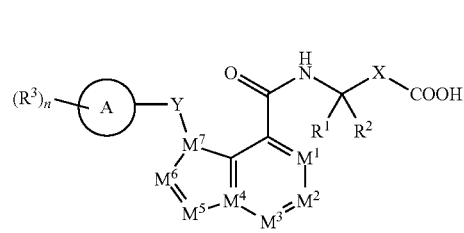

(II)

wherein $M^1$, $M^3$, $M^5$ and $M^6$ are each independently a CH or C-halogen, $M^2$ is a C—$R^4$, $M^7$ is an N atom, $M^4$ is a C atom, and ring A, $R^1$, $R^2$, $R^3$, $R^4$, X, Y and n are as defined in claim 1.

3. The compound of formula (I) according to claim 1, wherein Y is a $C_{1-4}$ alkylene.

4. The compound of formula (I) according to claim 1, wherein $R^1$ and $R^2$ are identical or different and are each independently selected from the group consisting of H atom, D atom and $C_{1-4}$ alkyl; or, $R^1$ and $R^2$ together with the atom to which they are attached form a $C_{3-6}$ cycloalkyl.

5. The compound of formula (I) according to claim 1, being a compound of formula (III):

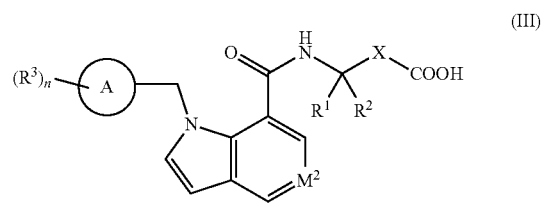

(III)

or a tautomer, mesomer, racemate, enantiomer, diastereomer thereof, or mixture thereof, or a pharmaceutically acceptable salt thereof, wherein:

$R^1$ and $R^2$ are identical or different and are each independently selected from the group consisting of H atom, D atom and $C_{1-4}$ alkyl; or, $R^1$ and $R^2$ together with the atom to which they are attached form a $C_{3-6}$ cycloalkyl;

$M^2$ is a C—$R^4$;

$R^4$ is selected from the group consisting of H atom, D atom and halogen; and

X, ring A, $R^3$ and n are as defined in claim 1.

6. The compound of formula (I) according to claim 1, wherein ring A is selected from the group consisting of phenyl, pyridyl, quinolinyl, benzofuranyl, morpholinyl, pyrazole, cyclopropyl, isoxazole, benzoxazole and benzothiazole.

7. The compound of formula (I) according to claim 1, wherein each $R^3$ is identical or different and each is independently selected from the group consisting of H atom, D atom, halogen, $C_{1-4}$ alkyl, fluoro$C_{1-4}$ alkyl, phenyl, hydroxy$C_{1-4}$ alkyl-substituted phenyl, morpholinyl, pyridyl, pyrazolyl, $C_{1-4}$ alkyl-substituted pyrazolyl, hydroxy$C_{1-4}$ alkyl-substituted pyrazolyl, cyclopropyl, isoxazolyl, piperidinyl and hydroxy-substituted piperidinyl.

8. The compound of formula (I) according to claim 1, selected from the group consisting of:

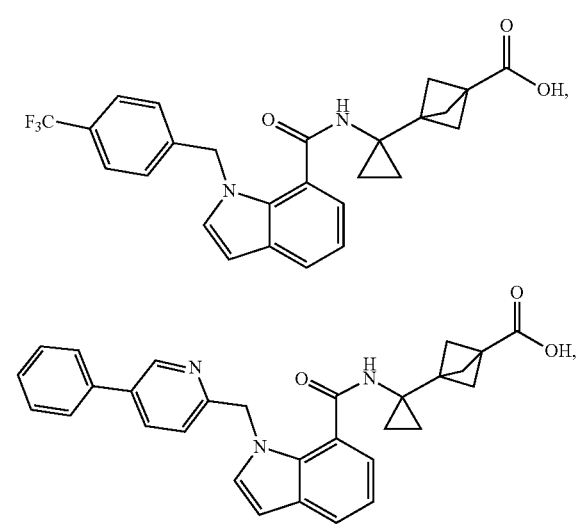

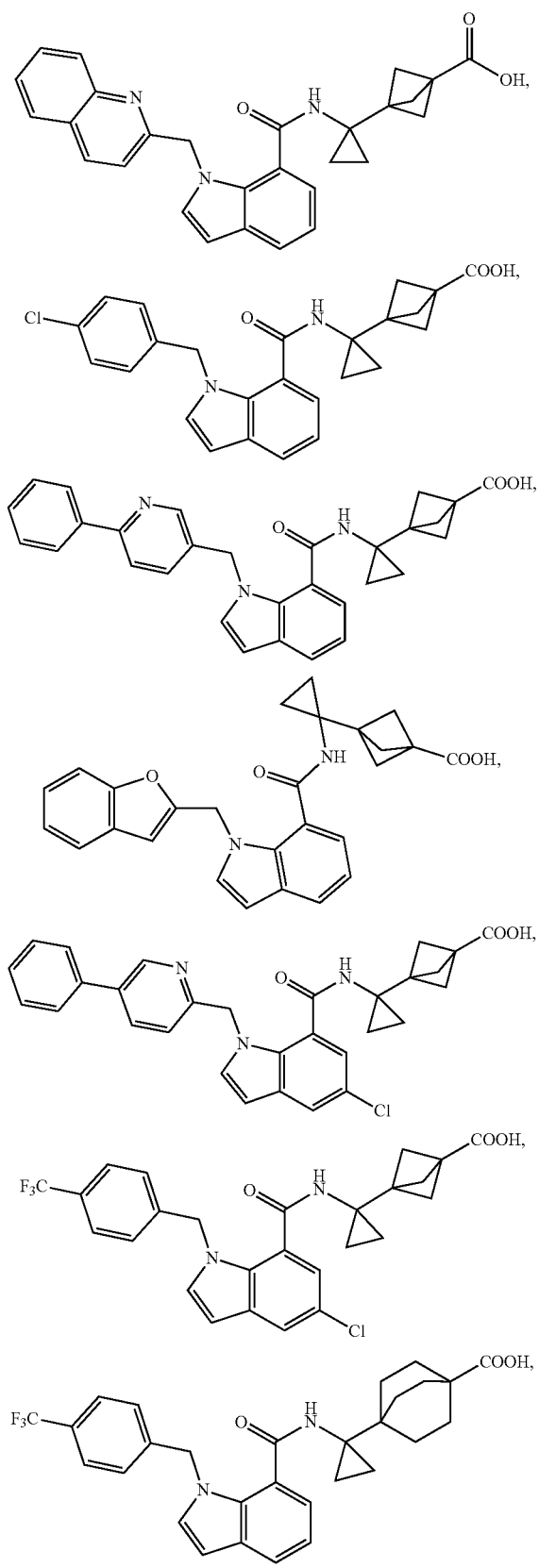
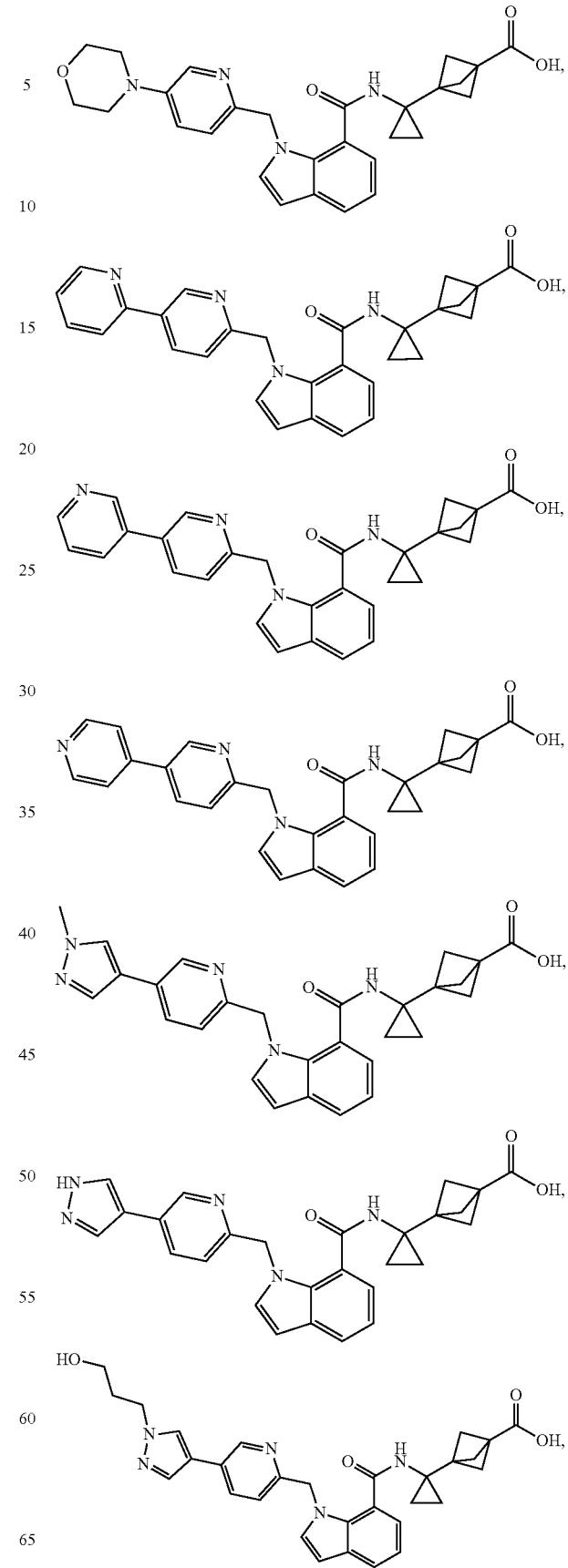

89
-continued
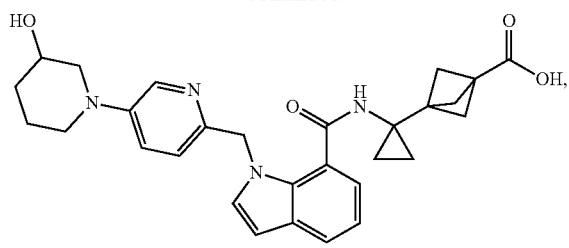
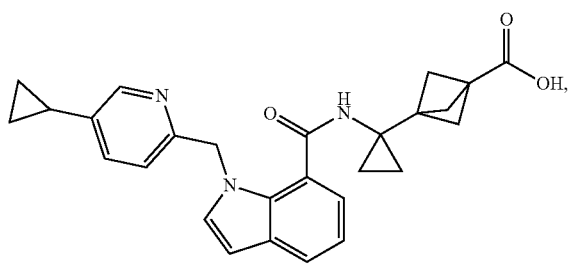
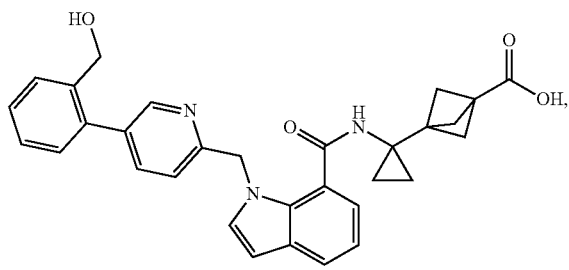
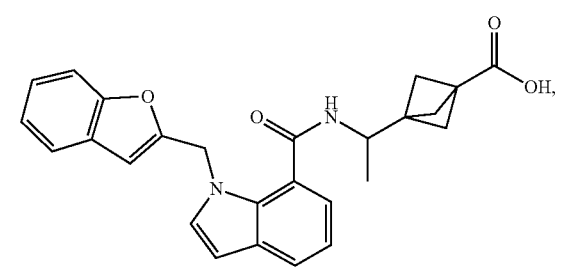
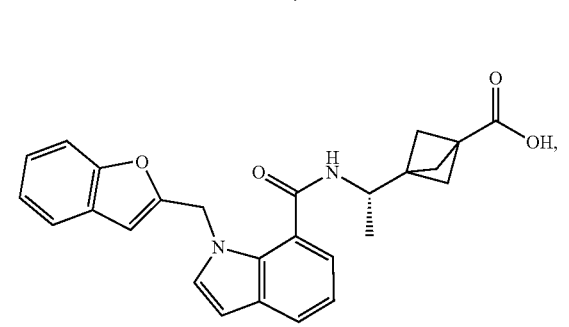
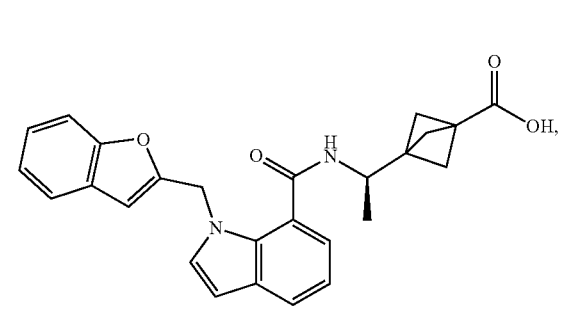
90
-continued
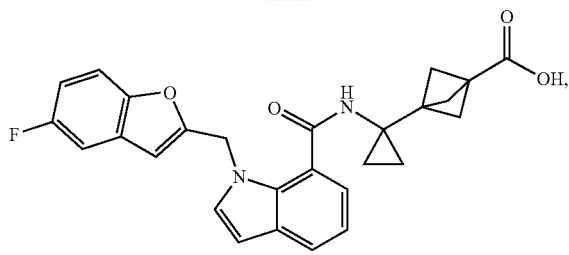
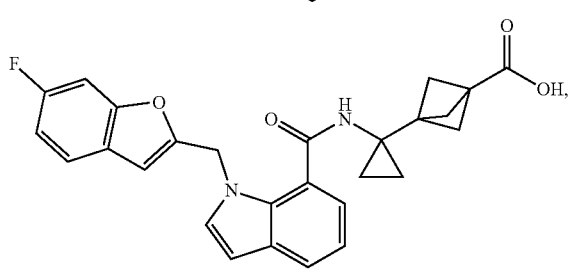
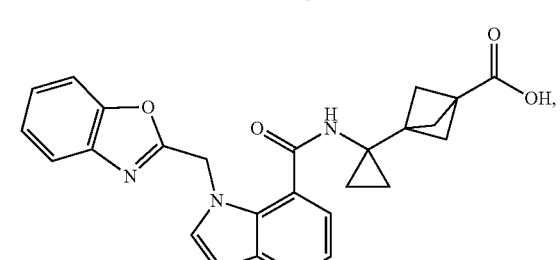
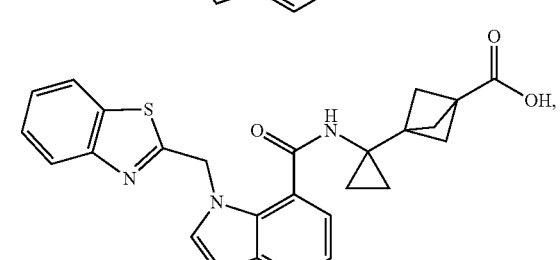
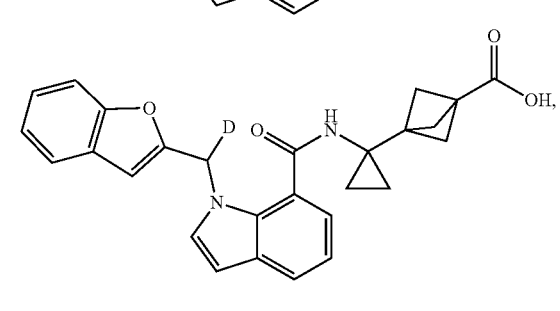
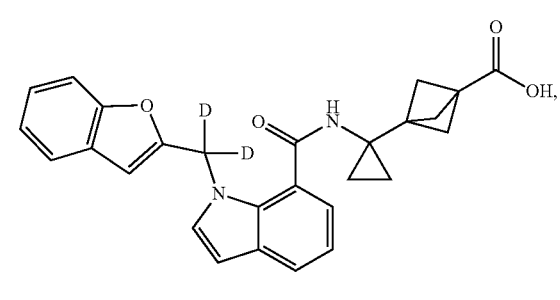

-continued

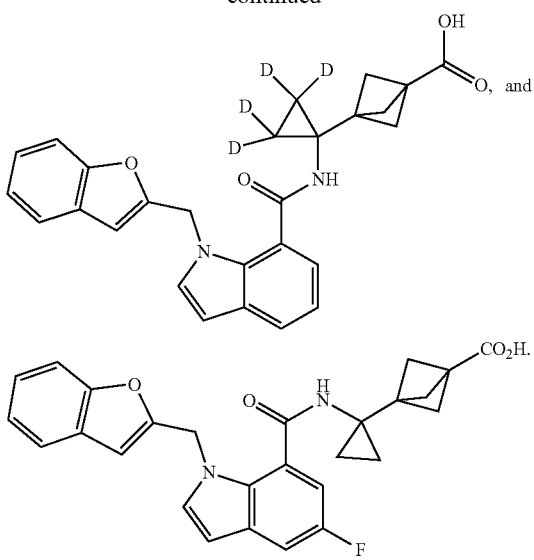

9. A method for preparing the compound of formula (I) according to claim 1, comprising the following steps of:

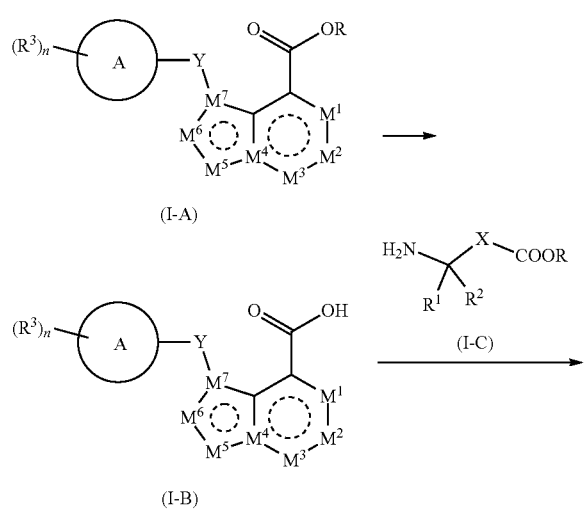

-continued hydrolyzing a compound of formula (I-A) to obtain a compound of formula (I-B), subjecting the compound of formula (I-B) and a compound of formula (I-C) to a condensation reaction to obtain a compound of formula (I-D), and hydrolyzing the compound of formula (I-D) to remove the R group and thus obtain the compound of formula (I);

wherein:
R is a $C_{1-4}$ alkyl; and
$M^1$ to $M^7$, ring A, X, Y, $R^1$, $R^2$, $R^3$ and n are as defined in claim 1.

10. A pharmaceutical composition, comprising a therapeutically effective amount of the compound of formula (I) according to claim 1, and pharmaceutically acceptable carrier(s), diluent(s) or excipient(s).

11. The pharmaceutical composition according to claim 10, further comprising an antibody selected from the group consisting of anti-CTLA4 antibody, anti-PDL1 antibody and anti-PD1 antibody.

12. The pharmaceutical composition according to claim 11, wherein the antibody is selected from the group consisting of Ipilimumab, Tremelimumab, Pembrolizumab, Nivolumab, Atezolizumab, Avelumab, Durvlumab, Pidilizumab, AMP-224, AMP-514, PDR001, Cemiplimab, BMS-936559, CK-301, Toripalimab, Sintilimab, Camrelizumab, Tislelizumab, KN035, GLS-010, GB226, CS1001, CS1003, BAT-1306, HX008, AK105, LZM009, HLX10, HLX20, KL-A167, F520, GR1405 and MSB2311.

* * * * *